(12) United States Patent
Pätzold et al.

(10) Patent No.: US 11,987,788 B2
(45) Date of Patent: *May 21, 2024

(54) METHODS AND COMPOSITIONS FOR CHANGING THE COMPOSITION OF THE SKIN MICROBIOME USING COMPLEX MIXTURES OF BACTERIAL STRAINS

(71) Applicant: S-Biomedic NV, Beerse (BE)

(72) Inventors: Bernhard Pätzold, Berchem (BE); Marc Güell, Barcelona (ES)

(73) Assignee: S-Biomedic NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/006,054

(22) Filed: Aug. 28, 2020

(65) Prior Publication Data

US 2020/0392452 A1    Dec. 17, 2020

Related U.S. Application Data

(63) Continuation of application No. 15/567,941, filed as application No. PCT/US2016/028421 on Apr. 20, 2016, now Pat. No. 10,774,305.

(60) Provisional application No. 62/216,258, filed on Sep. 9, 2015, provisional application No. 62/150,225, filed on Apr. 20, 2015.

(51) Int. Cl.
| | | |
|---|---|---|
| C12N 1/20 | (2006.01) | |
| A61K 9/00 | (2006.01) | |
| A61K 35/00 | (2006.01) | |
| A61K 35/74 | (2015.01) | |
| A61P 17/10 | (2006.01) | |
| C12Q 1/04 | (2006.01) | |
| C12Q 1/533 | (2006.01) | |
| C12R 1/01 | (2006.01) | |

(52) U.S. Cl.
CPC ............ *C12N 1/20* (2013.01); *A61K 9/0014* (2013.01); *A61K 35/74* (2013.01); *A61P 17/10* (2018.01); *C12N 1/205* (2021.05); *C12Q 1/04* (2013.01); *C12Q 1/533* (2013.01); *A61K 2035/115* (2013.01); *C12R 2001/01* (2021.05); *G01N 2333/195* (2013.01)

(58) Field of Classification Search
CPC ........... A61P 17/10; C12N 1/20; C12N 1/205; A61K 9/0014; A61K 35/74; A61K 2035/115; C12Q 1/04; C12Q 1/533; C12R 2001/01; G01N 2333/195
USPC ........................................................ 424/93.3
See application file for complete search history.

(56) References Cited

U.S. PATENT DOCUMENTS

| | | |
|---|---|---|
| 5,650,149 A | 7/1997 | Okabe |
| 6,743,609 B1 | 6/2004 | Rosson et al. |
| 6,821,770 B1 | 11/2004 | Hogan |
| 6,982,273 B1 | 1/2006 | Majeed et al. |
| 7,919,250 B2 | 4/2011 | Blaser et al. |
| 9,889,165 B2 | 2/2018 | Taylor et al. |
| 10,774,305 B2 | 9/2020 | Pätzold et al. |
| 11,103,443 B2 | 8/2021 | Rasochova et al. |
| 11,541,081 B2 | 1/2023 | Pätzold et al. |
| 2006/0286054 A1 | 12/2006 | Gomez |
| 2010/0260695 A1 | 10/2010 | Durke-Colvin et al. |
| 2011/0014248 A1 | 1/2011 | Castiel et al. |
| 2013/0289005 A1 | 10/2013 | Guthery |
| 2014/0234260 A1 | 8/2014 | Borody |
| 2014/0363398 A1 | 12/2014 | Jones et al. |
| 2015/0037285 A1 | 2/2015 | Blaser et al. |
| 2015/0050245 A1 | 2/2015 | Herman et al. |
| 2015/0086581 A1 | 3/2015 | Li et al. |
| 2015/0361436 A1 | 12/2015 | Hitchcock et al. |
| 2016/0151427 A1 | 6/2016 | Whitlock et al. |
| 2017/0058328 A1 | 3/2017 | Li et al. |
| 2017/0065647 A1 | 3/2017 | Kim et al. |
| 2018/0142202 A1 | 5/2018 | Pätzold et al. |
| 2019/0314428 A1 | 10/2019 | Pätzold et al. |
| 2021/0187043 A9 | 6/2021 | Pätzold et al. |
| 2022/0000762 A1 | 1/2022 | Lood |

FOREIGN PATENT DOCUMENTS

| | | |
|---|---|---|
| EP | 3 139 939 A1 | 3/2017 |
| EP | 3 158 054 A1 | 4/2017 |
| EP | 2 825 676 B1 | 12/2017 |
| EP | 3 360 560 A1 | 8/2018 |
| EP | 3 528 825 A1 | 8/2019 |
| WO | WO 2011/152566 A2 | 12/2011 |
| WO | WO 2012/153206 A1 | 11/2012 |
| WO | WO 2013/067185 A1 | 5/2013 |
| WO | WO 2013/142378 A9 | 9/2013 |
| WO | WO 2015/171899 A1 | 11/2015 |
| WO | WO 2015/195845 A1 | 12/2015 |
| WO | WO 2017/044835 A1 | 3/2017 |

(Continued)

OTHER PUBLICATIONS

Agak et al., Propionibacterium acnes Induces an IL-17 Response in Acne Vulgaris that Is Regulated by Vitamin A and Vitamin D, Journal of Investigative Dermatology, (2014) 134, pp. 366-373.*

Bruggemann et al., CRISPR/cas Loci of Type II Propionibacterium acnes Confer Immunity against Acquisition of Mobile Elements Present in Type I P. acnes, PLoS ONE, vol. 7, Iss. 3, (2012), pp. 1-10.*

Kasimatis et al., Analysis of Complete Genomes of Propionibacterium acnes Reveals a Novel Plasmid and Increased Pseudogenes in an Acne Associated Strain, BioMed Research International, vol. 2013, (2013), pp. 1-11.*

(Continued)

*Primary Examiner* — Jennifer M. H. Tichy

(74) *Attorney, Agent, or Firm* — Wolf, Greenfield & Sacks, P.C.

(57) ABSTRACT

Aspects of the invention relate to compositions comprising one or more live bacterial strains for topical administration to the skin, wherein the one or more live bacterial strains are *Propionibacterium acnes* (*P. acnes*) bacterial strains, and methods for use.

12 Claims, 18 Drawing Sheets

Specification includes a Sequence Listing.

(56) References Cited

FOREIGN PATENT DOCUMENTS

| WO | WO 2017/136738 A2 | 8/2017 |
|---|---|---|
| WO | WO 2017/147507 A1 | 8/2017 |
| WO | WO 2017/168263 A1 | 10/2017 |
| WO | WO 2017/184992 A1 | 10/2017 |
| WO | WO 2017/185016 A1 | 10/2017 |
| WO | WO 2017/185018 A1 | 10/2017 |
| WO | WO 2018/060799 A1 | 4/2018 |
| WO | WO 2018/073651 A1 | 4/2018 |
| WO | WO 2019/238968 A1 | 12/2019 |
| WO | WO 2020/099663 A1 | 5/2020 |
| WO | WO 2021/063526 A1 | 4/2021 |
| WO | WO 2021/063527 A1 | 4/2021 |
| WO | WO 2021/063528 A1 | 4/2021 |
| WO | WO 2021/063529 A1 | 4/2021 |
| WO | WO 2021/063530 A1 | 4/2021 |
| WO | WO 2021/063531 A1 | 4/2021 |
| WO | WO 2021/063532 A1 | 4/2021 |

OTHER PUBLICATIONS

U.S. Appl. No. 16/343,277, filed Apr. 18, 2019, Pätzold et al.
EP 16783755.8, Oct. 15, 2018, Partial Extended European Search Report.
EP 16783755.8, Jan. 23, 2019, Extended European Search Report.
PCT/US2016/028241, Jul. 29, 2016, International Search Report and Written Opinion.
PCT/US2016/028241, Nov. 2, 2017, International Preliminary Report of Patentability.
PCT/IB2017/001481, Apr. 11, 2018, International Search Report and Written Opinion.
PCT/IB2017/001481, May 2, 2019, International Preliminary Report on Patentability.
International Search Report and Written Opinion dated Jul. 29, 2016 for Application No. PCT/US2016/028241.
International Preliminary Report on Patentability dated Nov. 2, 2017 for Application No. PCT/US2016/028241.
International Search Report and Written Opinion dated Apr. 11, 2018 for Application No. PCT/IB2017/001481.
International Preliminary Report on Patentability dated May 2, 2019 for Application No. PCT/IB2017/001481.
Partial Extended European Search Report dated Oct. 15, 2018 for Application No. EP 16783755.8.
Extended European Search Report dated Jan. 23, 2019 for Application No. EP 16783755.8.
[No Author Listed] A Study of the Safety, Engraftment, and Action of NB01 in Adults With Moderate Acne. Clinical Trials.gov Identifier: NCT03450369. First posted: Mar. 1, 2018; study completion date: Jun. 18, 2018; last update posted: Nov. 28, 2018. Retrieved from the Internet https://clinicaltrials.gov/ct2/show/NCT03450369 on May 23, 2019. 16 pages.
[No Author Listed] Human Microbiome Project Consortium. Structure, function and diversity of the healthy human microbiome. Nature. Jun. 13, 2012;486(7402):207-14. doi: 10.1038/nature11234.
[No Author Listed] Sigma-Aldrich Fatty Acid/FAME Application Guide: Analysis of Foods for Nutritional Services. Retrieved on May 7, 2018. https://www.google.com/url?sa=t&rct=j&q=&esrc=s&source=web&cd=1&ved=0ahUKEwji5rXDxvbaAhUFVt8KHZ0fC9YQFgg1MAA&url=https%3A%2F%2Fwww.researchgate.net%2Fprofile%2FDang_Nguyen_Thoai%2Fpost%2FWhat_is_valu_input_GC_analysis_for_fish_oil_fatty_acid_profile%2Fattachment%2F59d6351579197b8077992b09%2FAS%3A382926094127111%401468308103322%2Fdownload%2FFatty%2BAcid%2B-%2BFAME%2BApplication%2BGuide.pdf&usg=AOvVawOLpU-YvUgLBa0RGwYBT5FK.
[No Author Listed] The NIH Human Microbiome Project. Genome Res. Dec. 2009;19(12):2317-23. doi: 10.1101/gr.096651.109. Epub Oct. 9, 2009.
Allgaier et al., Elucidation of the Structure of Epidermin, a Ribosomally Synthesized, Tetracyclic Heterodetic Polypeptide Antibiotic. Angew. Chem. Int. Ed. Engl. 1985;24(12):1051-1053.
Allgaier et al., Epidermin: sequencing of a heterodetic tetracyclic 21-peptide amide antibiotic. Eur J Biochem. Oct. 1, 1986;160(1):9-22.
Azoulay et al., Isotretinoin therapy and the incidence of acne relapse: a nested case-control study. Br J Dermatol. Dec. 2007;157(6):1240-8. Epub Oct. 26, 2007.
Barnard et al., Strains of the Propionibacterium acnes type III lineage are associated with the skin condition progressive macular hypomelanosis. Sci Rep. Aug. 24, 2016;6:31968. doi: 10.1038/srep31968.
Bek-Thomsen et al., Acne is not associated with yet-uncultured bacteria. J Clin Microbiol. Oct. 2008;46(10):3355-60. doi: 10.1128/JCM.00799-08. Epub Aug. 20, 2008.
Bek-Thomsen et al., Proteome analysis of human sebaceous follicle infundibula extracted from healthy and acne-affected skin. PLoS One. Sep. 19, 2014;9(9):e107908. doi: 10.1371/journal.pone.0107908. eCollection 2014.
Belkaid et al., Dialogue between skin microbiota and immunity. Science. Nov. 21, 2014;346(6212):954-9. doi: 10.1126/science.1260144.
Berson et al., Current concepts in the treatment of acne: report from a clinical roundtable. Cutis. Jul. 2003;72(1 Suppl):5-13.
Bonacci et al., Conjugated linoleic acid is a preferential substrate for fatty acid nitration. J Biol Chem. Dec. 28, 2012;287(53):44071-82. doi: 10.1074/jbc.M112.401356. Epub Nov. 9, 2012.
Bowe et al., Acne Vulgaris, Probiotics and the Gut-Brain-Skin Axis-Back to the Future ?. Gut Pathogens. 2011;3:1-11.
Bruggemann et al., CRISPR/cas loci of type II Propionibacterium acnes confer immunity against acquisition of mobile elements present in type I P. acnes. PLoS One. 2012;7(3):e34171. doi: 10.1371/journal.pone.0034171. Epub Mar. 30, 2012.
Brzuszkiewicz et al., Comparative genomics and transcriptomics of Propionibacterium acnes. PLoS One. 2011;6(6):e21581. doi: 10.1371/journal.pone.0021581. Epub Jun. 27, 2011.
Churruca et al., Conjugated linoleic acid isomers: differences in metabolism and biological effects. Biofactors. Jan.-Feb. 2009;35(1):105-11. doi: 10.1002/biof.13.
Clavaud et al., Dandruff is associated with disequilibrium in the proportion of the major bacterial and fungal populations colonizing the scalp. PLoS One. 2013;8(3):e58203. doi: 10.1371/journal.pone.0058203. Epub Mar. 6, 2013. Erratum in: PLoS One. 2013;8(10). doi: 10.1371/annotation/bcff4a59-10b7-442a-8181-12fa69209e57.
Delmastro-Greenwood et al., Redox-dependent anti-inflammatory signaling actions of unsaturated fatty acids. Annu Rev Physiol. 2014;76:79-105. doi: 10.1146/annurev-physiol-021113-170341. Epub Oct. 16, 2013. Author manuscript.
Deng et al., Linoleic acid isomerase from Propionibacterium acnes: purification, characterization, molecular cloning, and heterologous expression. Appl Biochem Biotechnol. Dec. 2007;143(3):199-211.
Dore et al., The influence of diet on the gut microbiota and its consequences for health. Curr Opin Biotechnol. Apr. 2015;32:195-199. doi: 10.1016/j.copbio.2015.01.002. Epub Jan. 20, 2015.
Downing et al., Essential fatty acids and acne. J Am Acad Dermatol. Feb. 1986;14(2 Pt 1):221-5.
Draelos, Cosmeceuticals: undefined, unclassified, and unregulated. Clin Dermatol. Sep.-Oct. 2009;27(5):431-4. doi: 10.1016/j.clindermatol.2009.05.005.
Flores et al., A direct PCR approach to accelerate analyses of human-associated microbial communities. PLoS One. 2012;7(9):e44563. doi: 10.1371/journal.pone.0044563. Epub Sep. 4, 2012.
GENBANK Submission; NIH/NCBI, Accession No. CP003084: "Propionibacterium acnes ATCC 11828, complete genome.", GenBank Record created on Oct. 24, 2011. 4 pages.
GENBANK Submission; NIH/NCBI, Accession No. CP003293: "Propionibacterium acnes HL096PA1, complete genome", GenBank Record created on Apr. 23, 2013. 2 pages.
Götz et al., Epidermin and gallidermin: Staphylococcal lantibiotics. Int J Med Microbiol. Jan. 2014;304(1):63-71. doi: 10.1016/j.ijmm.2013.08.012. Epub Sep. 4, 2013.

(56) References Cited

OTHER PUBLICATIONS

Gribbon et al., Interaction of Propionibacterium acnes with skin lipids in vitro. J Gen Microbiol. Aug. 1993;139(8):1745-51.
Grice, The skin microbiome. Nat Rev Microbiol. Apr. 2011;9(4):244-53. doi: 10.1038/nrmicro2537. Review. Erratum in: Nat Rev Microbiol. Aug. 2011;9(8):626.
Grice, The skin microbiome: potential for novel diagnostic and therapeutic approaches to cutaneous disease. Semin Cutan Med Surg. Jun. 2014;33(2):98-103.
Guy et al., Modeling acne in vitro. J Invest Dermatol. Jan. 1996;106(1):176-82.
Hogquist et al., Interleukin 1 is processed and released during apoptosis. Proc Natl Acad Sci USA. Oct. 1, 1991;88(19):8485-9.
Holmes, Potential role of microorganisms in the pathogenesis of rosacea. J Am Acad Dermatol. Dec. 2013;69(6):1025-32. doi: 10.1016/j.jaad.2013.08.006. Epub Sep. 5, 2013.
Horváth et al., Genome sequence of Propionibacterium acnes type II strain ATCC 11828. J Bacteriol. Jan. 2012;194(1):202-3. doi: 10.1128/JB.06388-11.
Hunyadkürti et al., Complete genome sequence of Propionibacterium acnes type IB strain 6609. J Bacteriol. Sep. 2011;193(17):4561-2. doi: 10.1128/JB.05372-11. Epub Jun. 24, 2011.
Iinuma et al., Involvement of Propionibacterium acnes in the augmentation of lipogenesis in hamster sebaceous glands in vivo and in vitro. J Invest Dermatol. Sep. 2009;129(9):2113-9. doi: 10.1038/jid.2009.46. Epub Mar. 12, 2009.
Im et al. Enzymes of carbohydrate metabolism in normal human sebaceous glands. J Invest Dermatol. Mar. 1974;62(3):153-60.
Isard et al., Propionibacterium acnes activates the IGF-1/IGF-1R system in the epidermis and induces keratinocyte proliferation. J Invest Dermatol. Jan. 2011;131(1):59-66. doi: 10.1038/jid.2010.281. Epub Oct. 7, 2010.
Jasson et al., Different strains of Propionibacterium acnes modulate differently the cutaneous innate immunity. Exp Dermatol. Sep. 2013;22(9):587-92. doi: 10.1111/exd.12206.
Jensen, Characterization of health—associated *Propionibacterium acnes* strains. 60 ECTS Master Thesis in Biology for the degree cand. scient. Aarhus Universitet, Department of Biomedicine, Health, Denmark. Jan. 2016. 52 pages.
Karoglan et al., Safety and Efficacy of Topically Applied Selected *Cutibacterium acnes* Strains over Five Weeks in Patients with Acne Vulgaris: An Open-label, Pilot Study. Acta Derm Venereol. Dec. 1, 2019;99(13):1253-1257. doi: 10.2340/00015555-3323.
Kasimatis et al., Analysis of complete genomes of Propionibacterium acnes reveals a novel plasmid and increased pseudogenes in an acne associated strain. Biomed Res Int. 2013;2013:918320. doi: 10.1155/2013/918320. Epub May 13, 2013.
Kearney et al., Correlations between human skin bacteria and skin lipids. Br J Dermatol. May 1984;110(5):593-9.
King et al., A double-blind study of the effects of 13-cis-retinoic acid on acne, sebum excretion rate and microbial population. Br J Dermatol. Nov. 1982;107(5):583-90.
Ko et al., Differential susceptibility of Propionibacterium acnes, P. granulosum and P. avidum to free fatty acids. J Invest Dermatol. Dec. 1978;71(6):363-5.
Kong et al., Temporal shifts in the skin microbiome associated with disease flares and treatment in children with atopic dermatitis. Genome Res. May 2012;22(5):850-9. doi: 10.1101/gr.131029.111. Epub Feb. 6, 2012.
Kramer et al., Analysis of conjugated linoleic acid and trans 18:1 isomers in synthetic and animal products. Am J Clin Nutr. Jun. 2004;79(6 Suppl):1137S-1145S. doi: 10.1093/ajcn/79.6.1137S.
Letawe et al., Digital image analysis of the effect of topically applied linoleic acid on acne microcomedones. Clin Exp Dermatol. Mar. 1998;23(2):56-8.
Leyden, Current issues in antimicrobial therapy for the treatment of acne. J Eur Acad Dermatol Venereol. 2001;15 Suppl 3:51-5.
Liao et al., Survivability and long-term preservation of bacteria in water and in phosphate-buffered saline. Lett Appl Microbiol. 2003;37(1):45-50.
Liavonchanka et al., Structure and mechanism of the Propionibacterium acnes polyunsaturated fatty acid isomerase. Proc Natl Acad Sci U S A. Feb. 21, 2006;103(8):2576-81. Epub Feb. 13, 2006.
Makrantonaki et al., An update on the role of the sebaceous gland in the pathogenesis of acne. Dermatoendocrinol. Jan. 2011;3(1):41-9. doi: 10.4161/derm.3.1.13900.
Mcginley et al., Regional variations of cutaneous propionibacteria. Appl Environ Microbiol. Jan. 1978;35(1):62-6.
Mckain et al., Metabolism of conjugated linoleic acids and 18 : 1 fatty acids by ruminal bacteria: products and mechanisms. Microbiology. Feb. 2010;156(Pt 2):579-88. doi: 10.1099/mic.0.036442-0. Epub Nov. 19, 2009.
Mclane, Analysis of common side effects of isotretinoin. J Am Acad Dermatol. Nov. 2001;45(5):S188-94.
Mourelatos et al., Temporal changes in sebum excretion and propionibacterial colonization in preadolescent children with and without acne. Br J Dermatol. Jan. 2007;156(1):22-31.
Moya-Camarena et al., Conjugated linoleic acid is a potent naturally occurring ligand and activator of PPARalpha. J Lipid Res. Aug. 1999;40(8):1426-33.
Mudiyanselage et al., Ultraviolet a induces generation of squalene monohydroperoxide isomers in human sebum and skin surface lipids in vitro and in vivo. J Invest Dermatol. Jun. 2003;120(6):915-22.
Nagy et al., Distinct strains of Propionibacterium acnes induce selective human beta-defensin-2 and interleukin-8 expression in human keratinocytes through toll-like receptors. J Invest Dermatol. May 2005;124(5):931-8.
Nodake et al., Pilot study on novel skin care method by augmentation with *Staphylococcus epidermidis*, an autologous skin microbe—A blinded randomized clinical trial. J Dermatol Sci. Aug. 2015;79(2):119-26. doi: 10.1016/j.jdermsci.2015.05.001. Epub May 14, 2015.
Oberemok et al., Acne Vulgaris, I: Pathogenesis and Diagnosis. Cutis. 2002;70:101-105.
Oh et al., Biogeography and individuality shape function in the human skin metagenome. Nature. Oct. 2, 2014;514(7520):59-64. doi: 10.1038/nature13786.
Oh et al., Temporal Stability of the Human Skin Microbiome. Cell. May 5, 2016;165(4):854-66. doi: 10.1016/j.cell.2016.04.008.
Olle, Medicines from microbiota. Nat Biotechnol. Apr. 2013;31(4):309-15. doi: 10.1038/nbt.2548.
Ottaviani et al., Peroxidated squalene induces the production of inflammatory mediators in HaCaT keratinocytes: a possible role in acne vulgaris. J Invest Dermatol. Nov. 2006;126(11):2430-7. Epub Jun. 15, 2006.
Paetzold et al., Skin microbiome modulation induced by probiotic solutions. Microbiome. Jun. 24, 2019;7(1):95. doi: 10.1186/s40168-019-0709-3.
Pappas et al., Sebum analysis of individuals with and without acne. Dermatoendocrinol. May 2009;1(3):157-61.
Pierre et al., Trans-10, cis-12 conjugated linoleic acid induced cell death in human colon cancer cells through reactive oxygen species-mediated ER stress. Biochim Biophys Acta. Apr. 2013;1831(4):759-68. doi: 10.1016/j.bbalip.2013.01.005. Epub Jan. 15, 2013.
Puhvel et al., Effect of fatty acids on the growth of Corynebacterium acnes in vitro. J Invest Dermatol. Jan. 1970;54(1):48-52.
Rivier et al., Peroxisome proliferator-activated receptor-alpha enhances lipid metabolism in a skin equivalent model. J Invest Dermatol. Apr. 2000;114(4):681-7.
Rohland et al., Cost-effective, high-throughput DNA sequencing libraries for multiplexed target capture. Genome Res. May 2012;22(5):939-46. doi: 10.1101/gr.128124.111. Epub Jan. 20, 2012.
Rosberg-Cody et al., Heterologous expression of linoleic acid isomerase from Propionibacterium acnes and anti-proliferative activity of recombinant trans-10, cis-12 conjugated linoleic acid. Microbiology. Aug. 2007;153(Pt 8):2483-90.
Ross et al., Phenotypic and genotypic characterization of antibiotic-resistant Propionibacterium acnes isolated from acne patients attending dermatology clinics in Europe, the U.S.A., Japan and Australia. Br J Dermatol. Feb. 2001;144(2):339-46.
Schnell et al., Prepeptide sequence of epidermin, a ribosomally synthesized antibiotic with four sulphide-rings. Nature. May 19, 1988;333(6170):276-8.

(56) References Cited

OTHER PUBLICATIONS

Scholz et al., Genome stability of Propionibacterium acnes: a comprehensive study of indels and homopolymeric tracts. Sci Rep. Feb. 9, 2016;6:20662. doi: 10.1038/srep20662.

Seidler et al., Meta-analysis comparing efficacy of benzoyl peroxide, clindamycin, benzoyl peroxide with salicylic acid, and combination benzoyl peroxide/clindamycin in acne. J Am Acad Dermatol. Jul. 2010;63(1):52-62. doi: 10.1016/j.jaad.2009.07.052. Epub May 21, 2010.

Sorenson et al., Mutagenesis of Propionibacterium acnes and analysis of two CAMP factor knock-out mutants. J Microbiol Methods. Nov. 2010;83(2):211-6. doi: 10.1016/j.mimet.2010.09.008. Epub Sep. 17, 2010.

Thielitz et al., A randomized investigator-blind parallel-group study to assess efficacy and safety of azelaic acid 15% gel vs. adapalene 0.1% gel in the treatment and maintenance treatment of female adult acne. J Eur Acad Dermatol Venereol. Apr. 2015;29(4):789-96. doi: 10.1111/jdv.12823. Epub Nov. 14, 2014.

Tripathi et al., Side effects of common acne treatments. Expert Opin Drug Saf. Jan. 2013;12(1):39-51. doi: 10.1517/14740338.2013.740456. Epub Nov. 20, 2012.

Van Nood et al., Duodenal infusion of donor feces for recurrent Clostridium difficile. N Engl J Med. Jan. 31, 2013;368(5):407-15. doi: 10.1056/NEJMoa1205037. Epub Jan. 16, 2013.

Wang et al., Characterization of the major bacterial-fungal populations colonizing dandruff scalps in Shanghai, China, shows microbial disequilibrium. Exp Dermatol. May 2015;24(5):398-400. doi: 10.1111/exd.12684.

Wang et al., *Staphylococcus epidermidis* in the human skin microbiome mediates fermentation to inhibit the growth of Propionibacterium acnes: implications of probiotics in acne vulgaris. Appl Microbiol Biotechnol. Jan. 2014;98(1):411-24. doi: 10.1007/s00253-013-5394-8. Epub Nov. 22, 2013.

Westerhof et al., Propionibacterium acnes and the pathogenesis of progressive macular hypomelanosis. Arch Dermatol. Feb. 2004;140(2):210-4.

Yu et al., Different Propionibacterium acnes Phylotypes Induce Distinct Immune Responses and Express Unique Surface and Secreted Proteomes. J Invest Dermatol. Nov. 2016;136(11):2221-2228. doi: 10.1016/j.jid.2016.06.615. Epub Jul. 1, 2016.

Yu et al., Typing of Propionibacterium acnes: a review of methods and comparative analysis. Br J Dermatol. 2015;172(5):1204-9. doi: 10.1111/bjd.13667. Epub Apr. 9, 2015.

Zhao, Genomics: The tale of our other genome. Nature. Jun. 17, 2010;465(7300):879-80. doi: 10.1038/465879a.

Zouboulis, Propionibacterium acnes and sebaceous lipogenesis: a love-hate relationship? J Invest Dermatol. Sep. 2009;129(9):2093-6. doi: 10.1038/jid.2009.190.

Zouboulis, Acne and sebaceous gland function. Clin Dermatol. Sep.-Oct. 2004;22(5):360-6.

Ahmed et al., High levels of 8-hydroxy-2'-deoxyguanosine appear in normal human epidermis after a single dose of ultraviolet radiation. Br J Dermatol. Feb. 1999;140(2):226-31. doi: 10.1111/j.1365-2133.1999.02653.x.

Allhorn et al., A novel enzyme with antioxidant capacity produced by the ubiquitous skin colonizer *Propionibacterium acnes*. Sci Rep. Nov. 2, 2016;6:36412. doi: 10.1038/srep36412.

Andersson et al., Common skin bacteria protect their host from oxidative stress through secreted antioxidant RoxP. Sci Rep. Mar. 5, 2019;9(1):3596. doi: 10.1038/s41598-019-40471-3.

Arthur, The glutathione peroxidases. Cell Mol Life Sci. Dec. 2000;57(13-14):1825-35. doi: 10.1007/pl00000664.

Cadet et al., Ultraviolet radiation-mediated damage to cellular DNA. Mutat Res. Apr. 1, 2005;571(1-2):3-17. doi: 10.1016/j.mrfmmm.2004.09.012. Epub Jan. 26, 2005.

Chen et al., The Human Oral Microbiome Database: a web accessible resource for investigating oral microbe taxonomic and genomic information. Database (Oxford). Jul. 6, 2010;2010:baq013. doi: 10.1093/database/baq013.

Dessinioti et al., The role of *Propionibacterium acnes* in acne pathogenesis: facts and controversies. Clin Dermatol. Jan.-Feb. 2010;28(1):2-7. doi: 10.1016/j.clindermatol.2009.03.012.

Eady et al., A distinct acne microbiome: fact or fiction? J Invest Dermatol. Sep. 2013;133(9):2294-5. doi: 10.1038/jid.2013.259. Epub Jun. 12, 2013.

Ertürk et al., Highly sensitive detection and quantification of the secreted bacterial benevolence factor RoxP using a capacitive biosensor: A possible early detection system for oxidative skin diseases. PLoS One. Mar. 1, 2018;13(3):e0193754. doi: 10.1371/journal.pone.0193754. PMID: 29494704.

Fitz-Gibbon et al., *Propionibacterium acnes* strain populations in the human skin microbiome associated with acne. J Invest Dermatol. Sep. 2013;133(9):2152-60. doi: 10.1038/jid.2013.21. Epub Jan. 21, 2013.

Foster et al., 651 Organic Osmolytes Improve Cell Volume Regulation of Aged Human Keratinocytes. J of Investigative Dermatology. May 2018; 138(5):S111. doi: 10.1016/j.jid.2018.03.660.

GENBANK Submission; NIH/NCBI Accession No. AAT83657.1. Bruggemann et al., Jan. 30, 2014. 1 page.

GENBANK Submission; NIH/NCBI Accession No. AE017283.1. Bruggemann et al., Jan. 30, 2014. 427 pages.

GENBANK Submission; NIH/NCBI Accession No. AFJ11206.1. Lood et al., Jun. 30, 2012. 1 page.

GENBANK Submission; NIH/NCBI Accession No. AFJ11207.1. Lood et al., Jun. 30, 2012. 1 page.

GENBANK Submission; NIH/NCBI Accession No. AFJ11208.1. Lood et al., Jun. 30, 2012. 1 page.

GENBANK Submission; NIH/NCBI Accession No. AFJ11209.1. Lood et al., Jun. 30, 2012. 1 page.

GENBANK Submission; NIH/NCBI Accession No. AFJ11210.1. Lood et al., Jun. 30, 2012. 1 page.

GENBANK Submission; NIH/NCBI Accession No. AFJ11211.1. Lood et al., Jun. 30, 2012. 1 page.

GENBANK Submission; NIH/NCBI Accession No. AFJ11212.1. Lood et al., Jun. 30, 2012. 1 page.

GENBANK Submission; NIH/NCBI Accession No. AFJ11213.1. Lood et al., Jun. 30, 2012. 1 page.

GENBANK Submission; NIH/NCBI Accession No. AFJ11214.1. Lood et al., Jun. 30, 2012. 1 page.

GENBANK Submission; NIH/NCBI Accession No. CP001977.1. Harkins et al., Dec. 11, 2013. 519 pages.

GENBANK Submission; NIH/NCBI Accession No. CP002409.1. Brzuszkiewicz et al., Jan. 30, 2014. 456 pages.

GENBANK Submission; NIH/NCBI Accession No. CP002815.1. Hunyadkurti et al., Jan. 30, 2014. 482 pages.

GENBANK Submission; NIH/NCBI Accession No. CP003084.1. Horvath et al., Jan. 30, 2014. 440 pages.

GENBANK Submission; NIH/NCBI Accession No. CP003195.1. Voros et al., Jan. 30, 2014. 463 pages.

GENBANK Submission; NIH/NCBI Accession No. CP003196.1. Voros et al., Jan. 30, 2014. 469 pages.

GENBANK Submission; NIH/NCBI Accession No. CP003197.1. Voros et al., Jan. 30, 2014. 465 pages.

GENBANK Submission; NIH/NCBI Accession No. CP003293.1. Fitz-Gibbon et al., Jan. 31, 2014. 415 pages.

GENBANK Submission; NIH/NCBI Accession No. CP003877.1. Minegishi et al., Jan. 31, 2014. 481 pages.

GENBANK Submission; NIH/NCBI Accession No. CP006032.1. Nagy et al., Oct. 1, 2014. 542 pages.

GENBANK Submission; NIH/NCBI Accession No. CP012350.1. Scholz et al., Sep. 22, 2017. 556 pages.

GENBANK Submission; NIH/NCBI Accession No. CP012351.1. Scholz et al., Sep. 22, 2017. 560 pages.

GENBANK Submission; NIH/NCBI Accession No. CP012352.1. Scholz et al., Sep. 22, 2017. 562 pages.

GENBANK Submission; NIH/NCBI Accession No. CP012353.1. Scholz et al., Sep. 22, 2017. 548 pages.

GENBANK Submission; NIH/NCBI Accession No. CP012354.1. Scholz et al., Sep. 22, 2017. 553 pages.

GENBANK Submission; NIH/NCBI Accession No. CP012355.1. Scholz et al., Sep. 22, 2017. 554 pages.

(56) References Cited

OTHER PUBLICATIONS

GENBANK Submission; NIH/NCBI Accession No. CP012647.1. Kook et al., Oct. 11, 2017. 546 pages.
GENBANK Submission; NIH/NCBI Accession No. CP013693.1. Alexeeva et al., Oct. 17, 2017. 520 pages.
GENBANK Submission; NIH/NCBI Accession No. CP023676.1. Tang et al., Apr. 2, 2018. 588 pages.
GENBANK Submission; NIH/NCBI Accession No. CP031442.1. Kook et al., Aug. 14, 2018. 606 pages.
GENBANK Submission; NIH/NCBI Accession No. JN051668.1. Lood et al., Jun. 30, 2012. 1 page.
GENBANK Submission; NIH/NCBI Accession No. NC_006085.1. Bruggemann et al., Mar. 29, 2017. 1 page.
GENBANK Submission; NIH/NCBI Accession No. NC_014039.1. Harkins et al., Mar. 30, 2017. 2 pages.
GENBANK Submission; NIH/NCBI Accession No. NC_016511.1. Voros et al., Jan. 11, 2018. 1 page.
GENBANK Submission; NIH/NCBI Accession No. NC_016512.1. Voros et al., Jan. 11, 2018. 1 page.
GENBANK Submission; NIH/NCBI Accession No. NC_016516.1. Voros et al., Jan. 11, 2018. 1 page.
GENBANK Submission; NIH/NCBI Accession No. NC_017534.1. Brzuszkiewicz et al., Mar. 30, 2017. 2 pages.
GENBANK Submission; NIH/NCBI Accession No. NC_017535.1. Hunyadkurti et al., Mar. 30, 2017. 1 page.
GENBANK Submission; NIH/NCBI Accession No. NC_017550.1. Horvath et al., Jan. 11, 2018. 2 pages.
GENBANK Submission; NIH/NCBI Accession No. NC_018707.1. Minegishi et al., Mar. 30, 2017. 1 page.
GENBANK Submission; NIH/NCBI Accession No. NC_021085.1. Fitz-Gibbon et al., Apr. 1, 2017. 1 page.
GENBANK Submission; NIH/NCBI Accession No. NZ_CP006032. 1. Nagy et al., Apr. 2, 2017. 2 pages.
GENBANK Submission; NIH/NCBI Accession No. NZ_CP012350. 1. Scholz et al., Sep. 25, 2017. 2 pages.
GENBANK Submission; NIH/NCBI Accession No. NZ_CP012351. 1. Scholz et al., Sep. 25, 2017. 2 pages.
GENBANK Submission; NIH/NCBI Accession No. NZ_CP012352. 1. Scholz et al., Sep. 25, 2017. 2 pages.
GENBANK Submission; NIH/NCBI Accession No. NZ_CP012353. 1. Scholz et al., Sep. 25, 2017. 2 pages.
GENBANK Submission; NIH/NCBI Accession No. NZ_CP012354. 1. Scholz et al., Sep. 25, 2017. 2 pages.
GENBANK Submission; NIH/NCBI Accession No. NZ_CP012355. 1. Scholz et al., Sep. 25, 2017. 2 pages.
GENBANK Submission; NIH/NCBI Accession No. NZ_CP012647. 1. Kook et al., Oct. 18, 2017. 2 pages.
GENBANK Submission; NIH/NCBI Accession No. NZ_CP013693. 1. Alexeeva et al., Oct. 23, 2017. 2 pages.
GENBANK Submission; NIH/NCBI Accession No. NZ_CP023676. 1. Tang et al., Apr. 4, 2018. 2 pages.
GENBANK Submission; NIH/NCBI Accession No. NZ_CP031442. 1. Kook et al., Aug. 16, 2018. 2 pages.
Guell et al., Long lasting effect of skin microbiome modulation induced by probiotic solution application. Presented at Barcelona Debates on Human Microbiome, Jun. 30, 2016-Jul. 1. 1pg. Poster.
Gutteridge et al., The deoxyribose assay: an assay both for 'free' hydroxyl radical and for site-specific hydroxyl radical production. Biochem J. Aug. 1, 1988;253(3):932-3. doi: 10.1042/bj2530932.
Holland et al., Proteomic identification of secreted proteins of *Propionibacterium acnes*. BMC Microbiol. Aug. 27, 2010;10:230. doi: 10.1186/1471-2180-10-230.
Holmberg et al., Biofilm formation by *Propionibacterium acnes* is a characteristic of invasive isolates. Clin Microbiol Infect. Aug. 2009;15(8):787-95. doi: 10.1111/j.1469-0691.2009.02747.x. Epub Apr. 23, 2009.
Johnson et al., Cell wall composition and deoxyribonucleic acid similarities among the anaerobic coryneforms, classical propionibacteria, and strains of *Arachnia propionica*. J Bacteriol. Mar. 1972;109(3):1047-66. doi: 10.1128/jb.109.3.1047-1066.1972.
Kadam et al. Role of oxidative stress in various stages of psoriasis. Indian J Clin Biochem. Oct. 2010;25(4):388-92. doi: 10.1007/s12291-010-0043-9. Epub Sep. 24, 2010.
Karoglan et al, Segmental angeordnete basaloide follikuläre Hamartome mit zerebralen Eisenablagerungen als neue Variante des Happle-Tinschert Syndroms. Journal of the German Society of Dermatology. Apr. 25, 2017; 15(S1): #P094. doi.org/10.1111/ddg.13213. Abstract only.
Karoglan et al., Direct modulation of the Cutibacterium strain population as novel tool in skin microbiome research. 45th Annual Meeting of the ADF in Zurich, Switzerland, Mar. 7-10, 2018. #P061. Abstract only.
Karoglan et al., Direct modulation of the skin microbiome as new experimental tool for skin diseases. 44th Annual Meeting of the ADF in Gottingen, Germany, Mar. 8, 2017. 1pg. Abstract only.
Liew-Littorin et al., Clonal diversity of *Cutibacterium acnes* (formerly *Propionibacterium acnes*) in prosthetic joint infections. Anaerobe. Oct. 2019;59:54-60. doi: 10.1016/j.anaerobe.2019.04.011. Epub May 7, 2019.
Lin et al., A combination of improved differential and global RNA-seq reveals pervasive transcription initiation and events in all stages of the life-cycle of functional RNAs in *Propionibacterium acnes*, a major contributor to wide-spread human disease. BMC Genomics. Sep. 14, 2013;14:620. doi: 10.1186/1471-2164-14-620.
Lodes et al., Variable expression of immunoreactive surface proteins of *Propionibacterium acnes*. Microbiology. Dec. 2006;152(Pt 12):3667-3681. doi: 10.1099/mic.0.29219-0.
Lomholt et al., Population genetic analysis of *Propionibacterium acnes* identifies a subpopulation and epidemic clones associated with acne. PLoS One. Aug. 19, 2010;5(8):e12277. doi: 10.1371/journal.pone.0012277.
Mcdowell et al., A new phylogenetic group of *Propionibacterium acnes*. J Med Microbiol. Feb. 2008;57(Pt 2):218-224. doi: 10.1099/jmm.0.47489-0.
Mcdowell et al., An expanded multilocus sequence typing scheme for *Propionibacterium acnes*: investigation of 'pathogenic', 'commensal' and antibiotic resistant strains. PLoS One. 2012;7(7):e41480. doi: 10.1371/journal.pone.0041480. Epub Jul. 30, 2012.
Mcdowell et al., *Propionibacterium acnes* types I and II represent phylogenetically distinct groups. J Clin Microbiol. Jan. 2005;43(1):326-34. doi: 10.1128/JCM.43.1.326-334.2005. Erratum in: J Clin Microbiol. Feb. 2010;48(2):681.
Nicholson et al., Identification and inhibition of the ICE/CED-3 protease necessary for mammalian apoptosis. Nature. Jul. 6, 1995;376(6535):37-43. doi: 10.1038/376037a0.
O'Neill et al., Distinct *Cutibacterium acnes* strains isolated from lesional and non-lesional regions of acne promote differential immune responses. J of Investigative Dermatology, May 2018, vol. 138, No. 5, Supplement 1 pp. S173. Abstract No. 1023.
Patzold, Long lasting effect of skin microbiome modulation induced by topical probiotic solution application. Targeting Microbiota, Paris, France. Oct. 17, 2016. 13 pgs. Presentation.
Patzold, Long lasting effect of skin microbiome modulation induced by topical probiotic solution application. Barcelona Debates on Human Microbiome, Jul. 1, 2016. 15 pgs. Presentation.
Perry et al., A, *Propionibacterium acnes*: infection beyond the skin. Expert Rev Anti Infect Ther. Dec. 2011;9(12):1149-56. doi: 10.1586/eri.11.137.
Sander et al., Oxidative stress in malignant melanoma and non-melanoma skin cancer. Br J Dermatol. May 2003;148(5):913-22. doi: 10.1046/j.1365-2133.2003.05303.x.
Scholz et al., A novel high-resolution single locus sequence typing scheme for mixed populations of *Propionibacterium acnes* in vivo. PLoS One. Aug. 11, 2014;9(8):e104199. doi: 10.1371/journal.pone.0104199. eCollection 2014.
Shaheen et al., A microbial aetiology of acne: what is the evidence? Br J Dermatol. Sep. 2011;165(3):474-85. doi: 10.1111/j.1365-2133.2011.10375.x.
Solovyev at al., Automatic Annotation of Microbial Genomes and Metagenomic Sequences. In Metagenomics and its Applications in Agriculture, Biomedicine and Environmental Studies. 2011 Li (Ed). 18 pages.

(56) References Cited

OTHER PUBLICATIONS

Valanne et al., CAMP factor homologues in *Propionibacterium acnes*: a new protein family differentially expressed by types I and II. Microbiology. May 2005;151(Pt 5):1369-1379. doi: 10.1099/mic.0.27788-0.

Valavanidis et al., 8-hydroxy-2'-deoxyguanosine (8-OHdG): A critical biomarker of oxidative stress and carcinogenesis. J Environ Sci Health C Environ Carcinog Ecotoxicol Rev. Apr. 2009;27(2):120-39. doi: 10.1080/10590500902885684.

Karoglan et al., Direct modulation of the skin microbiome as new experimental tool for skin diseases. 44th Annual Meeting of the ADF in Gottingen, Germany, Mar. 9-11, 2017. 1pg. Poster.

* cited by examiner

| COMPOUND / STRAIN | GLYCOLIC ACID | | | | | | | | | | |
|---|---|---|---|---|---|---|---|---|---|---|---|
| | (CONCENTRATION, mM), +: INHIBITION; -: VISIBLE GROWTH, n=2 | | | | | | | | | | |
| | 180 | 60 | 18 | 6 | 1.8 | 0.6 | 0.18 | 0.06 | 0.018 | 0.006 | 0.0018 |
| ATCC 11827 | +/+ | +/+ | +/+ | -/- | -/- | -/- | -/- | -/- | -/- | -/- | -/- |
| ATCC 29399 | +/+ | +/+ | -/- | -/- | -/- | -/- | -/- | -/- | -/- | -/- | -/- |
| ATCC 6919 | +/+ | +/+ | +/+ | -/- | -/- | -/- | -/- | -/- | -/- | -/- | -/- |

| COMPOUND / STRAIN | HYALURONIC ACID | | | | | | | | | | |
|---|---|---|---|---|---|---|---|---|---|---|---|
| | (CONCENTRATION, nM), +: INHIBITION; -: VISIBLE GROWTH, n=2 | | | | | | | | | | |
| | 60 | 20 | 6 | 2 | 0.6 | 0.2 | 0.06 | 0.02 | 0.006 | 0.002 | 0.0006 |
| ATCC 11827 | -/- | -/- | -/- | -/- | -/- | -/- | -/- | -/- | -/- | -/- | -/- |
| ATCC 29399 | -/- | -/- | -/- | -/- | -/- | -/- | -/- | -/- | -/- | -/- | -/- |
| ATCC 6919 | -/- | -/- | -/- | -/- | -/- | -/- | -/- | -/- | -/- | -/- | -/- |

| COMPOUND / STRAIN | LACTIC ACID | | | | | | | | | | |
|---|---|---|---|---|---|---|---|---|---|---|---|
| | (CONCENTRATION, %), +: INHIBITION; -: VISIBLE GROWTH, n=2 | | | | | | | | | | |
| | 2 | 0.6 | 0.2 | 0.06 | 0.02 | 0.006 | 0.002 | 0.0006 | 0.0002 | 0.00006 | 0.00002 |
| ATCC 11827 | +/+ | +/+ | +/+ | -/- | -/- | -/- | -/- | -/- | -/- | -/- | -/- |
| ATCC 29399 | +/+ | +/+ | -/- | -/- | -/- | -/- | -/- | -/- | -/- | -/- | -/- |
| ATCC 6919 | +/+ | +/+ | +/+ | -/- | -/- | -/- | -/- | -/- | -/- | -/- | -/- |

| COMPOUND / STRAIN | SALICYLIC ACID | | | | | | | | | | |
|---|---|---|---|---|---|---|---|---|---|---|---|
| | (CONCENTRATION, µM), +: INHIBITION; -: VISIBLE GROWTH, n=2 | | | | | | | | | | |
| | 6000 | 2000 | 600 | 200 | 60 | 20 | 6 | 2 | 0.6 | 0.2 | 0.0600 |
| ATCC 11827 | -/- | -/- | -/- | -/- | -/- | -/- | -/- | -/- | -/- | -/- | -/- |
| ATCC 29399 | -/- | -/- | -/- | -/- | -/- | -/- | -/- | -/- | -/- | -/- | -/- |
| ATCC 6919 | -/- | -/- | -/- | -/- | -/- | -/- | -/- | -/- | -/- | -/- | -/- |

| COMPOUND / STRAIN | CLINDAMYCIN (GLYCOLIC ACID) | | | | | | | | | | |
|---|---|---|---|---|---|---|---|---|---|---|---|
| | (CONCENTRATION, µg/mL), +: INHIBITION; -: VISIBLE GROWTH, n=2 | | | | | | | | | | |
| | 8 | 4 | 2 | 1 | 0.5 | 0.25 | 0.125 | 0.0625 | 0.0313 | 0.0156 | 0.0780 |
| ATCC 11827 | +/+ | +/+ | +/+ | +/+ | +/+ | +/+ | +/+ | +/+ | -/- | -/- | -/- |
| ATCC 29399 | +/+ | +/+ | +/+ | +/+ | +/+ | +/+ | +/+ | -/- | -/- | -/- | -/- |
| ATCC 6919 | +/+ | +/+ | +/+ | +/+ | +/+ | +/+ | +/+ | -/- | -/- | -/- | -/- |

FIG. 8

| SUBJECT | AGE | SEX | REDUCTION IN LESIONS | | SAME STATE OF LESIONS | IRRITATION - NO +++ HIGH |
|---|---|---|---|---|---|---|
| | | | WEEK1 (DAY 7) | WEEK3 (DAY 21) | | |
| 1 | 16 | F | YES | | | + |
| 2 | 14 | M | YES | | | - |
| 3 | 21 | M | | YES | | ++ |
| 4 | 20 | M | YES | | | - |
| 5 | 15 | F | | YES | YES | - |
| 6 | 16 | F | | YES | | +++ |
| 7 | 18 | M | | YES | | + |
| 8 | 23 | M | | YES | | - |
| 9 | 25 | F | YES | | YES | + |
| 10 | 19 | M | | | YES | - |

FIG. 9

SEQUENCE LISTING

```
<160> NUMBER OF SEQ ID NOS: 80

<210> SEQ ID NO 1
<211> LENGTH: 484
<212> TYPE: DNA
<213> ORGANISM: Propionibacterium acnes

<400> SEQUENCE: 1
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctaccttg tcagacccag gacgatgggt     180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcctta ttagggcaag cggtgccagt agcagaatat     360
gtcacctcaa caactcgatc caccctgcc cattacatgg gtaacatatc catggaggtt    420
cgatgtatac tcgaggatac agtcgtccat cacgcccgcc tacataccca ttacatcagc    480
atag                                                                 484

<210> SEQ ID NO 2
<211> LENGTH: 484
<212> TYPE: DNA
<213> ORGANISM: Propionibacterium acnes

<400> SEQUENCE: 2
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctaccttg tcagacccag gacgatgggt     180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgattctg gattcctatt gtcgcctta ttagggcaag cggtgccagt agcagaatat     360
```

```
gtcacctcaa caactcgatc caccectgcc cattacatgg gtaacatatc catggaggtt    420
cgatgtatac tcgaggatac agtcgtccat cacgcccgcc tacataccca ttacatcagc    480
atag                                                                  484

<210> SEQ ID NO 3
<211> LENGTH: 484
<212> TYPE: DNA
<213> ORGANISM: Propionibacterium acnes

<400> SEQUENCE: 3
gttgcacacc aggggggtcaa cttggcgtcc tcagttcaaa attgattcaa actaacagtt    60
ccatgtcggg aaacagcacc aggaagctcg tgacatatgg tctttcattg cgagaaacat    120
cttacttatg tacatttcta agctatagcg tctaccettg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccttc ttagggcaag cggtgccagt agcagaatat    360
gtcacctcaa taactcgatc caccectgcc cattacatgg gtaacatatc catggaggtt    420
cgatgtatac tcgaggatac agtcgtccat cacgcccgcc tacataccca ttacatcagc    480
atag                                                                  484

<210> SEQ ID NO 4
<211> LENGTH: 484
<212> TYPE: DNA
<213> ORGANISM: Propionibacterium acnes

<400> SEQUENCE: 4
gttgcacacc aggggggtcaa cttggcgtcc tcagttcaaa attgattcaa actaacagtt    60
ccatgtcggg aaacagcacc aggaagctcg tgacatatgg tctttcattg cgagaaacat    120
cttacttatg tacatttcta agctatagcg tctaccettg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccttc ttagggcaag cggtgccagt agcagaatat    360
gtcacctcaa caactcgatc caccectgcc cattacatgg gtaacatatc catggaggtt    420
cgatgtatac tcgaggatac agtcgtccat cacgcccgcc tacataccca ttacatcagc    480
atag                                                                  484

<210> SEQ ID NO 5
<211> LENGTH: 484
<212> TYPE: DNA
<213> ORGANISM: Propionibacterium acnes

<400> SEQUENCE: 5
gttgcacacc aggggggtcaa cttggcgtcc tcagttcaaa attgattcaa actaacagtt    60
ccatgccggg aaacagcacc aggaagctcg tgacatatcg tctttcattg cgagaaacat    120
cttacttatg tacatttcta agctatagcg tctaccettg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccttc ttagggcaag cggtgccagt agcagaatat    360
gtcacctcaa caactcgatc caccectgcc cattacatgg gtaacatatc catggaggtt    420
```
cgatgtatac tcgaggatac agtcgtccat cacgcccgcc tacatacccca ttacatcagc      480 atag                                                                    484

<210> SEQ ID NO 6
<211> LENGTH: 484
<212> TYPE: DNA
<213> ORGANISM: Propionibacterium acnes

<400> SEQUENCE: 6
gttgcacacc aggggtcaa cttggcgtcc tcagttcaaa attgattcaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gattcctatt gtcgccctta ttagggcaag cggtgccagt agcagaatat     360
gtcacctcaa caactcgatc caccctgcc cattacatgg gtaacatatc catggaggtt     420
cgatgtatac tcgaggatac agtcgtccat cacgcccgcc tacatacccca ttacatcagc      480 atat                                                                    484

<210> SEQ ID NO 7
<211> LENGTH: 484
<212> TYPE: DNA
<213> ORGANISM: Propionibacterium acnes

<400> SEQUENCE: 7
gttgcacacc aggggtcaa cttggcgtcc tcagttcaaa attgattcaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatgggt     180
gtcacatctc ctttctagtc aacctaagag aggaggaaat gccgcgatat atgttccacc     240
ctgccatcac gaaggccacc acaatctatc ccagaacagc cggcacttca ctcacgatgc     300
cccgattctg gattcctatt gtcgccctta ttagggcaag cggtgccagt agcagaatat     360
gtcacctcaa caactcgatc caccctgcc cattacatgg gtaacatatc catggaggtt     420
cgatgtatac tcgaggatac agtcgtccat cacgcccgcc tacatacccca ttacatcagc      480 atag                                                                    484

<210> SEQ ID NO 8
<211> LENGTH: 484
<212> TYPE: DNA
<213> ORGANISM: Propionibacterium acnes

<400> SEQUENCE: 8
gttgcacacc aggggtcaa cttggcgtcc tcagttcaaa attgattcaa actaacagtt       60
ccatgtcggg aaacagcacc aggaagctcg tgacatatcg cctttcattg cgagaaacat      120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gattcctatt gtcgccctta ttagggcaag cggtgccagt agcagaatat     360
gtcacctcaa caactcgatc caccctgcc cattacatgg gtaacatatc catggaggtt     420

```
cgatgtatac tcgaggatac agtcgtccat cacgcccgcc tacatacccca ttacatcagc    480 atag                                                                 484

<210> SEQ ID NO 9
<211> LENGTH: 484
<212> TYPE: DNA
<213> ORGANISM: Propionibacterium acnes

<400> SEQUENCE: 9
gttgcacacc aggggtcaa cttggcgtcc tcagttcaaa attgattcaa actaacagtt      60
ccatgccggg aaacagcacc aggaagctcg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
ctgtcatcat gaaggccacc acaatctatc ccagaacagc cggcacttca ctcacgatgc    300
cccgatgctg gattcctatt gtcgcccctta ttagggcaag cggtgccagt agcagaaatat  360 gtcacctcaa caactcgatc caccccctgcc cattacatgg gtaacatatc catggaggtt    420
cgatgtatac tcgaggatac agtcgtccat cacgcccgcc tacatacccca ttacatcagc   480 atag                                                                 484

<210> SEQ ID NO 10
<211> LENGTH: 484
<212> TYPE: DNA
<213> ORGANISM: Propionibacterium acnes

<400> SEQUENCE: 10
gttgcacacc aggggtcaa cttggcgtcc tcagttcaaa attgattcaa actaacagtt      60
ccatgccggg aaacagcacc aggaagctcg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccctta ttagggcaag cggtgccagt agcagaaatat  360 gtcacctcaa caactcgatc taccccctgcc cattacatgg gtaacatatc catggaggtt    420
cgatgtatac tcgaggatac agtcgtccat cacgcccgcc tacatacccca ttacatcagc   480 atag                                                                 484

<210> SEQ ID NO 11
<211> LENGTH: 484
<212> TYPE: DNA
<213> ORGANISM: Propionibacterium acnes

<400> SEQUENCE: 11
gttgcacacc aggggtcaa cttggcgtcc tcagttcaaa attgattcaa actaacagtt      60
ccatgccggg aaacagcacc aggaagcccg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccctta ttagggcaag cggtgccagt agcagaaatat  360 gtcacctcaa caactcgatc caccccctgcc cattacatgg gtaacatatc catggaggtt    420
cgatgtatac tcgaggatac agtcgtccat cacgcccgcc tacatacccca ttacatcagc   480
```

| | |
|---|---:|
| atag | 484 |

<210> SEQ ID NO 12
<211> LENGTH: 484
<212> TYPE: DNA
<213> ORGANISM: Propionibacterium acnes

<400> SEQUENCE: 12

| | |
|---|---:|
| gttgcacacc agggggtcaa cttggcgtcc tcagttcaaa attgattcaa actaacagtt | 60 |
| ccatgccggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatctc ctttctagtc aacctaagag aggaggaaat gccgcgatat atattccacc | 240 |
| ctgtcatcac gaaggccacc acaatctatc ccagaacagc cggcacttca ctcacgatgc | 300 |
| cccgatgctg gattcctatt gtcgcccctta ttagggcaag cggtgccagt agcagaatat | 360 |
| gtcacctcaa caactcgatc cacccctgcc cattacatgg gtaacatatc catggaggtt | 420 |
| cgatgtatac tcgaggatac agtcgtccat cacgcccgcc tacatacccca ttacatcagc | 480 |
| atag | 484 |

<210> SEQ ID NO 13
<211> LENGTH: 484
<212> TYPE: DNA
<213> ORGANISM: Propionibacterium acnes

<400> SEQUENCE: 13

| | |
|---|---:|
| gttgcacacc agggggtcaa cttggcgtcc tcagttcaaa attgattcaa actaacagtt | 60 |
| ccatgtcggg aaacagcacc aggaagctgg tgacatatcg tctttcattg cgagaaacat | 120 |
| cttacttatg tacatttcta agctatagcg tctacccttg tcagacccag gacgatgggt | 180 |
| gtcacatctc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcaa caactcgatc caccccctgcc cattacatgg gtaacatatc catggaggtt | 420 |
| cgatgtatac tcgaggatac agtcgtccat cacgcccgcc tacatacccca ttacatcagc | 480 |
| atag | 484 |

<210> SEQ ID NO 14
<211> LENGTH: 484
<212> TYPE: DNA
<213> ORGANISM: Propionibacterium acnes

<400> SEQUENCE: 14

| | |
|---|---:|
| gttgcacacc agggggtcaa cttggcgttt tcagttcaaa attgattcaa actaacagtt | 60 |
| ccatgccggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatctc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcaa caactcgatc caccccctgcc cattacatgg gtaacatatc catggaggtt | 420 |
| cgatgtatac tcgaggatac agtcgtccat cacgcccgcc tacatacccca ttacatcagc | 480 |

```
atag                                                                    484

<210> SEQ ID NO 15
<211> LENGTH: 484
<212> TYPE: DNA
<213> ORGANISM: Propionibacterium acnes

<400> SEQUENCE: 15
gttgcacacc aggggggtcaa cttggcgtcc tcagttcaaa attgattcaa actaacagtt      60
ccatgccggg aaacagtacc aggaagctcg tgacatatcg tctttcattg cgagaaacat     120
cttacttatg tacatttcta agctatagcg tctaccccttg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgccctta ttagggcaag cggtgccagt agcagaatat    360
gtcacctcaa caactcgatc caccccctgcc cattacatgg gtaacatatc catggaggtt   420
cgatgtatac tcgaggatac agtcgtccat cacgcccgcc tacataccca ttacatcagc    480
atag                                                                  484

<210> SEQ ID NO 16
<211> LENGTH: 484
<212> TYPE: DNA
<213> ORGANISM: Propionibacterium acnes

<400> SEQUENCE: 16
gttgcacacc aggggggtcaa cttggcgtcc tcagttcaaa attgattcaa actaacagtt     60
ccatgccggg aaacagcacc aggaagctcg tgacatatcg tctttcattg cgagaaacat    120
cttacttatg tacatttcta agctatagcg tctaccccttg tcagacccag gacgatgggt   180
gtcacatctc ctttctagtc aacctaagag aggaggaaat gccgcgatat atgttccacc   240
ctgtcatcac gaaggccacc acaatctatc ccagaacagc cggcacttca ctcacgatgc   300
cccgatgctg gattcctatt gtcgccctta ttagggcaag cggtgccagt agcagaatat   360
gtcacctcaa caactcgatc caccccctgcc cattacatgg gtaacatatc catggaggtt  420
cgatgtatac tcgaggatac agtcgtccat cacgcccgcc tacataccca ttacatcagc   480
atag                                                                  484

<210> SEQ ID NO 17
<211> LENGTH: 484
<212> TYPE: DNA
<213> ORGANISM: Propionibacterium acnes

<400> SEQUENCE: 17
gttgcacacc aggggggtcaa cttggcgtcc tcagttcaaa attgattcaa actaacagtt     60
ccatgtcggg aaacagcacc aggaagctcg tgacatatcg tctttcattg cgagaaacat   120
cttacttatg tacatttcta agctatagcg tctaccccttg tcagacccag gacgatgggt  180
gtcacatctc ctttctagtc aacctaagag aggaggaaat gccgcgatat atgttccacc  240
ctgtcatcac gaaggccacc acaatctatc ccagaacagc cggcacttca ctcacgatgc  300
cccgatgctg gattcctatt gtcgccctta ttagggcaag cggtgccggt agcagaatat  360
gtcacctcaa caactcgatc caccccctgcc cattacatgg gtaacatatc catggaggtt 420
cgatgtatac tcgaggatac agtcgtccat cacgcccgcc tacataccca ttacatcagc  480
atag                                                                  484
```

<210> SEQ ID NO 18
<211> LENGTH: 484
<212> TYPE: DNA
<213> ORGANISM: Propionibacterium acnes

<400> SEQUENCE: 18

| gttgcacacc aggggtcaa cttggcgtcc tcagttcaaa attgattcaa actaacagtt | 60 |
| ccatgtcggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatctc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgccctta ttagggcaag cggtgccagt agcagaatat | 360 |
| gccacctcaa caactcgatc caccccctgcc cattacatgg gtaacatatc catggaggtt | 420 |
| cgatgtatac tcgaggatac agtcgtccat cacgcccgcc tacatacccca ttacatcagc | 480 |
| atag | 484 |

<210> SEQ ID NO 19
<211> LENGTH: 484
<212> TYPE: DNA
<213> ORGANISM: Propionibacterium acnes

<400> SEQUENCE: 19

| gttgcacacc aggggtcaa cttggcgtcc tcagttcaaa attgattcaa actaacagtt | 60 |
| ccatgtcggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatctc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcaa caactcgatc gaccccctgcc cattacatgg gtaacatatc catggaggtt | 420 |
| cgatgtatac tcgaggatac agtcgtccat cacgcccgcc tacatacccca ttacatcagc | 480 |
| atag | 484 |

<210> SEQ ID NO 20
<211> LENGTH: 484
<212> TYPE: DNA
<213> ORGANISM: Propionibacterium acnes

<400> SEQUENCE: 20

| gttgcacacc aggggtcaa cttggcgtcc tcagttcaaa attgattcaa actaacagtt | 60 |
| ccatgtcggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatctc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt ttcgccctta ttagggcaag cggtgccagt agcagaatat | 360 |
| gtcacctcaa caactcgatc caccccctgcc cattacatgg gtaacatatc catggaggtt | 420 |
| cgatgtatac tcgaggatac agtcgtccat cacgcccgcc tacatacccca ttacatcagc | 480 |
| atag | 484 |

<210> SEQ ID NO 21
<211> LENGTH: 484
<212> TYPE: DNA
<213> ORGANISM: Propionibacterium acnes

<400> SEQUENCE: 21

| | | |
|---|---|---|
| gttgcacacc aggggtcaa cttggcgtcc tcagttcaaa attgattcaa actaacagtt | 60 |
| ccatgccggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatctc ctttctagtc aacctaagag aggaggaaat gccgcgatat atgttccacc | 240 |
| ctgtcatcac gaaggccacc acaatctatc ccagaacagc cggcacttca ctcacaatgc | 300 |
| cccgatgctg gattcctatt gtcgccctta ttagggcaag cggtgccagt agcagaatat | 360 |
| gtcacctcaa caactcgatc cacccctgcc cattacatgg gtaacatatc catggaggtt | 420 |
| cgatgtatac tcgaggatac agtcgtccat cacgcccgcc tacataccca ttacatcagc | 480 |
| atag | 484 |

<210> SEQ ID NO 22
<211> LENGTH: 484
<212> TYPE: DNA
<213> ORGANISM: Propionibacterium acnes

<400> SEQUENCE: 22

| | | |
|---|---|---|
| gttgcacacc aggggtcaa cttggcgtcc tcagttcaaa attgattcaa actaacagtt | 60 |
| ccatgccggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatctc ctttctggtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcaa caactcgatc cacccctgcc cattacatgg gtaacatatc catggaggtt | 420 |
| cgatgtatac tcgaggatac agtcgtccat cacgcccgcc tacataccca ttacatcagc | 480 |
| atag | 484 |

<210> SEQ ID NO 23
<211> LENGTH: 484
<212> TYPE: DNA
<213> ORGANISM: Propionibacterium acnes

<400> SEQUENCE: 23

| | | |
|---|---|---|
| gttgcacacc aggggtcaa cttggcgtcc tcagttcaaa attgattcaa actaacagtt | 60 |
| ccatgtcggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatctc ctttctagtc aacccaagag aggaggaaat gccgcgatat atgttccacc | 240 |
| ctgtcatcac gaaggccacc acaatctatc ccagaacagc cggcacttca ctcacgatgc | 300 |
| cccgattctg gattcctatt gtcgccctta ttagggcaag cggtgccagt agcagaatat | 360 |
| gtcacctcaa caactcgatc cacccctgcc cattacatgg gtaacatatc catggaggtt | 420 |
| cgatgtatac tcgaggatac agtcgtccat cacgcccgcc tacataccca ttacatcagc | 480 |
| atag | 484 |

<210> SEQ ID NO 24
<211> LENGTH: 484
<212> TYPE: DNA
<213> ORGANISM: Propionibacterium acnes

<400> SEQUENCE: 24

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacatccc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccctta ttagggcaag cggtgccagt agcagaatat    360
gtcacctcag caactcgatc caccctgcc cattacatgg gtaacatatc catggaggtt    420
cgatgtatac tcgaggatac agtcgtccat cacgcccgcc tacatacccca ttacatcagc    480
atag                                                                  484
```

<210> SEQ ID NO 25
<211> LENGTH: 484
<212> TYPE: DNA
<213> ORGANISM: Propionibacterium acnes

<400> SEQUENCE: 25

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacatccc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccctta ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacatacccca ttacatcagc    480
atag                                                                  484
```

<210> SEQ ID NO 26
<211> LENGTH: 484
<212> TYPE: DNA
<213> ORGANISM: Propionibacterium acnes

<400> SEQUENCE: 26

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagacccat gacgatgggt    180
gtcacatccc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccctta ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacatacccca ttacatcagc    480
atag                                                                  484
```

<210> SEQ ID NO 27

<211> LENGTH: 484
<212> TYPE: DNA
<213> ORGANISM: Propionibacterium acnes

<400> SEQUENCE: 27

```
gttgcacacc aggggtcaa cttggcgtcc ttagttcaaa attgattcaa actaacagtt      60
ccatgtcggg aaacagcacc aggaagctcg tgacatatcg tctttcattg cgagaaacat    120
cttacttatg tacatttcta agctatagcg tctaccttg tcagacccag gacgatgggt    180
gtcacatccc ctttctagtc aacctaagag aggaggaaat gccgcgatat atgttccacc    240
ctgtcatcac gaaggccacc acaatctatc cagaacagc cggcacttca ctcacgatgc    300
cccgatgctg gattcctatt gtcgcccta ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacatacccca ttacatcagc    480
atag                                                                  484
```

<210> SEQ ID NO 28
<211> LENGTH: 484
<212> TYPE: DNA
<213> ORGANISM: Propionibacterium acnes

<400> SEQUENCE: 28

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctaccctg tcagacccag gacgatgggt    180
gtcacatccc ctttctagtc aacctaagag aggaggaaat gccgcgatat atgttccacc    240
ctgtcatcac gaaggccacc acaatctatc cagaacagc cggcacttca ctcacgatgc    300
cccgatgctg gattcctatt gtcgcccta ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacatacccca ttacatctgc    480
atag                                                                  484
```

<210> SEQ ID NO 29
<211> LENGTH: 484
<212> TYPE: DNA
<213> ORGANISM: Propionibacterium acnes

<400> SEQUENCE: 29

```
gttgcacacc aggggtcaa cttggcgtcc tcagttcaaa attgattcaa actaacagtt      60
ccatgtcggg aaacagcacc aggaaactcg tgacatatcg tctttcattg cgagaaacat    120
cttacttatg tacatttcta agctatagcg tctaccctg tcagacccag gacgatgggt    180
gtcacatccc ctttctagtc aacctaagag aggaggaaat gccgcgatat atgttccgcc    240
ctgtcatcac gaagaccacc acaatctatc cagaacagc cggcacttca ctcacgatgc    300
cccgatgctg gattcctatt gtcgcccta ttagggcaag cggtgccagt agcagaatat    360
gtcacctcaa caactcgatc caccctgcc cattacatgg gtaacatatc catggaggtt    420
cgatgtatac ttgaggatac agtcgtccat cacgcccacc tacataccca ttacatcagc    480
atag                                                                  484
```

<210> SEQ ID NO 30
<211> LENGTH: 484

<212> TYPE: DNA
<213> ORGANISM: Propionibacterium acnes

<400> SEQUENCE: 30

```
gttgcacacc aggggggtcaa cttggcgtcc tcagttcaaa attgattcaa actaacagtt      60
ccatgtcggg aaacagcacc aggaaactcg tgacatatcg tctttcattg cgagaaacat     120
cttacttatg tacatttcta agctatagcg tctacccttg tcagacccag gacgatgggt     180
gtcacatccc ctttctagtc aacctaagag aggaggaaac gccgcgatat atgttccgcc     240
ctgtcatcac gaagaccacc acaatctatc ccagaacagc cggcacttca ctcacgatgc     300
cccgatgctg gattcctatt gtcgcccttta ttagggcaag cggtgccagt agcagaatat     360
gtcacctcaa caactcgatc caccccctgcc cattacatgg gtaacatatc catggaggtt     420
cgatgtatac ttgaggatac agtcgtccat cacgcccacc tacatacccca ttacatcagc     480
atag                                                                   484
```

<210> SEQ ID NO 31
<211> LENGTH: 484
<212> TYPE: DNA
<213> ORGANISM: Propionibacterium acnes

<400> SEQUENCE: 31

```
gttgcacacc aggggggtcaa cttggcgtcc tcagttcaaa attgattcaa actaacagtt      60
ccatgtcggg aaacagcacc aggaaactcg tgacatatcg tctttcattg cgagaaacat     120
cttacttatg tacatttcta agctatagcg tctacccttg tcagacccag gacgatgggt     180
gtcacatccc ctttctagtc aacctaagag aggaggaaat gccgcgatat atgttccgcc     240
ctgtcatcac gaagaccacc acaatctatc ccagaacagc cggcacttca ctcacgatgc     300
cccgatgctg gattcctatt gtcgcccttta ttagggcaag cggtgccagt agcagaatat     360
gtcacctcaa caactcgatc caccccctgcc cattacatgg gtaacatatc catggaggtt     420
cgatgtatac ttgaggatac agtcgtccat cacgcccacc tacatacccca ttacatcagc     480
atag                                                                   484
```

<210> SEQ ID NO 32
<211> LENGTH: 484
<212> TYPE: DNA
<213> ORGANISM: Propionibacterium acnes

<400> SEQUENCE: 32

```
gttgcacacc aggggggtcaa cttggcgtcc tcagttcaaa attgatttaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatggat     180
gtcacatccc ctttctagtc aacctaagag aggaggaaat gccgcgatat atgttccacc     240
ctgtcatcac gaaggccacc acaatctatc ccagaacagc cggcacctca ctcacgatgc     300
cccgatgctg gattcctatt gtcgcccttta ttagggcaag cggtgccagt agcagaatat     360
gtcacctcaa caactcgatc caccccctgcc cattacatgg gtaacatatc catggaggtt     420
cgatgtatat tcgagaatac agtcgtccat cacgcccgcc tacatacccca ttacatcagc     480
atag                                                                   484
```

<210> SEQ ID NO 33
<211> LENGTH: 484
<212> TYPE: DNA

<213> ORGANISM: Propionibacterium acnes

<400> SEQUENCE: 33

```
gttgcacacc aggggtcaa cttggcgtcc tcagttcaaa attgatttaa actaacagtt      60
ccatgtcggg aaacagcacc agaaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgccctta ttagggcaag cggtgccagt agcagaatat    360
gtcacctcaa caactcgatc caccctgcc cattacatgg gtaacatatc catggaggtt    420
cgatgtatat tcgaggatac agtcgtccat cacgcccgcc tacatacca ttacatcagc     480
atag                                                                484
```

<210> SEQ ID NO 34
<211> LENGTH: 484
<212> TYPE: DNA
<213> ORGANISM: Propionibacterium acnes

<400> SEQUENCE: 34

```
gttgcacacc aggggtcaa cttggcgtcc tcagttcaaa attgatttaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgccctta ttagggcaag cggtgccagt agcagaatat    360
gtcacctcaa caactcgatc caccctgcc cattacatgg gtaacatatc catggaggtt    420
cgatgtatat tcgaggatac agtcgtccat cacgcccgcc tacatacca ttacatcagc     480
atag                                                                484
```

<210> SEQ ID NO 35
<211> LENGTH: 484
<212> TYPE: DNA
<213> ORGANISM: Propionibacterium acnes

<400> SEQUENCE: 35

```
gttgcacacc aggggtcaa cttggcgtcc tcagttcaaa attgatttaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgccctta ttagggcaag cggtgccagt agcagaatat    360
gtcacctcaa caactcgatc caccctgcc cattacatgg gtaacatatc catgaaggtt    420
cgatgtatat tcgaggatac agtcgtccat cacgcccgcc tacatacca ttacatcagc     480
atag                                                                484
```

<210> SEQ ID NO 36
<211> LENGTH: 484
<212> TYPE: DNA
<213> ORGANISM: Propionibacterium acnes

<400> SEQUENCE: 36

```
gttgcacacc aggggtcaa cttggcgtcc tcagttcaaa attgatttaa actaacagtt    60
tcatgtcggg aaacagcacc aggaagctcg tgacatatcg tctttcattg cgagaaacat   120
cttacttatg tacatttcta agctatagcg tctacccttg tcagacccag gacgatggat   180
gtcacatccc ctttctagtc aacctaagag aggaggaaat gccgcgatat atgttccacc   240
ctgtcatcac gaaggccacc acaatctatc ccagaacagc cggcacctca ctcacgatgc   300
cccgatgctg gattcctatt gtcgcccta ttagggcaag cggtgccagt agcagaatat   360
gtcacctcaa caactcgatc caccctgcc cattacatgg gtaacatatc catggaggtt   420
cgatgtatat tcgaggatac agtcgtccat cacgcccgcc tacatacccc ttacatcagc   480
atag                                                                484
```

<210> SEQ ID NO 37
<211> LENGTH: 484
<212> TYPE: DNA
<213> ORGANISM: Propionibacterium acnes

<400> SEQUENCE: 37

```
gttgcacacc aggggtcaa cttggcgtcc tcagttcaaa attgatttaa actaacagtt    60
ccatgtcggg aaacagcacc aggaagctcg tgacatatcg tctttcattg cgagaaacat   120
cttacttatg tacatttcta agctatagcg tctacccttg tcagacccag gacgatggat   180
gtcacatccc ctttctagtc aacctaagag aggaggaaat tccgcgatat atgttccacc   240
ctgtcatcac gaaggccacc acaatctatc ccagaacagc cggcacctca ctcacgatgc   300
cccgatgctg gattcctatt gtcgcccta ttagggcaag cggtgccagt agcagaatat   360
gtcacctcaa caactcgatc caccctgcc cattacatgg gtaacatatc catggaggtt   420
cgatgtatat tcgaggatac agtcgtccat cacgcccgcc tacatacccc ttacatcagc   480
atag                                                                484
```

<210> SEQ ID NO 38
<211> LENGTH: 484
<212> TYPE: DNA
<213> ORGANISM: Propionibacterium acnes

<400> SEQUENCE: 38

```
gttgcacacc agagggtcaa cttggcgtcc tcagttcaaa attgatttaa actaacagtt    60
ccatgtcggg aaacagcacc aggaagctcg tgacatatcg tctttcattg cgagaaacat   120
cttacttatg tacatttcta agctatagcg tctacccttg tcagacccag gacgatggat   180
gtcacatccc ctttctagtc aacctaagag aggaggaaat gccgcgatat atgttccacc   240
ctgtcatcac gaaggccacc acaatctatc ccagaacagc cggcacctca ctcacgatgc   300
cccgatgctg gattcctatt gtcgcccta ttagggcaag cggtgccagt agcagaatat   360
gtcacctcaa caactcgatc caccctgcc cattacatgg gtaacatatc catggaggtt   420
cgatgtatat tcgaggatac agtcgtccat cacgcccgcc tacatacccc ttacatcagc   480
atag                                                                484
```

<210> SEQ ID NO 39
<211> LENGTH: 484
<212> TYPE: DNA
<213> ORGANISM: Propionibacterium acnes

<400> SEQUENCE: 39

```
gttgcacacc aggggggtcaa cttggcgtcc tcagttcaaa attgatttaa actaacagtt      60
ccatgtcggg aaacagcacc aggaagctcg tgacatatcg tctttcattg cgagaaacat     120
cttacttatg tacatttcta agctatagcg tctaccctttg tcagacccag gacgatggat     180
gtcacatccc ctttctagtc aacctaagag aggaggaaat gccgcgatat atgttccacc     240
ctgtcatcac gaaggccacc acaatctatc ccagaacagc cggcgcctca ctcacgatgc     300
cccgatgctg gattcctatt gtcgcccttta ttagggcaag cggtgccagt agcagaatat    360
gtcacctcaa caactcgatc caccccctgcc cattacatgg gtaacatatc catggaggtt    420
cgatgtatat tcgaggatac agtcgtccat cacgcccgcc tacatacccca ttacatcagc    480
atag                                                                  484
```

<210> SEQ ID NO 40
<211> LENGTH: 484
<212> TYPE: DNA
<213> ORGANISM: Propionibacterium acnes

<400> SEQUENCE: 40

```
gttgcacacc aggggggtcaa cttggcgtcc tcagttcaaa atagatttaa actaacagtt      60
ccatgtcggg aaacagcacc aggaagctcg tgacatatcg tctttcattg cgagaaacat     120
cttacttatg tacatttcta agctatagcg tctaccctttg tcagacccag gacgatggat     180
gtcacatccc ctttctagtc aacctaagag aggaggaaat gccgcgatat atgttccacc     240
ctgtcatcac gaaggccacc acaatctatc ccagaacagc cggcacctca ctcacgatgc     300
cccgatgctg gattcctatt gtcgcccttta ttagggcaag cggtgccagt agcagaatat    360
gtcacctcaa caactcgatc caccccctgcc cattacatgg gtaacatatc catggaggtt    420
cgatgtatat tcgaggatac agtcgtccat cacgcccgcc tacatacccca ttacatcagc    480
atag                                                                  484
```

<210> SEQ ID NO 41
<211> LENGTH: 484
<212> TYPE: DNA
<213> ORGANISM: Propionibacterium acnes

<400> SEQUENCE: 41

```
gttgcacacc aggggggtcaa cttggcgtcc tcagttcaaa attgattcaa actaacagtt      60
ccatgtcggg aaacagcacc aggaagctcg tgacatatcg tctttcattg cgagaaacat     120
cttacttatg tatatttcta agctatagcg tctaccctttg tcagacccag gacgatgggt     180
gtcacatccc ctttctagtc aacctaagag aggaggaaat gccgcgatat atgttccacc     240
ctgtcatcac gaacgccacc acaatctatc ccagaacagc cggcacttca ctcacgatgc     300
cccgattctg gattcctatt gtcgcccttta ttagggcaag cggtgccagt agcagaatat    360
gtcacctcaa caactcgatc caccccctgcc cattacatgg gtaacatatc catggaggtt    420
cgatgtatac tcgaggatac agtcgtccat cacgcccgcc tacatacccca ttacatcagc    480
atag                                                                  484
```

<210> SEQ ID NO 42
<211> LENGTH: 484
<212> TYPE: DNA
<213> ORGANISM: Propionibacterium acnes

<400> SEQUENCE: 42

```
gttgcacacc aggggggtcaa cttggcgtcc tcagttcaaa attgattcaa actaacagtt      60
ccatgtcggg aaacagcacc aggaagctcg tgacatatcg tctttcattg cgagaaacat     120
cttacttatg tatatttcta agctatagcg tctacccttg tcagacccag gacgatgggt     180
gtcacatccc ctttctagtc aacctaagag aggaggaaat gccgcgatat atgttccacc     240
ctgtcatcac gaacgccacc acaatctatc ccagaacagc cggcacttca ctcacgatgc     300
cccgattctg gattcctatt gtcgcccctta ttagggcaag cggtgccagt agcagaatat     360
gtcacctcaa caactcgatc caccccctgcc cattacatgg gtaacatatc catggaggtt    420
cgatgtatac tcgaggatac agtcgtccat cacgcccgcc tacataccca ttacaccagc     480
atag                                                                  484

<210> SEQ ID NO 43
<211> LENGTH: 484
<212> TYPE: DNA
<213> ORGANISM: Propionibacterium acnes

<400> SEQUENCE: 43
gttgcacacc aggggggtcaa cttggcgtcc tcagttcaaa attgattcaa actaacagtt     60
ccatgtcggg aaacagcacc aggaagctcg tgacatatcg tctttcattg cgagaaacat    120
cttacttatg tatatttcta agctatagcg tctacccttg tcagacccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgattctg gattcctatt gtcgccctta ttagggcaag cggtgccagt agcagaatat    360
gtcacctaaa caactcgatc caccccctgcc cattacatgg gtaacatatc catggaggtt   420
cgatgtatac tcgaggatac agtcgtccat cacgcccgcc tacataccca ttacatcagc    480
atag                                                                 484

<210> SEQ ID NO 44
<211> LENGTH: 484
<212> TYPE: DNA
<213> ORGANISM: Propionibacterium acnes

<400> SEQUENCE: 44
gttgcacacc aggggggtcaa cttggcgtcc tcagttcaaa attgattcaa actaacagtt     60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgatgctg gattcctatt gtcgccctta ttagggcaag cggtgccagt agcagaatat    360
gtcacctcaa caactcgatc caccccctgcc cattacatgg gtaacatatc catggaggtt   420
cgatgtatac tcgaggatac agtcgtccat cacgcccgcc tacataccca ttacatcagc    480
atag                                                                 484

<210> SEQ ID NO 45
<211> LENGTH: 484
<212> TYPE: DNA
<213> ORGANISM: Propionibacterium acnes

<400> SEQUENCE: 45
```

```
gttgcacacc agggggtcaa cttggcgtcc tcagttcaaa attgattcaa actaacagtt    60
ccatgtcggg aaacagcacc aggaagctcg tgacatatcg tctttcattg cgagaaacat   120
cttacttatg tacatttcta agctatagcg tctacccttg tcagacccag gacgatgggt   180
gtcacatccc ctttctagtc aacctaagag aggaggaaat gccgcgatat atgttccacc   240
ctgtcatcac gaacgccacc acaatctatc ccagaacagc cggcacttca ctcacgatgc   300
cccgatgcta gattcctatt gtcgccctta ttagggcaag cggtgccagt agcagaatat   360
gtcacctcaa caactcgatc cacccctgcc cattacatgg gtaacatatc catggaggtt   420
cgatgtatac tcgaggatac agtcgtccat cacgcccgcc tacatacccA ttacatcagc   480
atag                                                                484
```

<210> SEQ ID NO 46
<211> LENGTH: 484
<212> TYPE: DNA
<213> ORGANISM: Propionibacterium acnes

<400> SEQUENCE: 46

```
gttacacacc agggggtcaa cttggcgtcc tcagttcaaa attgattcaa actaacagtt    60
ccatgtcggg aaacagcacc aggaagctcg tgacatatcg tctttcattg cgagaaacat   120
cttacttatg tacatttcta agctatagcg tctacccttg tcagacccag gacgatgggt   180
gtcacatccc ctttctagtc aacctaagag aggaggaaat gccgcgatat atgttccacc   240
ctgtcatcac gaacgccacc acaatctatc ccagaacagc cggcacttca ctcacgatgc   300
cccgatgctg gattcctatt gtcgccctta ttagggcaag cggtgccagt agcagaatat   360
gtcacctcaa caactcgatc cacccctgcc cattacatgg gtaacatatc catggaggtt   420
cgatgtatac tcgaggatac agtcgtccat cacgcccgcc tacatacccA ttacatcagc   480
atag                                                                484
```

<210> SEQ ID NO 47
<211> LENGTH: 484
<212> TYPE: DNA
<213> ORGANISM: Propionibacterium acnes

<400> SEQUENCE: 47

```
gttgcacacc agggggtcaa cttggcgtcc tcagttcaaa attgattcaa actaacagtt    60
ccatgtcggg aaacagcacc aggaagctcg tgacatatcg tctttcattg cgagaaacat   120
cttacttatg tatatttcta agctatagcg tctacccttg tcagacccag gacgatgggt   180
gtcacatccc ctttctagtc aacctaagag aggaggaaat gccgcgatat atgttccacc   240
ctgtcatcac gaacgccacc acaatctatc ccagaacagc cggcacttca ctcacgatgc   300
cccgattctg gattcctatt gtcgccctta ttagggcaag cggtgccagt agcagaatat   360
gtcacctcaa caactcgatc cacccctgcc cattacatgg gtaacatatc catggaggtt   420
cgatgtatac tcgaggatac agtcgtccat caagcccgcc tacatacccA ttacatcagc   480
atag                                                                484
```

<210> SEQ ID NO 48
<211> LENGTH: 484
<212> TYPE: DNA
<213> ORGANISM: Propionibacterium acnes

<400> SEQUENCE: 48

```
gttgcacacc agggggtcaa cttggcgtcc tcagttcaaa attgattcaa actaacagtt    60
```

```
ccatgtcgga aaacagcacc aggaagctcg tgacatatcg tctttcattg cgagaaacat    120
cttacttatg tacatttcta agctatagcg tctacccttg tcagacccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgatgctg gattcctatt gtcgcccttt ttagggcaag cggtgccagt agcagaatat    360
gtcacctcaa caactcgatc cacccctgcc cattacatgg gtaacatatc catggaggtt    420
cgatgtatac tcgaggatac agtcgtccat cacgcccgcc tacatacccca ttacatcagc    480 atag                                                                484

<210> SEQ ID NO 49
<211> LENGTH: 484
<212> TYPE: DNA
<213> ORGANISM: Propionibacterium acnes

<400> SEQUENCE: 49
gttgcacacc aggggggtcaa cttggcgtcc tcagttcaaa attgattcaa actaacagtt    60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgatgctg gattcctatt gtcgcccttt ttagggcaag cgatgccagt agcagaatat    360
gtcacctcaa caactcgatc cacccctgcc cattacatgg gtaacatatc catggaggtt    420
cgatgtatac tcgaggatac agtcgtccat cacgcccgcc tacatacccca ttacatcagc    480 atag                                                                484

<210> SEQ ID NO 50
<211> LENGTH: 484
<212> TYPE: DNA
<213> ORGANISM: Propionibacterium acnes

<400> SEQUENCE: 50
gttgcacacc aggggggtcaa cttggcgtcc tcagttcaaa attgattcaa actaacagtt    60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacacccc ctttctagtc aacctaagag aggaggaaat gccgcgatat atgttccacc    240
ctgtcatcac gaacgccacc acaatctatc ccagaacagc cggcacttca ctcacgatgc    300
cccgatgctg gattcctatt gtcgcccttt ttagggcaag cggtgccagt agcagaatat    360
gtcacctcaa caactcgatc cacccctgcc cattacatgg gtaacatatc catggaggtt    420
cgatgtatac tcgaggatac agtcgtccat cacgcccgcc tacatacccca ttacatcagc    480 atag                                                                484

<210> SEQ ID NO 51
<211> LENGTH: 484
<212> TYPE: DNA
<213> ORGANISM: Propionibacterium acnes

<400> SEQUENCE: 51
gttgcacacc aggggggtcaa cttggcgtcc tcagttcaaa attgattcaa actaacagtt    60
```

```
ccatgtcggg aaacagcacc aggaagctcg tgacatatcg cctttcattg cgagaaacat    120
cttacttatg tacatttcta agctatagcg tctaccttg tcagacccag gacgatgggt    180
gtcacatccc ctttctagtc aacctaagag aggaggaaat gccgcgatat atgttccacc    240
ctgtcatcac gaacgccacc acaatcgatc cagaacagc cggcacttca ctcacgatgc     300
cccgatgctg gattcctatt gtcgcccta ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacatacca ttacatcagc    480 atag                                                                 484
```

<210> SEQ ID NO 52
<211> LENGTH: 484
<212> TYPE: DNA
<213> ORGANISM: Propionibacterium acnes
<400> SEQUENCE: 52

```
gttgcacacc aggggtcaa cttggcgtcc tcagttcaaa attgattcaa actaacagtt    60
ccatgtcggg aaacagcacc aggaagctcg tgacatatcg tctttcattg cgagaaacat   120
cttacttatg tacatttcta agctatagcg tctaccttg tcagacccag gacgatggat   180
gtcacatccc ctttctagtc aacctaagag aggaggaaat gccgcgatat atgttccacc   240
ctgtcatcac gaaggccacc acaatctatc cagaacagc cggcacttca ctcacgatgc    300
cccgatgctg gattcctatt gtcgcccta ttagggcaag cggtgccagt agcagaatat   360
gtcacctcaa caactcgatc caccctgcc cattacatgg gtaacatatc catggaggtt   420
cgatgtatat tcgaggatac agtcgtccat cacgcccgcc tacatacca ttacatcagc   480 atag                                                                484
```

<210> SEQ ID NO 53
<211> LENGTH: 484
<212> TYPE: DNA
<213> ORGANISM: Propionibacterium acnes
<400> SEQUENCE: 53

```
gttgcacacc aggggtcaa cttggcgtcc tcagttcaaa attgattcaa actaacagtt    60
ccatgtcggg aaacagcacc aggaagctcg tgacatatcg tctttcattg cgagaaacat   120
cttacttatg tacatttcta agctatagcg tctaccttg tcagacccag gacgatggat   180
gtcacatccc ctttctagtc aacctaagag aggaggaaat gccgcgatat atgttccacc   240
ctgtcatcac gaaggccacc acaatctatc cagaacagc cggcacttca ctcacgatgc    300
cccgatgctg gattcctatt gtcgccctca ttagggcaag cggtgccagt agcagaatat   360
gtcacctcaa caactcgatc caccctgcc cattacatgg gtaacatatc catggaggtt   420
cgatgtatat tcgaggatac agtcgtccat cacgcccgcc tacatacca ttacatcagc   480 atag                                                                484
```

<210> SEQ ID NO 54
<211> LENGTH: 484
<212> TYPE: DNA
<213> ORGANISM: Propionibacterium acnes
<400> SEQUENCE: 54

```
gttgcacacc aggggtcaa cttggcgtcc tcagttcaaa attgattcaa actaacagtt    60
ccatgtcggg aaacagcacc aggaagctcg tgacatatcg tctttcattg cgagaaacat   120
```

| | |
|---|---|
| cttacttatg tacatttcta agctatatcg tccaccctttg tcagacccag gacgatggat | 180 |
| gtcacatccc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcaa caactcgatc caccccctgcc cattacatgg gtaacatatc catggaggtt | 420 |
| cgatgtatat tcgaggatac agtcgtccat cacgcccgcc tacataccca ttacatcagc | 480 |
| atag | 484 |

<210> SEQ ID NO 55
<211> LENGTH: 484
<212> TYPE: DNA
<213> ORGANISM: Propionibacterium acnes

<400> SEQUENCE: 55

| | |
|---|---|
| gttgcacacc aggggggtcaa cttggcgtcc tcagttcaaa attgattcaa actaacagtt | 60 |
| ccatgtcggg aaacagcacc aggaagctcg tgacatatcg tctttcattg cgagaaacat | 120 |
| cttacttatg tacatttcta agctatatcg tctaccctttg tcagacccgg gacgatggat | 180 |
| gtcacatccc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcaa caactcgatc caccccctgcc cattacatgg gtaacatatc catggaggtt | 420 |
| cgatgtatat tcgaggatac agtcgtccat cacgcccgcc tacataccca ttacatcagc | 480 |
| atag | 484 |

<210> SEQ ID NO 56
<211> LENGTH: 484
<212> TYPE: DNA
<213> ORGANISM: Propionibacterium acnes

<400> SEQUENCE: 56

| | |
|---|---|
| gttgcacacc aggggggtcaa cttggcgtcc tcagttcaaa attgattcaa actaacagtt | 60 |
| ccatgtcggg aaacagcacc aggaagctcg tgacatatcg tctttcattg cgagaaacat | 120 |
| cttacttatg tacatttcta agccatatcg tctaccctttg tcagacccag gacgatggat | 180 |
| gtcacatccc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcaa caactcgatc caccccctgcc cattacatgg gtaacatatc catggaggtt | 420 |
| cgatgtatat tcgaggatac agtcgtccat cacgcccgcc tacataccca ttacatcagc | 480 |
| atag | 484 |

<210> SEQ ID NO 57
<211> LENGTH: 484
<212> TYPE: DNA
<213> ORGANISM: Propionibacterium acnes

<400> SEQUENCE: 57

| | |
|---|---|
| gttgcacacc aggggggtcaa cttggtgtcc tcagttcaaa attgattcaa actaacggtt | 60 |
| ccgtgtcggg aaacagcacc agaaaactcg tgacatatcg tctttcattg cgagaaacat | 120 |

```
cttacttata cacatttcta agctatattg tctacccctg tcagacccag gacgatgggt    180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacatacccc ttccatcagc    480
atag                                                                484

<210> SEQ ID NO 58
<211> LENGTH: 484
<212> TYPE: DNA
<213> ORGANISM: Propionibacterium acnes

<400> SEQUENCE: 58
gttgcacacc aggggtcaa cttggtgtcc tcagttcaaa attggttcaa actaacggtt     60
ccgtgtcggg aaacagcacc agaaaactcg tgacatatcg tctttcattg cgagaaacat    120
cttacttata cacatttcta agctatattg tctaccccctg tcagacccag gacgatgggt   180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacatacccc ttccatcagc    480
atag                                                                484

<210> SEQ ID NO 59
<211> LENGTH: 483
<212> TYPE: DNA
<213> ORGANISM: Propionibacterium acnes

<400> SEQUENCE: 59
gttgcacacc aggggtcaa cttggtgtcc tcagttcaaa attgattcaa actaacggtt      60
ccgtgtcggg aaacagcacc agaaaactcg tgacatatcg tctttcattg cgagaaacat   120
cttacttata cacatttcta agctatatgt ctaccccctgt cagacccagg acgatgggtg   180
tcatatcccc tttccagtca acctaagaag ggaggaaatg ccgcgatata tgttccgccc    240
tgtcatcatg aatgccacca caatctatcc cggaacagcc gtacttcacc caccatgccc    300
cgatgctgga ttcctattgt cgcccttatt agagcaagcg gtgccagcag cagaatattt    360
cacctcagca actcgatccg ctcctgccca ttacatgggt aacatatcca tggaggtacg    420
atgtatgcat cgaggatgca gtcgtctact atgcccgcct acatacccat tccatcagca    480
tag                                                                 483

<210> SEQ ID NO 60
<211> LENGTH: 484
<212> TYPE: DNA
<213> ORGANISM: Propionibacterium acnes

<400> SEQUENCE: 60
gttgcacacc aggggtcaa cttggtgtcc tcagttcaaa attgattcaa actaacggtt      60
ccgtgtcggg aaacagcacc agaaaactcg taacatatcg tctttcattg cgagaaacat   120
cttacttata cacatttcta agctatattg tctaccccctg tcagacccag gacgatgggt   180
```

```
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacataccca ttccatcagc    480
atag                                                                484
```

<210> SEQ ID NO 61
<211> LENGTH: 484
<212> TYPE: DNA
<213> ORGANISM: Propionibacterium acnes

<400> SEQUENCE: 61

```
gttgcacacc aggggtcaa cttggtgtcc tcagttcaaa attgattcaa actaacggtt    60
ccgtgtcggg aaacagcacc agaaaactcg tgacatatcg tctttcattg cgagaaacat    120
cttacttata cacatttcta agctatattg tctaccctg tcagacccag gacgatgggt    180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
tcgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacataccca ttccatcagc    480
atag                                                                484
```

<210> SEQ ID NO 62
<211> LENGTH: 484
<212> TYPE: DNA
<213> ORGANISM: Propionibacterium acnes

<400> SEQUENCE: 62

```
gttgcacacc aggggtcaa cttggtgtcc tcagttcaaa attgattcaa actaacggtt    60
ccgtgtcggg aaacagcacc agaaaactcg tgacatatcg tctttcattg cgagaaacat    120
cttatttata cacatttcta agctatattg tctaccctg tcagacccag gacgatgggt    180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacataccca ttccatcagc    480
atag                                                                484
```

<210> SEQ ID NO 63
<211> LENGTH: 484
<212> TYPE: DNA
<213> ORGANISM: Propionibacterium acnes

<400> SEQUENCE: 63

```
gttgcacacc aggggtcaa cttggtgtcc tcagttcaaa attgattcaa actaacggtt    60
ccgtgtcggg aaacagcacc agaaaactcg tgacatatcg tctttcattg cgagaaacat    120
cttacttata cacatttcta agctatattg tctaccctg tcagacccag gacgatgggt    180
```

| | |
|---|---|
| gtcatatccc ctttccagtc aacctaagaa ggaaggaaat gccgcgatat atgttccgcc | 240 |
| ctgtcatcat gaatgccacc acaatctatc ccggaacagc cgtacttcac ccaccatgcc | 300 |
| ccgatgctgg attcctattg tcgcccttat tagagcaagc ggtgccagca gcagaatatt | 360 |
| tcacctcagc aactcgatcc gctcctgccc attacatggt taacatatcc atggaggtac | 420 |
| gatgtatgca tcgaggatgc agtcgtctac tatgcccgcc tacataccca ttccatcagc | 480 |
| atag | 484 |

<210> SEQ ID NO 64
<211> LENGTH: 484
<212> TYPE: DNA
<213> ORGANISM: Propionibacterium acnes

<400> SEQUENCE: 64

| | |
|---|---|
| attgcacacc aggggtcaa cttggtgtcc tcagttcaaa attggttcaa actaacggtt | 60 |
| ccgtgtcggg aaacagcacc agaaaactcg tgacatatcg tctttcattg cgagaaacat | 120 |
| cttacttata cacatttcta agctatattg tctaccccctg tcagacccag gacgatgggt | 180 |
| gtcatatccc ctttccagtc aacctaagaa gggaggaaat gccgcgatat atgttccgcc | 240 |
| ctgtcatcat gaatgccacc acaatctatc ccggaacagc cgtacttcac ccaccatgcc | 300 |
| ccgatgctgg attcctattg tcgcccttat tagagcaagc ggtgccagca gcagaatatt | 360 |
| tcacctcagc aactcgatcc gctcctgccc attacatggg taacatatcc atggaggtac | 420 |
| gatgtatgca tcgaggatgc agtcgtctac tatgcccgcc tacataccca ttccatcagc | 480 |
| atag | 484 |

<210> SEQ ID NO 65
<211> LENGTH: 484
<212> TYPE: DNA
<213> ORGANISM: Propionibacterium acnes

<400> SEQUENCE: 65

| | |
|---|---|
| gttgcacacc aggggtcaa cttggtgtcc tcagttcaaa attggttcaa actaacggtt | 60 |
| ccgtgtcggg aaacagcacc agaaaactcg tgacatatcg tctttcattg cgagaaacat | 120 |
| cttacttata cacatttcta agctatattg tctaccccctg tcagacccag gacgatgggt | 180 |
| gtcatatccc ctttccagtc aacctaagaa gggaggaaat gccgcgatat atgttccgcc | 240 |
| ctgtcatcat gaatgccacc acaatctatc ccggaacagc cgtacttcac ccaccatgcc | 300 |
| ccgatgctgg attcctatgg tcgcccttat tagagcaagc ggtgccagca gcagaatatt | 360 |
| tcacctcagc aactcgatcc gctcctgccc attacatggg taacatatcc atggaggtac | 420 |
| gatgtatgca tcgaggatgc agtcgtctac tatgcccgcc tacataccca ttccatcagc | 480 |
| atag | 484 |

<210> SEQ ID NO 66
<211> LENGTH: 483
<212> TYPE: DNA
<213> ORGANISM: Propionibacterium acnes

<400> SEQUENCE: 66

| | |
|---|---|
| gttgcacacc aggggtcaa cttggtgtcc tcagttcaaa attgattcaa actaacggtt | 60 |
| ccgtgtcggg aaacagcacc agaaaactcg tgacatatca tctttcattg cgagaaacat | 120 |
| cttacttata cacatttcta agctatatgt ctaccctgt cagacccagg acgatgggtg | 180 |
| tcatatcccc tttccagtca acctaagaag ggaggaaatg ccgcgatata tgttccgccc | 240 |

```
tgtcatcatg aatgccacca caatctatcc cggaacagcc gtacttcacc caccatgccc    300
cgatgctgga ttcctattgt cgcccttatt agagcaagcg gtgccagcag cagaatattt    360
cacctcagca actcgatccg ctcctgccca ttacatgggt aacatatcca tggaggtacg    420
atgtatgcat cgaggatgca gtcgtctact atgcccgcct acatacccat tccatcagca    480
tag                                                                  483
```

<210> SEQ ID NO 67
<211> LENGTH: 484
<212> TYPE: DNA
<213> ORGANISM: Propionibacterium acnes

<400> SEQUENCE: 67

```
gttgcacacc aggggqtcaa cttggtgtcc tcagttcaaa attggttcaa actaacggtt     60
ccgtgtcggg aaacagcacc agaaaactcg tgacatgtcg tctttcattg cgagaaacat    120
cttacttata cacatttcta agctatattg tctaccccctg tcagacccag gacgatgggt   180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacatacccca ttccatcagc   480 atag                                                                 484
```

<210> SEQ ID NO 68
<211> LENGTH: 484
<212> TYPE: DNA
<213> ORGANISM: Propionibacterium acnes

<400> SEQUENCE: 68

```
gttgcacacc aggggqtcaa cttggtgtcc tcagttcaaa attggttcaa actaacggtt     60
ccgtgtcggg aaacagcacc agaaaactcg tgacatatcg tctttcattg cgagaaacat    120
cttacttata cacatttcta agctatactg tctaccccctg tcagacccag gacgatgggt   180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacatacccca ttccatcagc   480 atag                                                                 484
```

<210> SEQ ID NO 69
<211> LENGTH: 484
<212> TYPE: DNA
<213> ORGANISM: Propionibacterium acnes

<400> SEQUENCE: 69

```
gttgcacacc aggggqtcaa cttggtgtcc tcagttcaaa attggttcaa actaacggtt     60
ccgtgtcggg aaacagcacc agaaaacttg tgacatatcg tctttcattg cgagaaacat    120
cttacttata cacatttcta agctatattg tctaccccctg tcagacccag gacgatgggt   180
gtcatatccc ctttccagtc aacctaagaa gggaggaaat gccgcgatat atgttccgcc    240
```

```
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacatacccca ttccatcagc    480 atag                                                                  484

<210> SEQ ID NO 70
<211> LENGTH: 484
<212> TYPE: DNA
<213> ORGANISM: Propionibacterium acnes

<400> SEQUENCE: 70
gttgcacacc aggggggtcaa cttggtgtcc tcagttcaaa attggttcaa actaacggtt     60
ccgtgtcggg aaacagcacc agaaaactca tgacatatcg tctttcattg cgagaaacat    120
cttacttata cacatttcta agctatattg tctacccctg tcagacccag gacgatgggt    180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacatacccca ttccatcagc    480 atag                                                                  484

<210> SEQ ID NO 71
<211> LENGTH: 484
<212> TYPE: DNA
<213> ORGANISM: Propionibacterium acnes

<400> SEQUENCE: 71
gttgcacacc aggggggtcaa cttggtgtcc tcagttcaaa attgattcaa actaacggtt     60
ccgtatcggg aaacagcacc agaaaactcg gacatatcg tctttcattg cgagaaaaat    120
cttacttatg cgcatttcta agctatagcg tctaccctttg tcagacccag gacgatgagt    180
gtcacatccc ctttccagtc aacctaagag aggaggaaat gccgcgatat atgctccgcc    240
ctgtcatcac gaaagccacc acaatctatc ccagaacagc cggcacttca ctcacgatgc    300
cccgatgctg gattcctatt gtcgccctta ttagggcaag cggtgccagt agcagaatat    360
gtcacctcag caactcgatc cgcccctgcc cattacatgg gtaacatatc catggaggtt    420
cgatgtatac tcgaggatac agtcgcccat cacgccagcc tacataccca ttacatcagc    480
atag                                                                  484

<210> SEQ ID NO 72
<211> LENGTH: 484
<212> TYPE: DNA
<213> ORGANISM: Propionibacterium acnes

<400> SEQUENCE: 72
gttgcacacc aggggggtcaa cttggtgtcc tcagttcaaa attgattcaa actaacggtt     60
ccgtatcggg aaacagcacc agaaaactcg gacatatcg tctttcattg cgagaaaaat    120
cttacttatg cgcatttcta agctatagcg tctaccctttg ccagacccag gacgatgagt    180
gtcacatccc ctttccagtc aacctaagag aggaggaaat gccgcgatat atgctccgcc    240
ctgtcatcac gaaagccacc acaatctatc ccagaacagc cggcacttca ctcacgatgc    300
```

```
cccgatgctg gattcctatt gtcgcccttta ttagggcaag cggtgccagt agcagaatat    360
gtcacctcag caactcgatc cgcccctgcc cattacatgg gtaacatatc catggaggtt    420
cgatgtatac tcgaggatac agtcgcccat cacgccagcc tacataccca ttacatcagc    480
atag                                                                 484
```

<210> SEQ ID NO 73
<211> LENGTH: 484
<212> TYPE: DNA
<213> ORGANISM: Propionibacterium acnes

<400> SEQUENCE: 73

```
gttgcacacc aggggtcaa cttggtgtcc tcagttcaaa attgattcaa actaacggtt    60
ccgtatcggg aaacagcacc agaaaactcg ggacatatcg tctttcattg cgagaaaaat   120
cttacttatg cgcatttcta agctatatcg tctacccttg ccagacccag gacgatgagt   180
gtcacatccc ctttccagtc aacctaagag aggaggaaat gccgcgatat atgctccgcc   240
ctgtcatcac gaaagccacc acaatctatc ccagaacagc cggcacttca ctcacgatgc   300
cccgatgctg gattcctatt gtcgcccttta ttagggcaag cggtgccagt agcagaatat   360
gtcacctcag caactcgatc cgcccctgcc cattacatgg gtaacatatc catggaggtt   420
cgatgtatac tcgaggatac agtcgcccat cacgccagcc tacataccca ttacatcagc   480
atag                                                                484
```

<210> SEQ ID NO 74
<211> LENGTH: 484
<212> TYPE: DNA
<213> ORGANISM: Propionibacterium acnes

<400> SEQUENCE: 74

```
gttgcacacc aggggtcaa cttggtgtcc tcagttcaaa attgattcaa actaacggtt    60
ccgtgtcggg aaacagcacc agaaaactcg ggacatatcg tctttcattg cgagaaaaat   120
cttacttatg cgcatttcta agctatagcg tctacccttg tcagacccag gacgatgagt   180
gtcacatccc ctttccagtc aacctaagag aggaggaaat gccgcgatat atgctccgcc   240
ctgtcatcac gaaagccacc acaatctatc ccagaacagc cggcacttca ctcacgatgc   300
cccgatgctg gattcctatt gtcgcccttta ttagggcaag cggtgccagt agcagaatat   360
gtcacctcag caactcgatc cgcccctgcc cattacatgg ttaacatatc catggaggtt   420
cgatgtatac tcgaggatac agtcgcccat cacgccagcc tacataccca ttacatcagc   480
atag                                                                484
```

<210> SEQ ID NO 75
<211> LENGTH: 484
<212> TYPE: DNA
<213> ORGANISM: Propionibacterium acnes

<400> SEQUENCE: 75

```
gttgcacacc aggggtcaa cttggtgtcc tcagttcaaa attgattcaa actaacggtt    60
ccgtgtcggg aaacagcacc agaaaactcg ggacatatcg tctttcattg cgagaaaaat   120
cttacttatg cgcatttcta agctatagcg tctacccttg tcagacccag gacgatgagt   180
gtcacatccc ctttccagtc aacctaagag aggaggaaat gccgcgatat atgctccgcc   240
ctgtcatcac gaaagccacc acaatctatc ccagaacagc cggcacttca ctcacgatgc   300
```

```
cccgatgctg gattcctatt gtcgccctta ttagggcaag cggtgccagt agcagaatat    360
gtcacctcag caactcgatc cgcccctgcc cattacatgg gtaacatatc catggaggtt    420
cgatgtatac tcgaggatac agtcgcccat cacgccagcc tacataccca ttacatcagc    480
atag                                                                 484

<210> SEQ ID NO 76
<211> LENGTH: 484
<212> TYPE: DNA
<213> ORGANISM: Propionibacterium acnes

<400> SEQUENCE: 76
gttgcacacc aggggtcaa cttggtgtcc tcagttcaaa attgattcaa actaacggtt     60
ccgtatcggg aaacagcacc agaaaactcg ggacatatcg tctttcattg cgagaaaaat   120
cttacttatg cgcatttcta agctatagcg tctacccttg tcagacccag gacgatgagt   180
gtcacatccc ctttccagtc aacctaagag aggaggaaat gccgcgatat atgctccgcc   240
ctgtcatcac gaaagccacc acaatctatc ccagaacagc cggcacttca ctcacgatgc   300
cccgatgctg gattcctatt gtcgccctta ttagggcaag cggtgccagt agcagaatat   360
gtcacctcag caactcgatc cgcccccgcc cattacatgg gtaacatatc catggaggtt   420
cgatgtatac tcgaggatac agtcgcccat cacgccagcc tacataccca ttacatcagc   480
atag                                                                484

<210> SEQ ID NO 77
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 77
cagcggcgct gctaagaact t                                              21

<210> SEQ ID NO 78
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 78
ccggctggca aatgaggcat                                                20

<210> SEQ ID NO 79
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 79
tcgtcggcag cgtcagatgt gtataagaga cagcagcggc gctgctaaga actt          54

<210> SEQ ID NO 80
<211> LENGTH: 54
<212> TYPE: DNA
<213> ORGANISM: Artificial Sequence
```

```
-continued

<220> FEATURE:
<223> OTHER INFORMATION: Synthetic Polynucleotide

<400> SEQUENCE: 80
gtctcgtggg ctcggagatg tgtataagag acagccggct ggcaaatgag gcat        54
```

METHODS AND COMPOSITIONS FOR CHANGING THE COMPOSITION OF THE SKIN MICROBIOME USING COMPLEX MIXTURES OF BACTERIAL STRAINS

RELATED APPLICATIONS

This application is a continuation of U.S. application Ser. No. 15/567,941, filed on Oct. 19, 2017, entitled "METHODS AND COMPOSITIONS FOR CHANGING THE COMPOSITION OF THE SKIN MICROBIOME USING COMPLEX MIXTURES OF BACTERIAL STRAINS" which is a national stage filing under 35 U.S.C. § 371 of International Application No. PCT/US2016/028421, entitled "METHODS AND COMPOSITIONS FOR CHANGING THE COMPOSITION OF THE SKIN MICROBIOME USING COMPLEX MIXTURES OF BACTERIAL STRAINS," filed on Apr. 20, 2016, which was published under PCT Article 21(2) in English, and which claims the benefit under 35 U.S.C. § 119(e) of U.S. Provisional Application Ser. No. 62/150,225, filed on Apr. 20, 2015, entitled "METHODS AND COMPOSITIONS FOR CHANGING THE COMPOSITION OF THE SKIN MICROBIOME USING COMPLEX MIXTURES OF BACTERIAL STRAINS" and U.S. Provisional Application Ser. No. 62/216,258, filed on Sep. 9, 2015, entitled "METHODS AND COMPOSITIONS FOR CHANGING THE COMPOSITION OF THE SKIN MICROBIOME USING COMPLEX MIXTURES OF BACTERIAL STRAINS," the entire disclosure of each of which is incorporated by reference herein in its entirety.

FIELD OF INVENTION

The invention relates to methods and compositions for modifying the skin microbiome.

BACKGROUND OF INVENTION

The human body is host to a highly complex and rich microbial community. These microorganisms are generally harmless and contribute to a healthy state by producing vitamins, cooperating with digesting food, or stimulating the immune system. The human microbiota mainly resides on the surface and in deep layers of skin, in the saliva and oral mucosa, in the conjunctiva, and in the gastrointestinal tracts.

It has been demonstrated, primarily in the gut, that human microbiota have fundamental roles in human health and disease. The skin is colonized by a large number of microorganisms, most of them are beneficial or harmless. However, the skin microbiome has specific compositions in diseases states of skin that are different compared to healthy skin. Diseases such as acne vulgaris are associated with strong alterations of the microbiome.

SUMMARY OF INVENTION

Aspects of the invention relate to a method for treating acne, comprising topically administering a disinfectant or antibiotic to the skin of a subject with acne; and topically administering a composition comprising one or more live bacterial strains to the skin of the subject following administration of the disinfectant or antibiotic, wherein the one or more live bacterial strains are *P. acnes* bacterial strains.

Further aspects of the invention relate to a method comprising topically administering a composition comprising one or more live bacterial strains to the skin of a subject, wherein the one or more live bacterial strains are *P. acnes* bacterial strains.

In some embodiments, the method is a method for maintaining healthy skin, modulating the skin microbiome of a subject, treating acne, preventing acne, modifying the sebum production of sebaceous glands of a subject, delivering trans-10, cis-12 linoleic acid to the cells of the sebaceous glands or hair follicles of a subject, modifying the bacterial density on the skin of a subject, and/or modifying the ratio of select bacterial species relative to other bacterial species or relative to other microorganisms on the skin of a subject.

In some embodiments, the composition is administered to the skin of a subject following administration of a standard acne treatment. In some embodiments, the standard acne treatment comprises administration of an antibiotic or disinfectant. In some embodiments, the composition is in the form of a gel, cream, ointment, lotion, serum, powder, aerosol spray or two-component dispensing system. In some embodiments, the composition further comprises one or more of a buffer, thickener or carrier.

In some embodiments, the composition comprises 2, 3, 4, 5, 6, 7, 8, 9, 10 or more than 10 different *P. acnes* bacterial strains. In some embodiments, the composition comprises the *P. acnes* 6609 (H1) bacterial strain and/or the *P. acnes* C1 bacterial strain.

In some embodiments, the composition is stable at room temperature for at least three months. In some embodiments, the composition is not naturally occurring. In some embodiments, one or more of the *P. acnes* bacterial strains is selected from the group of non-pathogenic *P. acnes* strains consisting of: D1, A5, C3, H1, H2, H3, K1, K2, K4, K6, K8, K9, L1 and F4.

In some embodiments, the composition further comprises one or more of an antibiotic, a disinfectant or salicylic acid. In some embodiments, the composition further comprises an *S. epidermidis* bacterial strain that inhibits or reduces the growth of other bacterial strains. In some embodiments, one or more of the *P. acnes* bacterial strains is resistant to the antibiotic or disinfectant. In some embodiments, the composition further comprises peptone.

In some embodiments, the subject is a human. In some embodiments, one or more of the live bacterial strains are components of the skin microbiome. In some embodiments, one or more of the *P. acnes* bacterial strains within the composition produces low or negligible levels of trans-10, cis-12 linoleic acid. In some embodiments, one or more of the *P. acnes* bacterial strains within the composition is non-pathogenic, as demonstrated by exhibiting a slow or negligible conversion or degradation of cis-9, cis-12 linoleic acid in media.

Aspects of the invention relate to the use of a composition comprising one or more live bacterial strains for treatment of acne, wherein the composition is topically administered to the skin of a subject with acne following administration of a disinfectant or antibiotic to the skin of the subject, wherein the one or more live bacterial strains are *P. acnes* bacterial strains, and optionally wherein one or more of the live bacterial strains are selected from the group consisting of: *P. acnes* 6609 (H1), C1, C3, D1, A5, H1, H2, H3, K1, K2, K4, K6, K8, K9, L1 and F4 bacterial strains.

Further aspects of the invention relate to a composition comprising one or more live bacterial strains for topical administration to the skin, wherein the one or more live bacterial strains are *P. acnes* bacterial strains.

Further aspects of the invention relate to cosmetic compositions comprising one or more live bacterial strains for topical administration to the skin, wherein the one or more live bacterial strains are *P. acnes* bacterial strains.

Further aspects of the invention relate to pharmaceutical compositions comprising one or more live bacterial strains for topical administration to the skin, wherein the one or more live bacterial strains are *P. acnes* bacterial strains.

In some embodiments, the composition is in the form of a gel, cream, ointment, lotion, serum, powder, aerosol spray or two-component dispensing system. In some embodiments, the composition further comprises one or more of a buffer, thickener or carrier.

In some embodiments, the composition comprises 2, 3, 4, 5, 6.7, 8, 9, 10 or more than 10 different *P. acnes* bacterial strains. In some embodiments, the composition comprises the *P. acnes* 6609 (H1) bacterial strain and/or the *P. acnes* C1 bacterial strain. In some embodiments, the composition is stable at room temperature for at least three months.

In some embodiments, the composition is for treating or preventing acne. In some embodiments, the composition is for maintaining healthy skin. In some embodiments, the composition is not naturally occurring.

In some embodiments, one or more of the *P. acnes* bacterial strains is selected from the group of non-pathogenic strains consisting of: D1, A5, C3, H1, H2, H3, K1, K2, K4, K6, K8, K9, L1 and F4. In some embodiments, the composition further comprises one or more of an antibiotic, a disinfectant or salicylic acid.

In some embodiments, the composition further comprises an *S. epidermidis* bacterial strain that inhibits or reduces the growth of other bacterial strains. In some embodiments, one or more of the *P. acnes* bacterial strains is resistant to the antibiotic or disinfectant.

In some embodiments, the composition further comprises peptone. In some embodiments, the one or more live bacterial strains are components of the skin microbiome. In some embodiments, one or more of the *P. acnes* bacterial strains within the composition produces low or negligible levels of trans-10, cis-12 linoleic acid, optionally wherein all of the *P. acnes* bacterial strains within the composition produce low or negligible levels of trans-10, cis-12 linoleic acid.

In some embodiments, one or more of the *P. acnes* bacterial strains within the composition is selected based on: its ability to produce trans-10, cis-12 linoleic acid; the amount of trans-10, cis-12 linoleic acid it produces in natural environment; the maximum concentration of trans-10, cis-12 linoleic acid it produces; and/or the activity of the enzyme linoleic acid isomerase it produces.

In some embodiments, one or more of the *P. acnes* bacterial strains within the composition is selected based on its rate of conversion or degradation of cis-9, cis-12 linoleic acid in media. In some embodiments, one or more of the *P. acnes* bacterial strains within the composition exhibits a slow or negligible conversion or degradation of cis-9, cis-12 linoleic acid in media.

In some embodiments, the method comprises administering a composition described herein to a subject. In some embodiments, the subject is a human.

Aspects of the invention relate to a method comprises obtaining one or more live bacterial strains from the skin of a donor subject, wherein the live bacterial strains are *P. acnes* strains, determining whether the one or more live bacterial strains are pathogenic, and administering the one or more live bacterial strains to the skin of a recipient subject in need thereof following administration of a disinfectant or antibiotic to the skin of the subject if the one or more live bacterial strains are not pathogenic.

In some embodiments, the donor subject and recipient subject are different. In some embodiments, the donor subject and recipient subject are the same. In some embodiments, an assay is performed to determine whether the live bacterial strain is pathogenic. In some embodiments, the assay comprises assessing the ability of the live bacterial strain to convert or degrade cis-9, cis-12 linoleic acid.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3A shows a heat map displaying the relative abundance of 16S repertoire after transplantation. After several days of application, the recipient subject's 16S profile became closer to the donor subject's 16S profile. FIG. 3B shows that *P. acnes* strains transferred from donor to recipient. In the upper panel, the bar chart indicates how some *P. acnes* strains populated the skin of the recipient. In the lower panel, a phylogenetic tree of the strains analyzed is shown (based on Single Locus Sequence Typing (SLST) alleles). FIG. 3C shows a detailed population of the different *P. acnes* strains in the donor and recipient. FIG. 3D shows that a recipient subject's microbiome became more similar to the donor subject's microbiome after 3 days of application. Spearman correlation was used to measure the distance between different microbiomes.

FIG. 8 depicts a minimum inhibitory concentration test where three different *P. acnes* strains were tested in combination with four compounds: Glycolic acid, Hyaluronic acid, Lactic acid and Salicylic acid. Concentrations where no or minimal inhibition was observed can be used in bacterial composition to enhance the features of cosmetic or pharmaceutical compositions.

FIG. 9 depicts results of a pilot clinical study recorded by a dermatologist. 10 subjects with acne vulgaris were visually evaluated by the dermatologist at week 0, week 1 (day 7) and week 3 (day 21) and lesion reduction was noted. In week 1, subjects were administered with Benzoyl Peroxide. In weeks 2 and 3, subjects were administered with bacterial compositions. Reduced lesions were recorded in 4 subjects at the end of the week 1 (after Benzyol Peroxide application) and in 5 subjects at the end of the week 3 (after bacterial composition application). Additionally, skin irritation was evaluated during the study.

DETAILED DESCRIPTION

Figure 1:
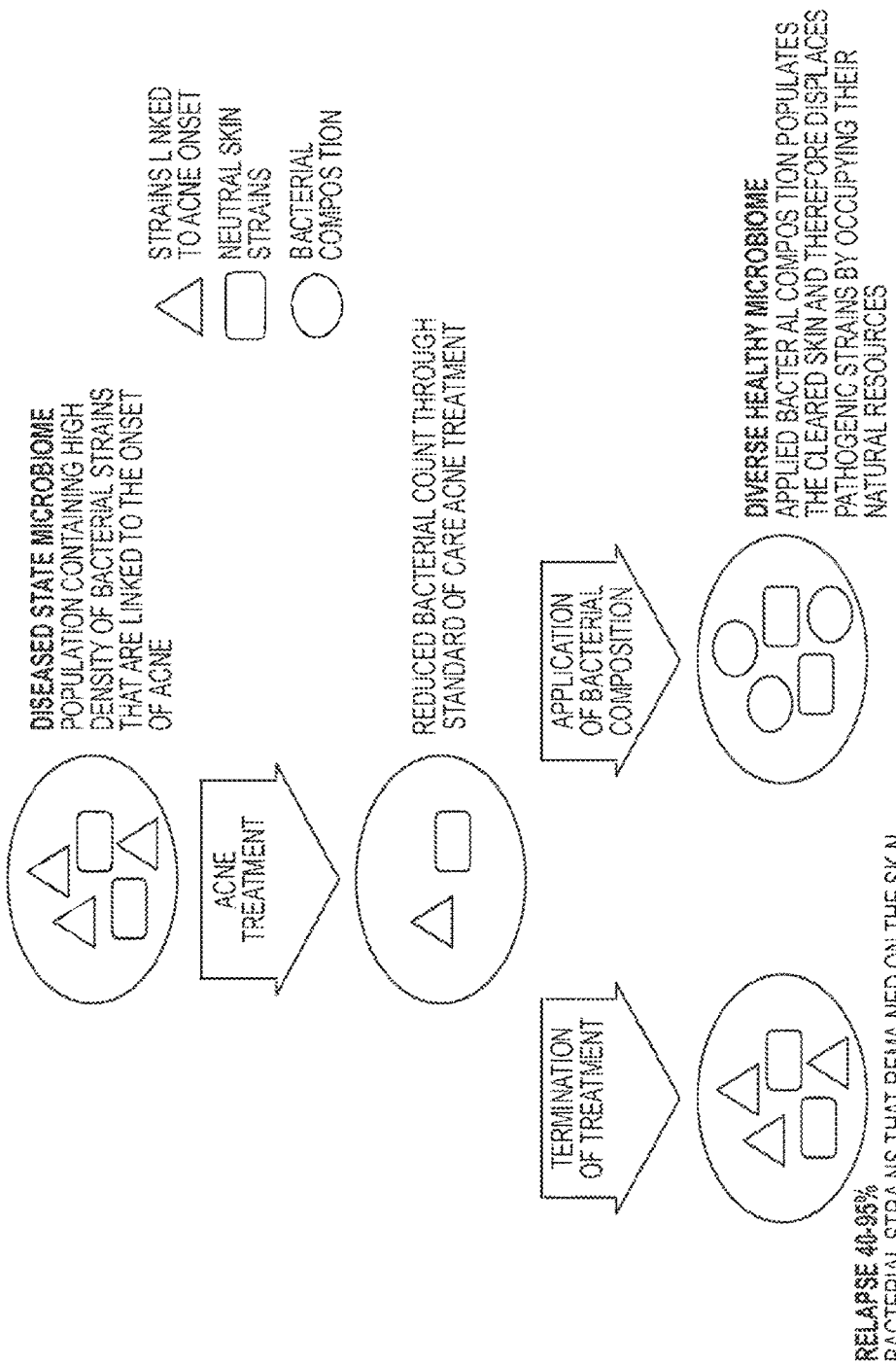
FIG. 1 is a schematic representation of activity of a composition comprising one or more live bacteria as described herein in combination with a standard antibiotic or disinfectant treatment. The composition comprising one or more live bacteria establishes a healthy microbiome on the skin following treatment of the skin with an antibiotic or disinfectant treatment.
Figure 2:
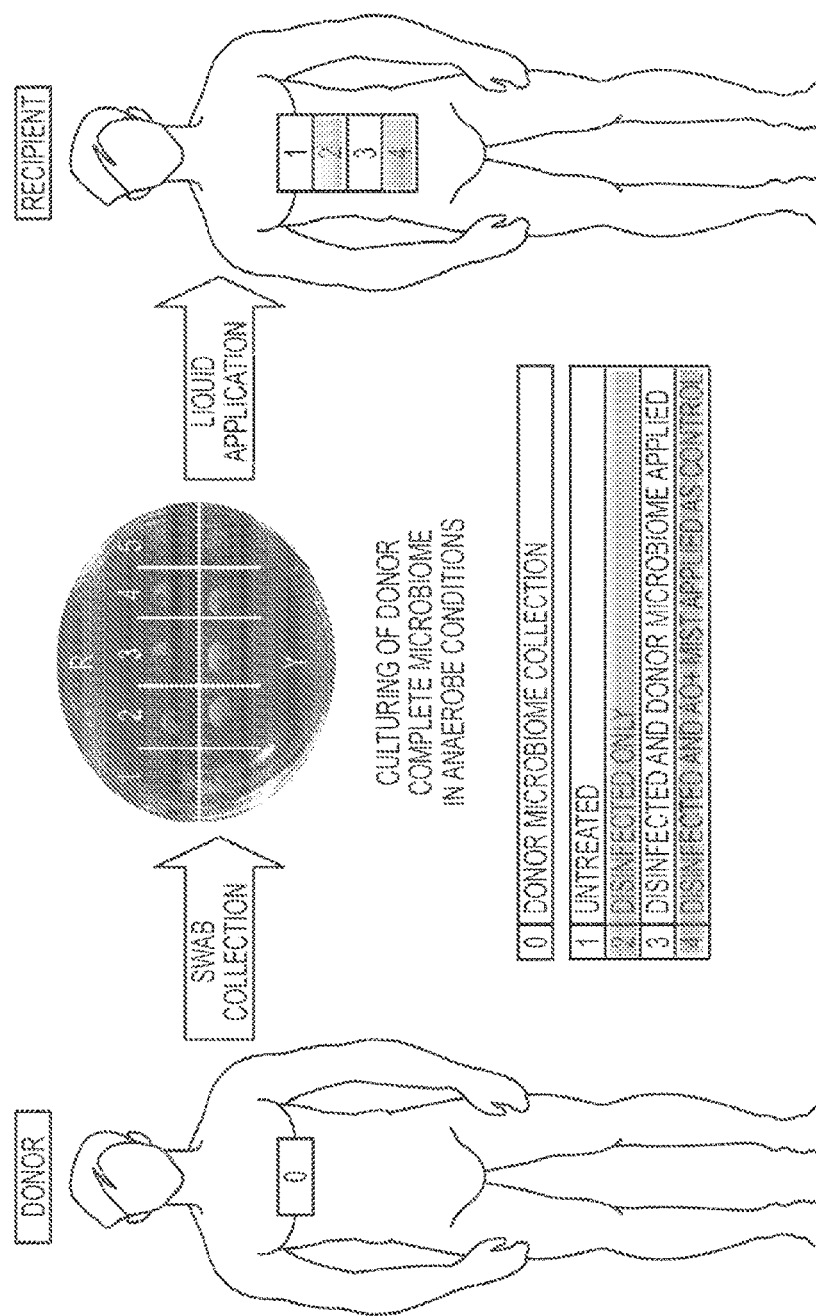
FIG. 2 depicts a microbiome transplantation. A sample of a donor subject's microbiome was cultivated and expanded in the laboratory. Then, the bacterial culture was transplanted onto the previously sterilized skin of a recipient (acceptor) subject.
Figure 3A:
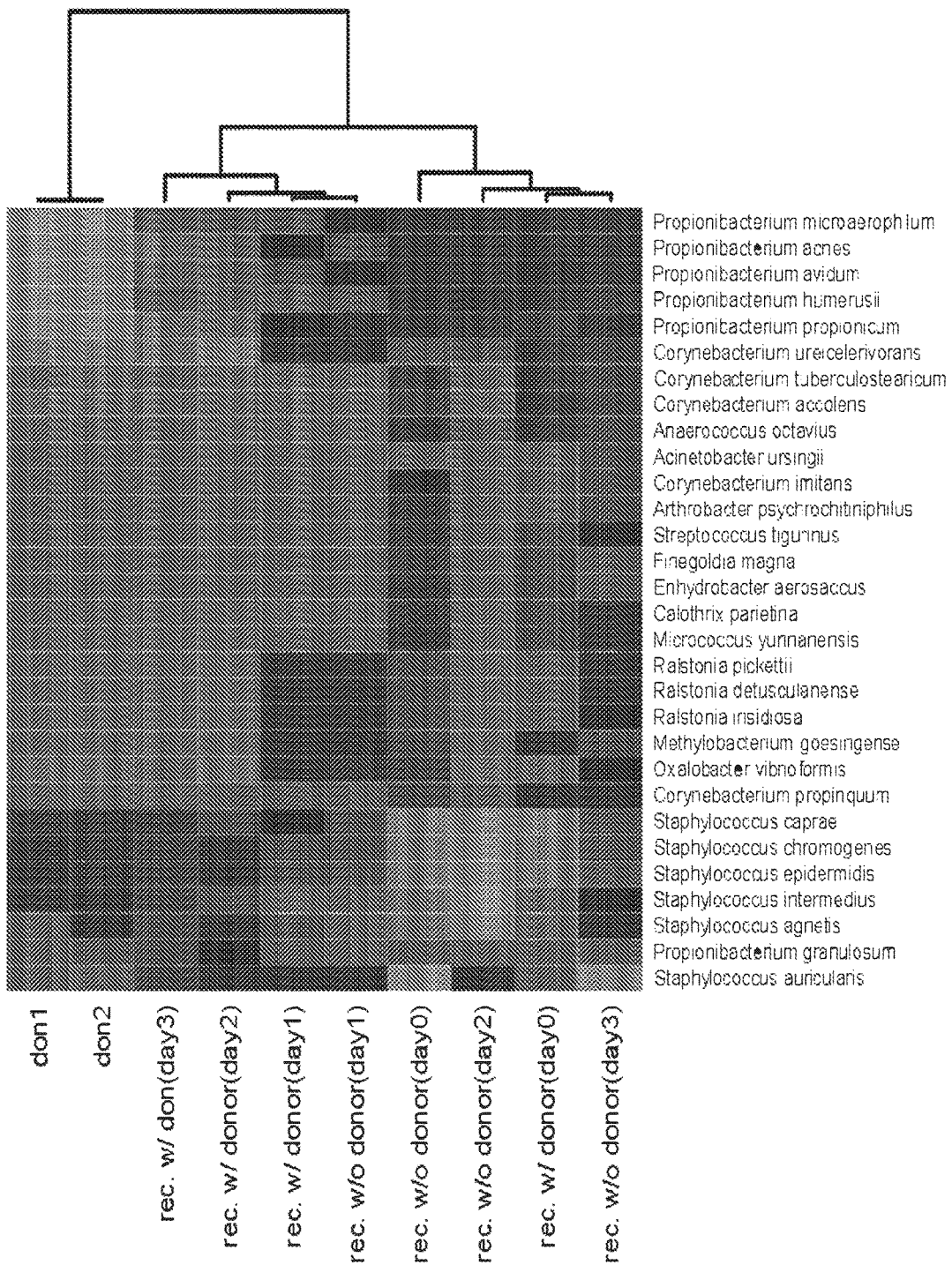
FIGS. 3A-3D depict microbiome change after transplantation.
Figure 3B:
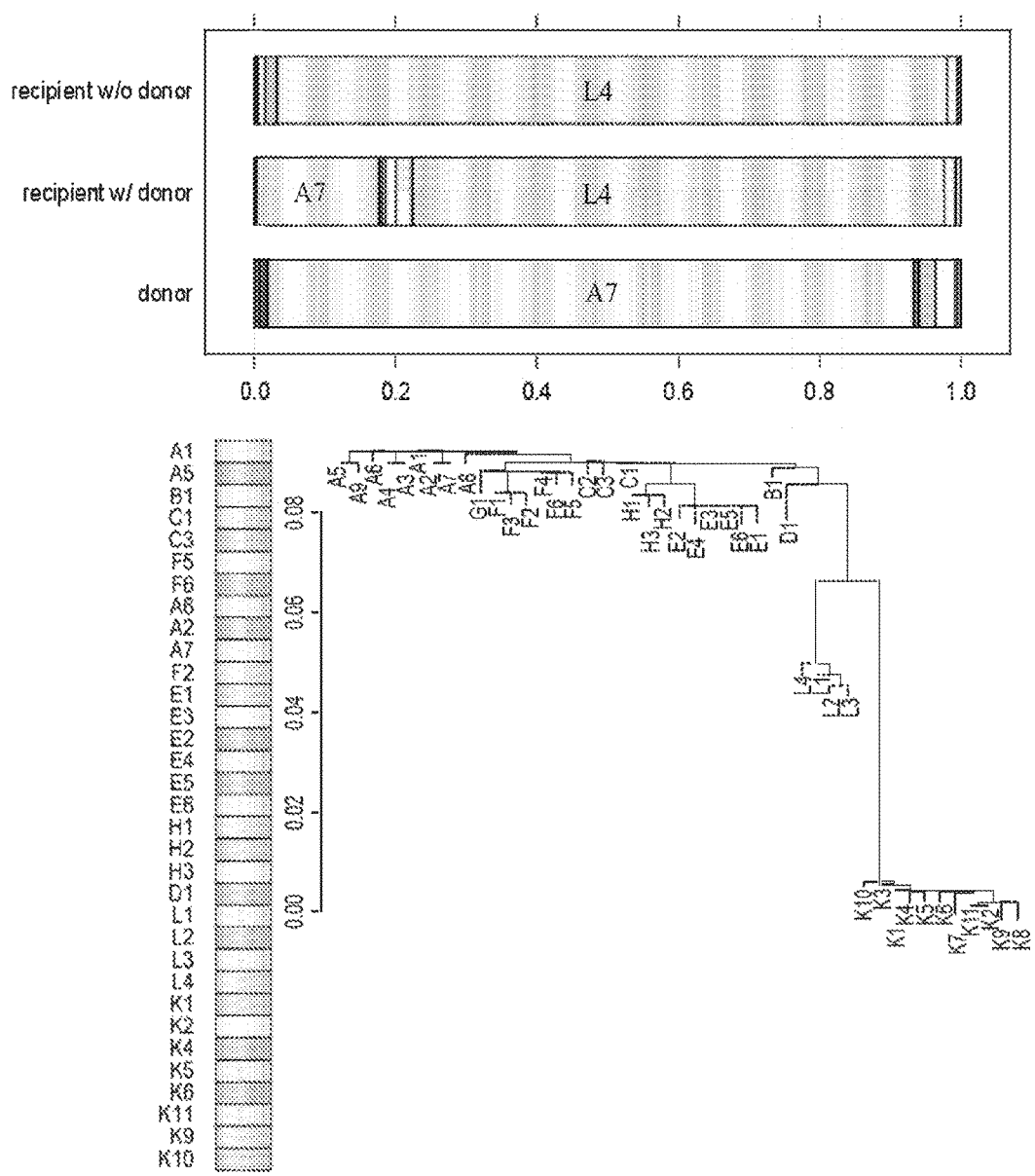
Figure 3C:
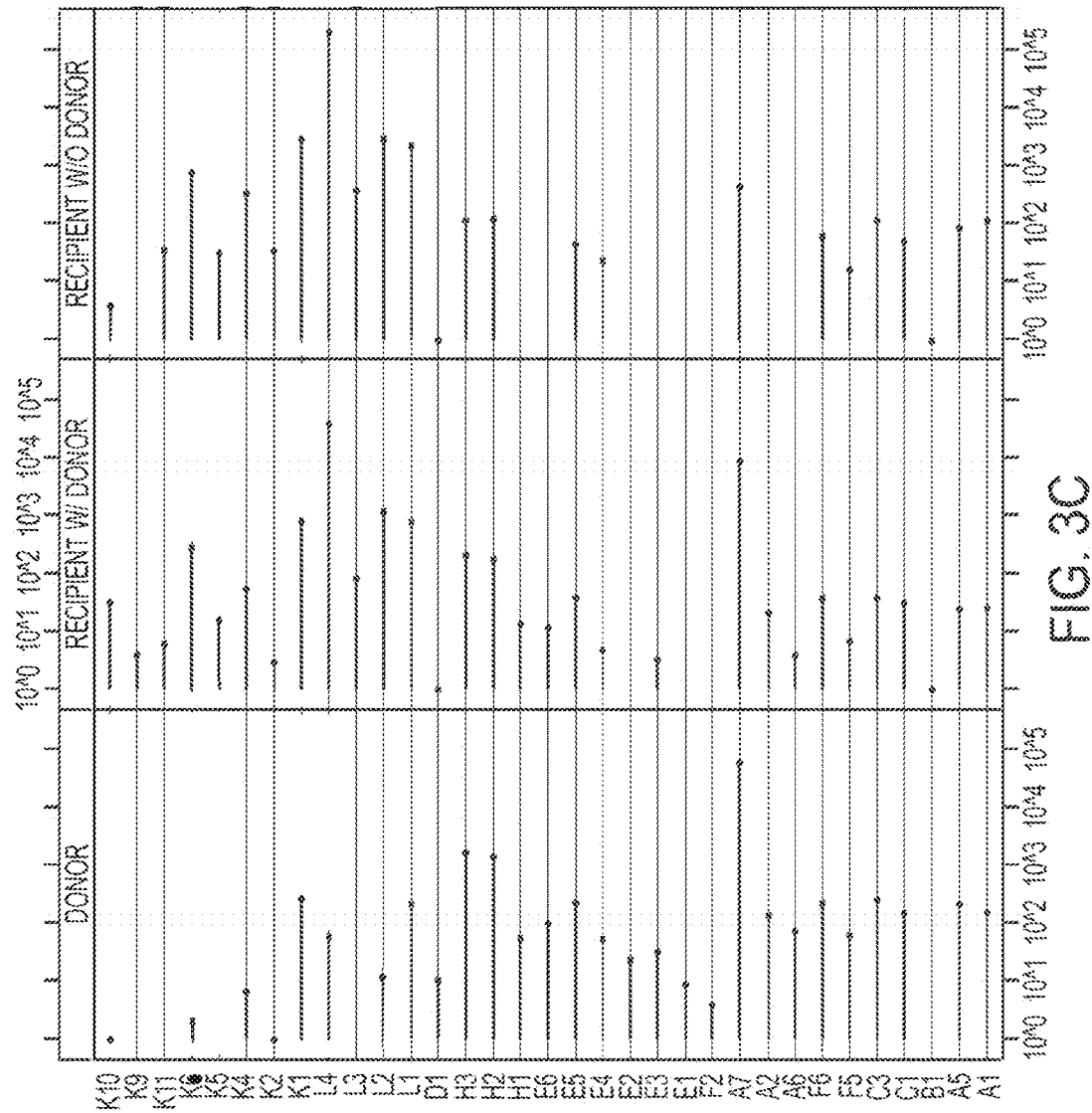
Figure 3D:
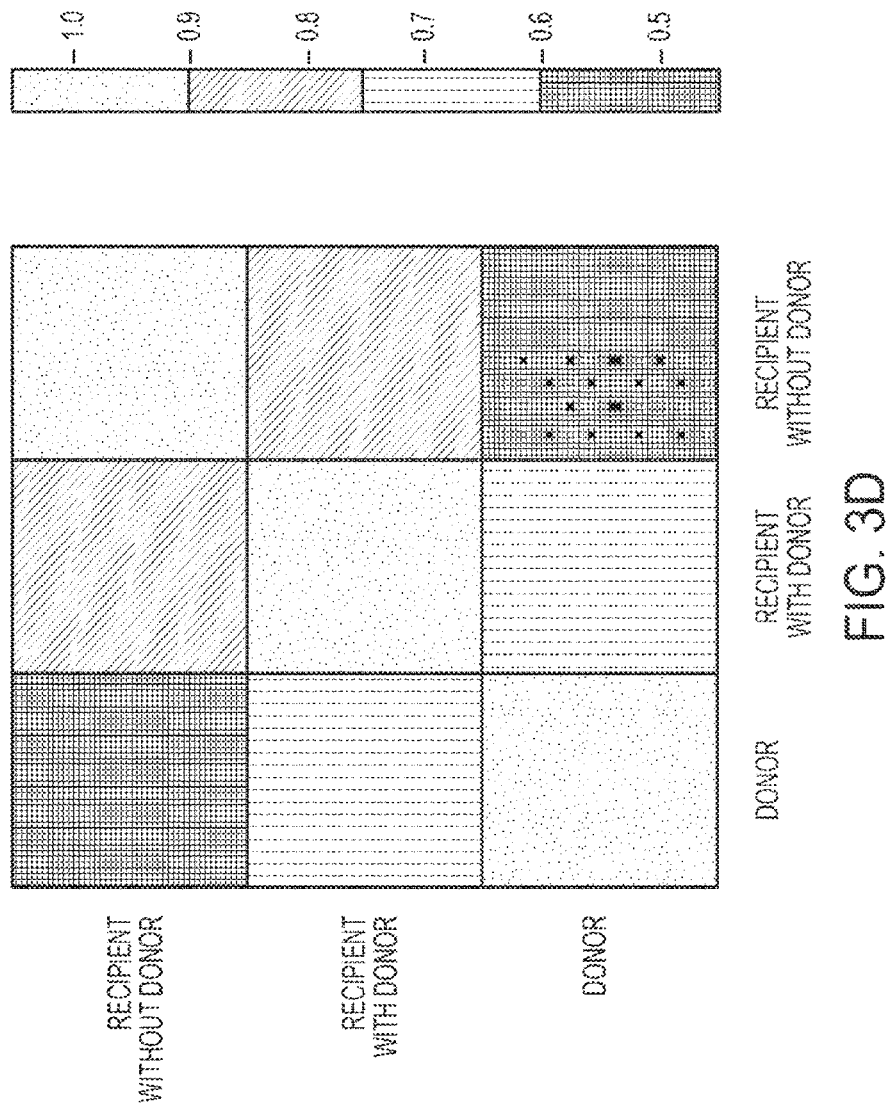
Figure 4:
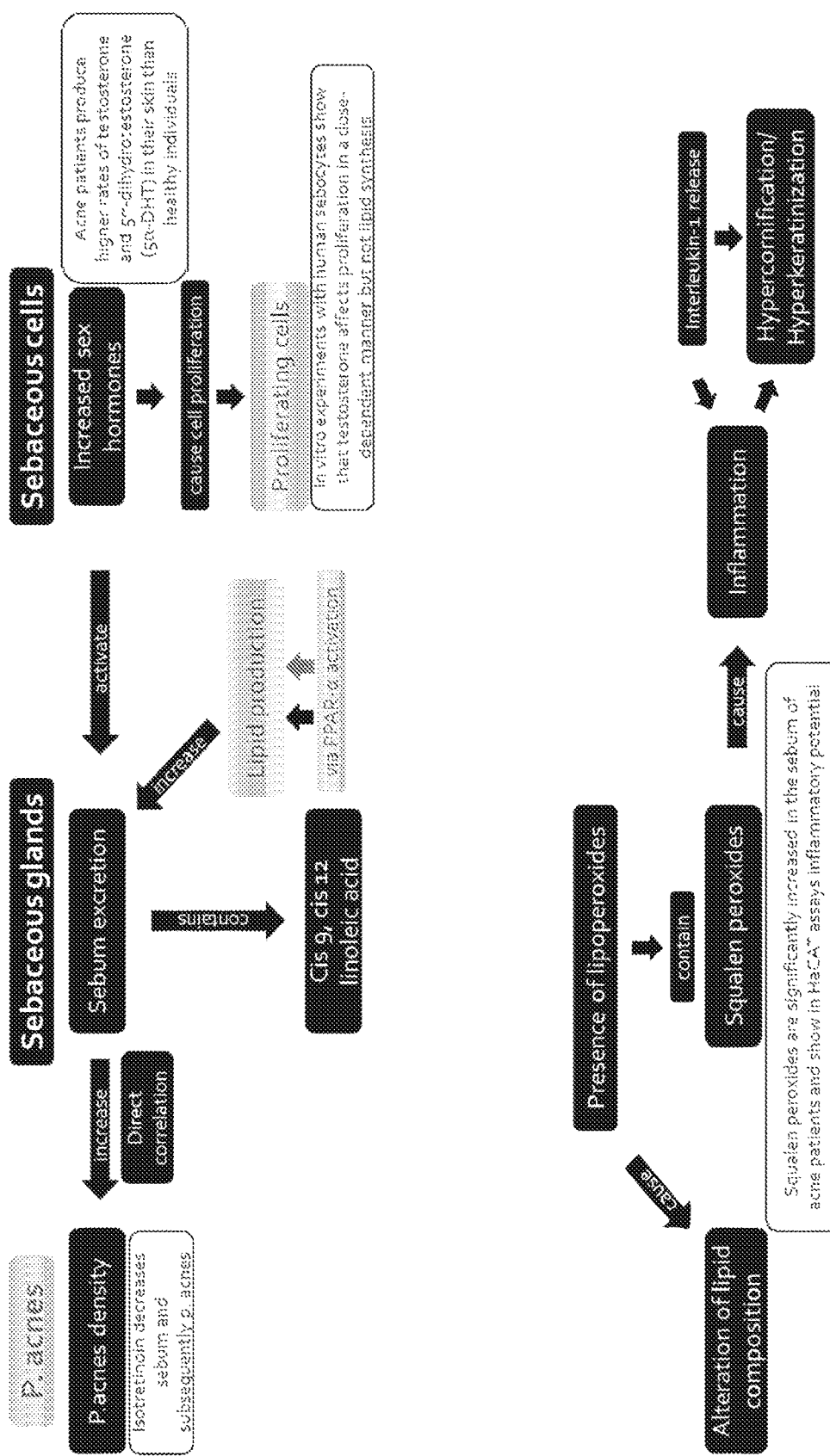
FIG. 4 depicts a flow chart identifying the current model for the onset of acne. While multiple events are known to be involved, knowledge of connections between the events is missing. The initial trigger of the inflammation has not yet been identified.
Figure 5:
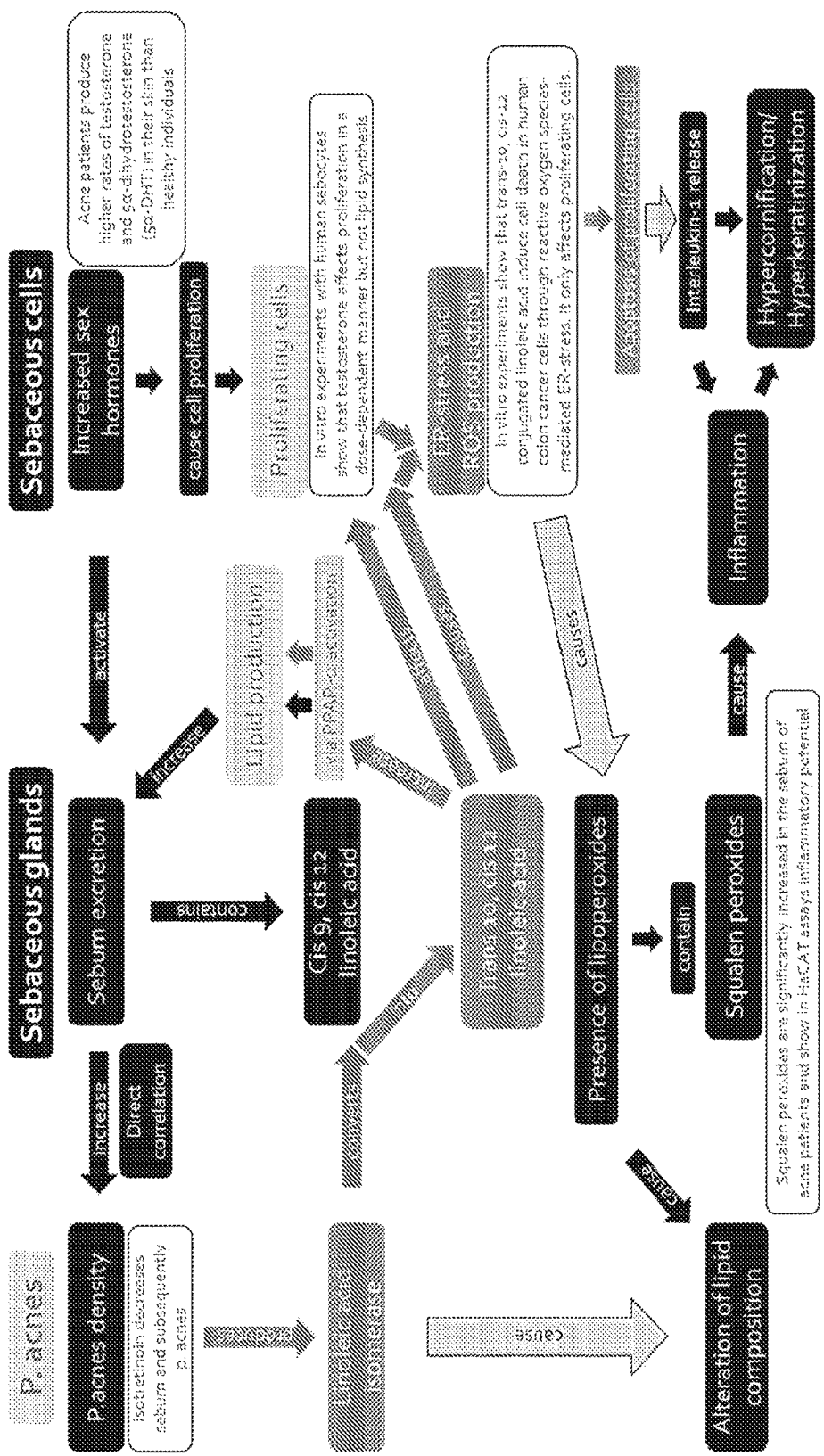
FIG. 5 depicts a proposed model for the onset of acne vulgaris, with trans-10, cis-12 linoleic acid produced by *P. acnes* as a connector between the different events in acne. Black boxes with white text indicate knowledge from acne research; dark gray boxes with white text indicate knowledge obtained from research on trans-10, cis-12 linoleic acid as food supplement; light gray boxes with gray text indicate knowledge in the art; and the three light gray arrows with black outlining indicate new connections disclosed herein, which allow for unification of the existing acne models. First a positive feedback loop between *P. acnes* colonization and increased production of sebum is established. Further the ER-stress induced by trans-10, cis-12 linoleic acid in proliferating cells and the subsequent apoptosis explains the initial triggering of the inflammation reaction. After the end of puberty, there is less proliferation in the sebaceous glands and the effect of trans-10, cis-12 linoleic acid is limited to the increase of sebum production.

Provided herein are compositions and methods for modulation of the skin microbiome. It is surprisingly demonstrated that the skin microbiome of a recipient can be modified to resemble the skin microbiome of a donor and that administration of compositions comprising live *P. acnes* bacterial strains can improve symptoms of acne. Compositions comprising one or more live bacterial strains are described herein for use in maintaining healthy skin, such as skin that is free of acne, or for treating or preventing acne. The live bacterial strains include one or more strains of *P. acnes*. As demonstrated herein, compositions comprising one or more live bacterial strains can help the human skin to revert microbiome disease states to healthy microbiome states.

Without wishing to be bound by any theory, it is proposed herein that *P. acnes* converts a signal precursor molecule (linoleic acid), which is naturally present in the sebum, to an active signaling molecule (trans-10, cis-12 linoleic acid), which stimulates in return sebum secretion, which is important for *P. acnes* colonization of the skin. Significantly, the production of this signaling molecule provides a connection between different aspects of the current understanding of the onset of acne.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having." "containing," "involving," and variations thereof herein, is meant to encompass the items listed thereafter and equivalents thereof as well as additional items.

Aspects of the invention relate to the microbiome. As used herein, "microbiome" refers to all of the microorganisms inhabiting the body. The human microbiome has a fundamental role in human health and disease (Consortium, 2012; NIH HMP Working Group et al., 2009). The development of Next Generation Sequencing (NGS) technologies has allowed the study of these microbial communities with an unprecedented depth and resolution (see Human Microbiota issue, Nature 2012). More than 10,000 different bacterial strains colonize the human body, and there are ten times more bacteria than human cells in an average human body. Recent research has indicated that the composition of bacterial communities in the body is tightly connected to the health of the human body (Belkaid and Segre, 2014: Consortium, 2012; Zhao, 2010). As a result, distortions of the microbiome are linked to a variety of diseases.

The gut microbiome, and methods for targeted manipulation of the gut microbiome, has been investigated in depth (Doré and Blottière, 2015). An example of such a therapy is the treatment of the antibiotic-resistant bacteria *Clostridium difficile* with the help of "fecal transplantation" (van Nood et al., 2013; Olle, 2013).

Following from research related to the gut microbiome, researchers recently began to investigate the skin microbiome (Belkaid and Segre, 2014; Oh et al., 2014). The skin is colonized by a large number of microorganisms, most of which are beneficial or harmless (Grice and Segre. 2011). However, diseases such as acne vulgaris are associated with strong alterations of the microbiome (Bek-Thomsen et al., 2008; Holmes, 2013; Kong et al., 2012). Acne, in particular, is considered to be linked to a distortion of the human skin microbiome (Fitz-Gibbon et al., 2013). This distortion is likely caused by a specific subset of the skin bacterium *P. acnes* (Lomholt and Kilian, 2010).

Herein, compositions and methods apply knowledge of the skin microbiome to develop treatments against skin disorders that originate or are influenced by distortions of the skin microbiome.

Acne

As used herein, "acne vulgaris" and "acne" are used interchangeably and refer to a skin condition that affects millions of people worldwide and is especially prevalent in teenagers. Acne is frequently associated with the formation of inflammatory and non-inflammatory lesions on the skin. Without wishing to be bound by any theory, acne may be associated, at least in part, with hair follicles that become clogged and/or inflamed. Acne is considered to be linked to the distortion of the human skin microbiome. This distortion may be caused by specific strains of the skin bacterium *P. acnes* (Fitz-Gibbon et al., 2013; Holmes. 2013; Lomholt and Kilian, 2010).

The development of acne is linked to the onset of sebum secretion from the sebaceous glands (Makrantonaki et al., 2011; Zouboulis, 2004). Also, the population density of *P. acnes* is directly linked to the amount of sebum produced (Kearney et al., 1984; King et al., 1982; Mourelatos et al., 2007). However, a clear molecular link between the presence of *P. acnes* and the disease acne, could until now, not be established. This is due, at least in part, to the fact that the skin of most adult humans is colonized by *P. acnes*, while symptoms of acne do not occur in many of those adults. In order for acne to occur, an inflammatory reaction must be triggered, which is accompanied by a change in the volume and composition of the sebum (Pappas et al., 2009).

Currently, standard treatment for acne is either long-term antibiotic treatment, such as treatment with Macrolide and/or Tetracycline antibiotics, or the systemic use of Isotretinoin (Berson et al., 2003). These treatments exhibit strong side effects and high relapse rates. For example, Isotretinoin causes skin irritation and also has teratogenic effects (causing birth defects) (McLane, 2001). In addition, the relapse rate with Isotretinoin is also unfavourable, at above 40% (Azoulay et al., 2007). Isotretinoin has been shown to reduce the volume of sebum production, thereby indirectly reducing the bacterial density on the skin (King et al., 1982). While antibiotics am a common treatment, in the last several decades, the number of bacterial strains that are resistant to one or more antibiotics has increased dramatically. (Leyden, 2001; Ross et al., 2001).

Another group of acne treatments include over-the-counter (OTC) products and cosmetics. Commonly used OTC products are broadband disinfection agents including benzoyl peroxide (e.g. Benzaknen, Galderma S. A., Lausanne, Switzerland and Aknefug, Dr. August Wolff GmbH & Co. KG Arzneimittel, Bielefeld. Germany) and salicylic acid. Additionally, there are a number of natural product lines which have limited or no proven efficacy.

Current therapies for skin disorders such as acne, that are linked to a distortion of the microbiome, are either ineffective or they are accompanied by severe side effects (McLane, 2001; Tripathi et al., 2013). Usually, the skin of a subject with acne improves during classical treatments, such as with antibiotics or hormones. However, the subject in most cases relapses after the end of the treatment. Isotretinoin has about a 41% relapse rate (Azoulay et al., 2007). Therefore, subjects are required to undergo long term treatments to keep the beneficial effects. This extreme relapse rate can be explained by the recolonization of the skin with the microbiome after stopping the therapy (FIG. 1).

Compositions and methods described herein address an unmet need for an effective treatment of acne without notable side effects, and with prevention of relapse. The novel approach described herein can involve transplantation of a healthy microbiome. Surprisingly, strains of *P. acnes*, the same bacterial species that is thought to be involved in causing acne, can be used to treat or prevent acne, or to maintain skin in a condition where it is free of acne. Described herein are compositions comprising one or more live bacterial strains that can provide an improved skin condition without causing notable side effects. The live bacterial strains within the compositions described herein are *P. acnes* bacterial strains.

In some embodiments, the composition is a cosmetic. As used herein, a "cosmetic" refers to a product that is intended to enhance appearance. Cosmetic composition comprising one or more live bacterial strains as described herein can also be referred to as a "cosmeceuticals" (Draelos, 2009).

Aspects of the invention relate to administering compositions comprising one or more live *P. acnes* bacterial strains to the skin of a subject either alone, in combination with other therapies, or following another therapy. In some aspects, a composition comprising one or more live *P. acnes* bacterial strains can help the skin revert from a microbiome disease state to a healthy microbiome state. In some embodiments, the skin of the subject has already been treated with a standard acne therapy, such as with antibiotics, disinfectants, or hormones. Compositions comprising one or more live *P. acnes* bacterial strains described herein can be used as complementary recovery methods to standard treatments for acne, whereby the composition comprising one or more live *P. acnes* bacterial strains can reduce the relapse rate of acne after antibiotic treatment. For example, a composition comprising one or more live *P. acnes* bacterial strains can be applied after an antibiotic or disinfectant treatment when the skin of a subject is cleared of the majority of its natural bacteria. The live bacteria in the composition can displace pathogenic bacterial strains and help to recover a diverse, healthy and balanced skin microbiome. Accordingly, in some embodiments, methods described herein involve eradicating pathogenic bacterial strains from the skin and then adding live *P. acnes* bacteria to the skin to create a healthy skin microbiome.

Compositions comprising one or more live *P. acnes* bacterial strains as described herein can be used to decrease or increase the volume of the sebum production of an individual. Compositions comprising one or more live *P. acnes* bacterial strains as described herein can also be used to produce trans-10, cis-12 linoleic acid in the follicles or sebaceous glands and thereby deliver this active compound to the environment of the sebaceous glands. These methods circumvent problems associated with the standard topical application of trans-10, cis-12 linoleic acid.

Compositions comprising one or more live *P. acnes* bacterial strains as described herein can also be used to increase or decrease the bacterial density on the skin by providing a bacterial strain to the skin which will increase or decrease the sebum production on the skin, thereby indirectly changing the bacterial density.

Compositions comprising one or more live *P. acnes* bacterial strains as described herein can also be used to modify the ratio of select bacterial species compared to other bacterial species or compared to other components of the microbiota such as fungi or mites by administering a live bacterial strain to the skin that alters the sebum production, thereby indirectly altering the bacterial density of *P. acnes* on the skin.

Compositions comprising one or more live *P. acnes* bacterial strains as described herein can be used to maintain healthy skin, such as skin that is free of acne. In some embodiments, administration of such compositions can assist in preventing formation of acne. In some embodiments, such compositions can be used to treat acne or can be used to prevent reoccurrence of acne in a subject who has received a standard acne treatment.

The compositions comprising one or more live *P. acnes* bacterial strains include one or more strains of live bacteria that naturally colonise the skin. In some embodiments, the one or more strains are naturally occurring. However, the composition comprising the one or more bacterial strains is not naturally occurring. The composition comprising the one or more bacterial strains has different properties than the individual strains in nature.

*Propionibacterium acnes* (*P. acnes*)

*P. acnes* is a species of anaerobic Gram-positive rod bacteria that is associated with acne as well as other conditions such as chronic blepharitis and endophthalmitis. *P. acnes* strains are present on the skin of most people. It has been reported that some strains of *P. acnes* are pathogenic, while other strains of *P. acnes* are not. (Fitz-Gibbon et al., 2013; Lomholt et al., 2010.) As used herein, "pathogenic" *P. acnes* strains refers to *P. acnes* strains that are associated with acne. Disclosed herein are assays by which pathogenic and non-pathogenic strains of *P. acnes* can be identified and selected.

Strains of *P. acnes* have been shown to differ significantly in their metabolism and phenotypic behavior (Lomholt and Kilian, 2010). These differences include but are not limited to expressing neuraminidase, α-glucosidase or hyaluronidase and the ability to perform hemolysis of horse blood, ribose fermentation, erythritol fermentation or sorbitol fermentation. Further it has been shown that *P. acnes* express an active linoleic acid isomerase, which specifically converts cis 9, c-12 linoleic acid into trans-10, cis-12 linoleic acid (Rosson et al., 2004). Linoleic acid is a key molecule in the regulation of sebum production and a reduction of linoleic acid has been linked in multiple studies to the onset of acne (Downing et al., 1986; Letawe et al., 1998).

Further it has been shown that *P. acnes* dead cells or supernatants are able to increase lipid production in hamster sebocytes (Iinuma et al., 2009a).

Species of *P. acnes* have been classified into types I-III, further including subtypes: IA and IB. (Lomholt et al.) IA has been further subdivide into $IA_1$ and $IA_2$ (McDowell et al., 2012). Genetic analysis of *P. acnes* strains has been conducted to determine which strains may be pathogenic and associated with acne, and which strains may be non-pathogenic and not associated with acne. (Fitz-Gibbon et al., 2013. Lomholt et al., 2010, and Kasimatis et al., 2013). In some embodiments, a non-pathogenic *P. acnes* strain is a strain from one of the following classes of *P. acnes*: I-2. II and IB. In some non-limiting embodiments, a non-pathogenic strain of *P. acnes* is selected from the group of non-pathogenic strains consisting of: D1. A5, C3. H1. H2. H3, K1, K2, K4, K6, K8. K9. L, and F4, as described in Scholz et al. (2014) PLOS ONE 9(8) e104199.

As described in Scholtz et al., and as would be understood by one ordinary skill in the art, strains of *P. acnes* can be identified using single-locus sequence typing (SLST), involving PCR amplification and DNA sequencing of a target locus. An SLST scheme for *P. acnes* was developed and described in Scholz et al. using the target locus PPA2385 A *P. acnes* database associated with the SLST scheme described in Scholtz et al. is available online at http://medbac.dk/slst/pacnes. Users can enter a *P. acnes* sequence into the online database to identify SLST fragments.

As used herein, "typing" a bacterial strain refers to identifying the bacterial strain, such as by using SLST. Table 1 in the Examples section lists allelic sequences used in SLST to identify strains described herein, such as *P. acnes* strains D1, A5, C3, H1, H2. H3. K1, K2, K4, K6, K8, K9, L1, and F4. One of ordinary skill in the art would understand the strain designations used herein, corresponding to those disclosed in Scholtz et al., and would understand how to identify whether a *P. acnes* strain corresponds to any of these specific strains by using, e.g., SLST.

Strains of *P. acnes* included in bacterial compositions described herein can be naturally occurring or can be genetically modified. Strains that are genetically modified can be modified by natural mutagenesis and/or by genetic engineering. In some embodiments, the genetic modification of the *P. acnes* strain increases or decreases its linoleic acid isomerase activity.

In some aspects, compositions comprising one or more live *P. acnes* bacterial strains described herein include the *P. acnes* strain H1 (6609). (Hunyadkürti et al.) The genome of this *P. acnes* strain has been sequenced and is available at GenBank accession number CP002815. (Hunyadkürti et al.) In some embodiments, compositions comprising one or more live *P. acnes* bacterial strains described herein include strains of *P. acnes* that have certain CRISPR/CAS9 sequences. (Brüggemann, 2012, Fitz-Gibbon 2013). In some embodiments, compositions comprising one or more live *P. acnes* bacterial strains described herein include comprise one or more of *P. acnes* strains K1. K4 and H1 (6609). In some embodiments, compositions comprising one or more live *P. acnes* bacterial strains described herein comprise each of *P. acnes* strains K1, K4, D1, A5, C3 and H1 (6609).

Bacterial compositions described herein comprise one or more strains of *P. acnes*. For example, a bacterial composition can comprise 1, 2, 3, 4, 5, 6, 7, 8, 9, 10, 11, 12, 13, 14, 15, 16, 17, 18, 19, 20 or more than 20 strains of *P. acnes*. One or more of the strains of *P. acnes* can be non-pathogenic strains. In some embodiments, all of the strains of *P. acnes* in a bacterial composition are non-pathogenic strains. In some embodiments strains of *P. acnes* are genotyped in order to identify the strain and to make a selection as to whether to include the strain in a composition. Strains of *P. acnes* included in bacterial compositions described herein can be selected to increase or decrease lipid production.

Aspects of the invention relate to mixtures of *P. acnes* strains. Selection of *P. acnes* strains can involve, at least in part, a determination of whether the strain is pathogenic. This determination can be based on public information, prior reports, and/or routine experimental testing to determine whether a *P. acnes* strain is pathogenic or not. In some embodiments, only non-pathogenic *P. acnes* strains are selected.

Selection of *P. acnes* strains can also involve, at least in part, a determination of which strains, or combinations of strains, are stable in conditions that would be appropriate for use in a cosmetic or pharmaceutical composition. In some embodiments, *P. acnes* strains that exhibit increased stability are selected. Stability can be assessed using methods known in the art, such as by measuring a change in colony-forming units (CFU). Strains of *P. acnes* included in bacterial compositions described herein can be naturally occurring or can be genetically modified. Strains that are genetically modified can be modified by natural mutagenesis and/or by genetic engineering. In some embodiments, the genetic modification of the *P. acnes* strain is made to influence the production of trans-10, cis-12 linoleic acid. In some embodiments, *P. acnes* strains show different level of linoleic acid isomerase, which can be used to classify bacterial strains and/or to select specific bacterial strains.

In some embodiments, one or more of the *P. acnes* bacterial strains is selected based on its ability to produce trans-10, cis-12 linoleic acid. In some embodiments, one or more of the *P. acnes* bacterial strains is selected based on the amount of trans-10, cis-12 linoleic acid it produces in its natural environment. In some embodiments, one or more of the *P. acnes* bacterial strains is selected based on the maximum concentration of trans-10, cis-12 linoleic acid it produces. In some embodiments, one or more of the *P. acnes* bacterial strains is selected based on the activity of the enzyme linoleic acid isomerase it produces. In some embodiments, a *P. acnes* strain with no linoleic acid activity is selected. In other embodiments, a *P. acnes* strain with low levels of linoleic acid activity is selected. In other embodiments, a *P. acnes* strain with high levels of linoleic acid activity is selected.

In some embodiments, production of trans-10, cis-12 linoleic acid by *P. acnes* strains is detected using methods described in and incorporated by reference from U.S. Pat. No. 6,743,609, entitled "Linoleate isomerase." which granted on Jun. 1, 2004. In some embodiments, the amount of trans-10, cis-12 linoleic acid produced is detected using FAME (Fatty acid methyl esters) and/or GC (Gas Chromatography).

In some embodiments, a *P. acnes* strain can convert from 500 pm linoleic acid up to 250 ppm trans-10, cis-12 linoleic acid and then can keep this concentration constant. In some embodiments, a *P. acnes* strain is selected that has higher capacity for conversion of linoleic acid to trans-10, cis-12 linoleic acid. In other embodiments, a *P. acnes* strain is selected that has lower capacity for conversion of linoleic acid to trans-10, cis-12 linoleic acid.

Without wishing to be bound by any theory, in some embodiments, a bacterial composition in which the *P. acnes* strains have zero to low levels of linoleic acid isomerase may be beneficial for preventing or treating acne because such compositions may reduce sebum secretion. In some embodiments, such a composition may be helpful in avoiding relapse of acne after finishing standard acne treatment (such as disinfection or antibiotics).

In some embodiments, bacterial compositions can be used to increase levels of trans-10, cis-12 linoleic acid in the skin follicles. In other embodiments, bacterial compositions can be used to decrease levels of trans-10, cis-12 linoleic acid in the skin follicles. In some embodiments, a combination of *P. acnes* strains is used to deliver trans-10, cis-12 linoleic acid directly to the sebaceous glands either for cosmetic or medical purposes.

In some embodiments, a bacterial composition described herein is used to reduce sebum production on skin that has high levels of sebum production, such as oily skin. In other embodiments, a bacterial composition described herein is used to increase sebum production on skin that has low levels of sebum production, such as dry skin. In some embodiments, a combination of strains with high linoleic acid isomerase activity is applied to the skin of individuals who lack sufficient sebum production. In some embodiments, such individuals are elderly people who may experience a decrease in sebum production.

In some embodiments, the amount of trans-10, cis-12 linoleic acid produced by a *P. acnes* strain is evaluated by comparing production of trans-10, cis-12 linoleic acid in the strain being tested to a *P. acnes* strain that is known not to produce trans-10, cis-12 linoleic acid or that produces negligible or lower than average amounts of trans-10, cis-12 linoleic acid. In other embodiments, the amount of trans-10, cis-12 linoleic acid produced by a *P. acnes* strain is evaluated by comparing production of trans-10, cis-12 linoleic acid in the strain being tested to a *P. acnes* strain that is known to produce average or higher than average amounts of trans-10, cis-12 linoleic acid. In some embodiments, the relative amount of trans-10, cis-12 linoleic acid produced is measured or evaluated. In other embodiments, the absolute amount of trans-10, cis-12 linoleic acid produced is measured or evaluated.

In some embodiments, the amount of cis-9, cis-12 linoleic acid degraded by a *P. acnes* strain is evaluated by comparing the degradation rate of cis-9, cis-12 linoleic acid in the strain being tested to a *P. acnes* strain that is known not to degrade cis-9, cis-12 linoleic acid or that degrades negligible or lower than average amounts of cis-9, cis-12 linoleic acid. In other embodiments, the amount of cis-9, cis-12 linoleic acid degraded by a *P. acnes* strain is evaluated by comparing degradation rate of cis-9, cis-12 linoleic acid in the strain being tested to a *P. acnes* strain that is known to have an average or higher degradation rate than average of cis-9, cis-12 linoleic acid. In some embodiments, the relative amount of cis-9, cis-12 linoleic acid degraded is measured or evaluated. In other embodiments, the absolute amount of cis-9, cis-12 linoleic acid degraded is measured or evaluated.

In some embodiments, one or more of the *P. acnes* bacterial strains within the composition exhibits slow or negligible degradation or conversion of cis-9, cis-12 linoleic acid. In some embodiments, all of the *P. acnes* bacterial strains within the composition exhibit slow or negligible degradation or conversion of cis-9, cis-12 linoleic acid.

In some embodiments, one or more of the *P. acnes* bacterial strains within the composition is selected based on its slow or negligible degradation or conversion of cis-9, cis-12 linoleic acid. In some embodiments, one or more of the *P. acnes* bacterial strains within the composition is selected based on the amount of cis-9, cis-12 linoleic acid it degrades in its natural environment. In some embodiments, one or more of the *P. acnes* bacterial strains within the composition is selected based on the maximum concentration of cis-9, cis-12 linoleic acid it degrades.

In some embodiments, one or more of the *P. acnes* bacterial strains within the composition is genetically modified to degrade less cis-9, cis-12 linoleic acid or to degrade cis-9, cis-12 linoleic acid more slowly.

Individual and combinations of strains can be tested using routine methods to determine which combinations lead to stable compositions. In some embodiments, such compositions are stable at room temperature for at least 1 week, 2, weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks or more than 30 weeks. In some embodiments, such compositions are stable at room temperature for at least 1 month. 2 months, 3 months, 4 months, 5 months, 6 months or more than 6 months.

In some embodiments, compositions are stable when refrigerated, at approximately 4° C. for at least 1 week. 2, weeks, 3 weeks, 4 weeks, 5 weeks, 6 weeks, 7 weeks. 8 weeks. 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks. 27 weeks. 28 weeks. 29 weeks. 30 weeks or more than 30 weeks. In some embodiments, compositions are stable when refrigerated, at approximately 4° C. for at least 1 month, 2 months, 3 months, 4 months, 5 months, 6 months or more than 6 months.

As discussed in Example 5, in some embodiments, a bacterial composition is formulated by taking a sample from the skin microbiome of a donor subject. For example, the sample can be taken from a subject who does not have acne. In other embodiments, a sample is taken from a subject who has mild, moderate or severe acne. In some embodiments, the sample is taken from a subject who has acne or is susceptible to acne, but bacterial strains associated with causing acne are removed from the sample. A sample can be cultured and can optionally be combined with other components to form a bacterial composition. In other embodiments, a bacterial composition can be formed from one or more isolated bacterial strains.

A sample taken from a donor subject can be tested to see if it contains non-pathogenic *P. acnes* strains. In some embodiments, one or more non-pathogenic *P. acnes* strains from the skin of a donor subject are selected and are administered to a recipient subject. The recipient subject can be the same subject as the donor subject or can be a different subject from the donor subject.

In some embodiments, a bacterial composition can include one or more strains of other bacteria, such as other non-pathogenic bacteria, in addition to one or more strains of *P. acnes*. In some embodiments, the one or more strains of other non-pathogenic bacteria have antibiotic properties. In some embodiments, a bacterial composition can include one or more *S. epidermidis* strains.

Linoleic Acid and its Isomer Trans 10, Cis 12 Linoleic Acid

Linoleic acid is a C18 fatty acid with two unsaturated double bonds. Usually, the main isomer is cis-9, cis-12. This isomer is also secreted as free fatty acid in the sebum. In vitro, linoleic acid stimulates the lipid production in sebocytes and may be involved in a feedback loop regulating sebum production. It also has antibacterial properties, with different *P. acnes* strains exhibiting different susceptibility to linoleic acid (Hong Lioe Ko et al., 1978; Madli Puhvel and Reisner, 1970). However linoleic acid also serves as a stimulant for sebum production, which represents the food source of *P. acnes*. Without wishing to be bound by any theory, an equilibrium may exist, represented by the linoleic acid concentration in the sebum determined by the bacterial population and the host's sebum production. This equilibrium depends on the degradation/conversion rate of cis, cis-12 linoleic acid by the *P. acnes* population colonizing the follicle.

Conjugated isomers of linoleic acid, namely cis-9, cis-11 linoleic acid and trans-10, cis-12 linoleic acid, have attracted attention as food supplements (Churruca et al., 2009). Linoleic acid trans-10, cis 12 acts on the PPAR receptor family (peroxisome proliferator-activated receptor) (Moya-Camarena et al., 1999). Activation of PPAR-α activates lipid synthesis in epidermal skin models, including cholesterol (Rivier et al., 2000). It has also been reported that trans-10, cis-12 linoleic acid increases ROS (reactive oxygen species) and has anticancer activity (Pierre et al., 2013).

*Staphylococcus epidermidis* (*S. epidermidis*)

*S. epidermidis* is a Gram-positive bacteria that is a normal component of human skin. *S. epidermidis* can produce 5 lantibiotics, including: epidermin, Pep5, epicidin 280, epilancin K7, and epidermicin NI01. A lantibiotic refers to an antibiotic-like peptide that contains the non-protein amino acids lanthionin and 3-methyllanthionine (Schnell et al., 1988). Epidermin is highly active against *P. acnes* (Allgaier et al., 1985). Gotz et al. describe epidermin in further detail. Wang et al. report that *S. epidermidis* can mediate fermentation of glycerol to inhibit the growth of *P. acnes*.

Strains of *S. epidermidis* included in bacterial compositions described herein can be naturally occurring or can be genetically modified. Strains that are genetically modified can be modified by natural mutagenesis and/or by genetic engineering. In some embodiments, the genetic modification of the *S. epidermidis* strain increases its antibiotic properties. In some aspects a bacterial composition can contain one or more strains of *P. acnes* and one or more strains of *S. epidermidis*. The one of more strains of *P. acnes* can be resistant to the antibiotic properties of the one or more strains of *S. epidermidis*. In some embodiments, the one or more strains of *P. acnes* are genetically modified to increase their resistance to antibiotic properties of one or more other bacterial strains, such as one or more strains of *S. epidermidis*. In some embodiments, the one or more *P. acnes* strains are modified by natural mutagenesis and/or by genetic engineering to increase their resistance to the antibiotic properties of one or more other bacterial strains.

In some embodiments, compositions comprising one or more live *P. acnes* bacterial strains described herein can contain one or more of an antibiotic, a disinfectant, or salicylic acid. One of ordinary skill in the art would appreciate that any antibiotic or disinfectant may be compatible with certain embodiments of the invention.

Skin Microbiome Transplantation

Aspects of the invention relate to modulation of a skin microbiome, such as by transplantation. Transplantation can occur between one or more subjects. In some embodiments, transplantation occurs in one subject and the same subject is the donor and the recipient. In other embodiments, transplantation occurs between two or more subjects. In some embodiment, there is one donor subject and one recipient subject. In other embodiments, there are multiple donor subjects and/or multiple recipient subjects. Multiple methods of transplantation can be used, resulting in different formulations of a bacterial composition. In some embodiments, a non-modified microbiome is transplanted, meaning that a donor microbiome is isolated, and prepared for delivery to a recipient. In other embodiments, a formulated microbiome is transplanted, meaning that a donor microbiome is isolated, optionally genotyped, and specific strains are selected for a formulation (e.g., strains with specific genotypes). In some embodiments a formulated and gene edited microbiome is transplanted, meaning that a donor microbiome is isolated, genotyped, specific strains are selected, genetic mutants are isolated from the strains, and a formulation is generated.

In some embodiments, methods comprise: obtaining one or more live bacterial strains from the skin of a donor subject, wherein the live bacterial strains are P. acnes strains; determining whether the one or more live bacterial strains are pathogenic; and administering the one or more live bacterial strains to the skin of a recipient subject in need thereof following administration of a disinfectant or antibiotic to the skin of the subject if the one or more live bacterial strains are not pathogenic. In some embodiments, an assay is conducted to determine whether the one or more live P. acnes strains are pathogenic. For example, an assay can be conducted to assess how the live bacterial strains convert or degrade cis-9, cis-12 linoleic acid. In some embodiments, one or more of the P. acnes bacterial strains within the composition is selected based on its slow or negligible degradation or conversion of cis-9, cis-12 linoleic acid.

Treatment

As used herein, the term treat, treated, or treating when used with respect to a disorder such as acne refers to improving at least one symptom of acne, such as a reduction or improvement of lesions associated with acne. As used herein, preventing acne refers to preventing formation of symptoms of acne such as lesions, and/or preventing at least one symptom of acne from getting worse, such as preventing further lesions or preventing existing lesions from becoming worse.

Subjects

Compositions described herein can be administered to human or non-human subjects. In some embodiments, a subject is a human or non-human who has acne or is at risk of developing acne. In some embodiments, the subject is a human. In some embodiments, the subject is a domestic animal such as a house pet, such as a cat or a dog. In some embodiments, the subject is a farm animal such as a cow, goat, horse, pig or sheep. It should be appreciated that any animal that has skin could be compatible with aspects of the invention.

Effective Amounts

Compositions described herein can be administered in effective amounts. The term "effective amount" of a composition of the invention refers to the amount necessary or sufficient to realize a desired biologic effect. For example, an effective amount of a composition for treating acne is that amount sufficient to improve at least one symptom of acne, such as a reduction or improvement in lesions. The effective amount for any particular application can vary depending on such factors as the condition being treated, the particular composition being administered, the size of the subject, or the severity of the condition. One of ordinary skill in the art can empirically determine the effective amount of a particular composition of the invention without necessitating undue experimentation.

Compositions

Compositions, including cosmetic or pharmaceutical compositions, for topical administration, include transdermal patches, ointments, lotions, creams, gels, drops, sprays, including aerosol sprays, suppositories, liquids, serums or powders. In some embodiments, the preparation is a two-component dispensing system. In addition, conventional pharmaceutical carriers, aqueous, powder or oily bases, or thickeners may be used in pharmaceutical preparations for topical administration. Examples of such ingredients include various hydroxylated compounds, such as monomeric glycols, e.g., propylene glycol, ethyl alcohol, glycerin and butylene glycol, polymeric moisturizers such as polyglycerylmethacrylate, derivatives of palmitates and stearates, triglycerides of fatty acids, lanolin, vegetable or mineral oils, and waxes.

In some embodiments, compositions include media for stabilizing bacterial count. Media can include pure water, PBS, peptone, and/or a diluted or undiluted version of a suitable growth medium or any combination thereof. In some embodiments, the bacterial composition is a gel containing a low percentage of peptone which assists in stabilizing the bacteria. In some embodiments, the percentage of peptone in the bacterial composition is about 0.05% or about 0.1%. The percentage of peptone can range in some embodiments from 0.005%-1%. For example, the percentage of peptone can be about 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9 or 1.0%. In some embodiments, the percentage of peptone is less than 0.005%. In some embodiments, the percentage of peptone is greater than 1%. In other embodiments, a suitable growth medium us used in place of peptone.

In some embodiments, the composition contains a buffer component to help stabilize the pH. In some embodiments, the pH is between 4.5-8. For example, the pH can be approximately 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0, including any value in between. In some embodiments, the pH is approximately 7.0.

Non-limiting examples of buffers can include ACES, acetate. ADA, ammonium hydroxide, AMP (2-amino-2-methyl-1-propanol), AMPD (2-amino-2-methyl-1,3-propanediol), AMPSO, BES, BICINE, bis-tris, BIS-TRIS propane, borate, CABS, cacodylate, CAPS, CAPSO, carbonate (pK1), carbonate (pK2). CHES, citrate (pK1), citrate (pK2), citrate (pK3), DIPSO. EPPS, HEPPS, ethanolamine, formate, glycine (pK1), glycine (pK2), glycylglycine (pK1), glycylglycine (pK2), HEPBS, HEPES, HEPPSO, histidine, hydrazine, imidazole, malate (pK1), malate (pK2), maleate (pK1), maleate (pK2), MES, methylamine. MOBS, MOPS, MOPSO, phosphate (pK1), phosphate (pK2), phosphate (pK3), piperazine (pK1), piperazine (pK2), piperidine. PIPES, POPSO, propionate, pyridine, pyrophosphate, succinate (pK1), succinate (pK2), TABS, TAPS, TAPSO, taurine (AES), TES, tricine, triethanolamine (TEA), and Trizma (tris).

In some embodiments the formulation includes a thickener. Non-limiting examples of thickeners can include hydroxyethylcelluloses (e.g. Natrosol), starch, gums such as gum arabic, kaolin or other clays, hydrated aluminum silicate, fumed silica, carboxyvinyl polymer, sodium carboxymethyl cellulose or other cellulose derivatives, ethylene glycol monostearate and sodium alginates.

In some embodiments, the bacterial composition exhibits a stable CFU over at least three months at mom temperature. In some embodiments, the CFU count shortly fluctuates in the initial storage phase (e.g., 2 weeks) and then stabilizes.

In some embodiments, compositions comprise emollients such as those disclosed in an incorporated by reference from U.S. Pat. No. 5,525,336. Non-limiting examples of emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polthylene glycol, triethylene glycol, lanolin, sesame oil, coconut oil, arrachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate.

In some embodiments, a protein stabilizing agent such as those disclosed in an incorporated by reference from U.S. Pat. No. 5,525,336 is included in the composition. Non-limiting examples include glycerol, ethylenediaminetetraacetic acid, cysteine, and proteinase inhibitors such as leupeptin, pepstatin, antipain, and cystatin.

In some embodiments, a humectant such as those disclosed in an incorporated by reference from U.S. Pat. No. 5,525,336 is included in the composition. Non-limiting examples of humectants include glycerin, sorbitol, sodium 2-pyrrolidone-5-carboxylate, soluble collagen, dibutylphthalate, gelatin.

In some embodiments, an astringent agent such as those disclosed in an incorporated by reference from U.S. Pat. No. 5,525,336 is included in the composition. Non-limiting examples of astringent agents include arnica flowers or extracts thereof, lower alkyl alcohols, witch hazel, boric acid, lactic acid, methol, camphor, zinc phenol sulphonate, aluminum acetate, aluminum sulfate, and zinc chloride or sulfate.

In some embodiments, a pigment such as those disclosed in an incorporated by reference from U.S. Pat. No. 5,525,336 is included in the composition. Non-limiting examples of pigments include titanium dioxide, micas, iron oxides, barium lake, calcium lake, aluminum lake, bismuth oxychloride, zirconium lake and calcium oxides.

In some embodiments, a coloring agent such as those disclosed in an incorporated by reference from U.S. Pat. No. 5,525,336 is included in the composition. Non-limiting examples of coloring agent include shikonin, β-carotene, paprika, monascus, safflower red, safflower yellow, red cabbage color, purple sweet potato color, lycopene, cacao color, grape color, cochineal, lac color, beet red, hematein, Red. No. 215, Red. No. 218, Red. No. 223. Red. No. 225, Orange No. 201, Orange No. 206, Yellow No. 201, Green No. 202, and Purple No. 201, Red. No. 2, Red. No. 3, Red. No. 102, Red. No. 104 (1), Red. No. 105 (1), Red. No. 106, Yellow No. 4, Yellow No. 5, Green No. 3, Blue No. 1, Blue No. 2, Red. No. 201, Red. No. 213, Red. No. 214, Red. No. 227, Red. No. 230 (1), Red. No. 230 (2), Red. No. 231, Red. No. 232, Orange No. 205, Orange No. 207, Yellow No. 202 (1), Yellow No. 202 (2), Yellow No. 203, Green No. 201, Green No. 204, Green No. 205, Blue No. 202, Blue No. 203, Blue No. 205, and Brown No. 201.

In some embodiments, UV-A and UV-B radiation filters, sunscreens, free-radical blockers, vitamin extracts, or antioxidants such as those disclosed in an incorporated by reference from U.S. Pat. No. 5,525,336 are included in compositions.

In some embodiments, a surfactant or a solvent such as those disclosed in an incorporated by reference from U.S. Pat. No. 5,525,336 is included in the composition. Non-limiting examples of solvents include water, ethyl alcohol, toluene, methylene chloride, isopropanol, n-butyl alcohol, castor oil, ethylene glycol monoethyl ether, diethylene glycol monobutyl ether, diethylene glycol monoethyl ether, dimethyl sulphoxide, dimethyl formamide and tetrahydrofuran, i) Anionic surfactants, such as metallic or alkanolamine salts of fatty acids for example sodium laurate and triethanolamine oleate; alkyl benzene sulphones, for example triethanolamine dodecyl benzene sulphonate; alkyl sulphates, for example sodium lauryl sulphate; alkyl ether sulphates, for example sodiumlauryl ether sulphate (2 to 8 EO); sulphosuccinates, for example sodium dioctyl sulphonsuccinate; monoglyceride sulphates, for example sodium glyceryl monostearate monosulphate; isothionates, for example sodium isothionate; methyl taurides, for example Igepon T; acylsarcosinates, for example sodium myristyl sarcosinate; acyl peptides, for example Maypons and lamepons; acyl lactylates, polyalkoxylated ether glycollates, for example trideceth-7 carboxylic acid; phosphates, for example sodium dilauryl phosphate; Cationic surfactants, such as amine salts, for example sapamin hydrochloride; quartenary ammonium salts, for example Quaternium 5, Quatemium 31 and Quaternium 18; Amphoteric surfactants, such as imidazol compounds, for example Miranol; N-alkyl amino acids, such as sodium cocaminopropionate and asparagine derivatives; betaines, for example cocamidopropylebetaine; Nonionic surfactants, such as fatty acid alkanolamides, for example oleic ethanolamide; esters or polyalcohols, for example Span; polyglycerol esters, for example that esterified with fatty acids and one or several OH groups; Polyalkoxylated derivatives, for example polyoxy:polyoxyethylene stearate; ethers, for example polyoxyethe lauryl ether, ester ethers, for example Tween; amine oxides, for example coconut and dodecyl dimethyl amine oxides. In some embodiments, more than one surfactant or solvent is included.

In some embodiments, preservatives, antiseptics, pigments or colorants, fragrances, masking agents, and carriers, such as water and lower alkyl, alcohols, such as those disclosed in an incorporated by reference from U.S. Pat. No. 5,525,336 are included in compositions.

In some embodiments wherein a composition is in a powder, the powders may include chalk, talc, fullers earth, colloidal silicon dioxide, sodium polyacrylate, tetra alkyl and/or trialkyl aryl ammonium smectites and chemically modified magnesium aluminum silicate as disclosed in an incorporated by reference from U.S. Pat. No. 5,525,336. In some embodiments, a composition can include a perfume.

When administered, the compositions of the invention are applied in a therapeutically effective, pharmaceutically acceptable amount as a pharmaceutically acceptable formulation. Any of the compositions of the present invention may be administered to the subject in a therapeutically effective dose. When administered to a subject, effective amounts will depend on the particular condition being treated and the desired outcome. A therapeutically effective dose may be determined by those of ordinary skill in the art, for instance, employing factors such as those described herein and using no more than routine experimentation.

In some embodiments, one or more of the following agents is included in compositions described herein: topical antibiotics (e.g., clindamycin, erythromycin, tetracycline, metronidazole), oral antibiotics (e.g., tetracycline, erythromycin, minocycline, doxycycline, clindamycin), topical retinoids (e.g., adapalene, tazarotene, tretinoin), oral retinoids (e.g., isotretinoin), benzoyl peroxide, salicylic acid, sulfur, azelaic acid, and antimicrobial peptides and derivatives thereof (e.g., lipohexapeptide HB1345, oligopeptide-10, magainins (e.g., pexiganan), protegrins (e.g., iseganan), indolicidins (e.g., omiganan. MBI 594AN), histatins (e.g., P113 P113D), human bactericidal/permeability-increasing proteins (e.g., XMP.629, neuprex), cathelicidins (e.g., cathelicidin-BF).

In some embodiments, compositions are administered in a topical form, such as in a cream or ointment. In some embodiments, administration of compositions described herein comprises part of a combination treatment or follows from an earlier treatment of the skin of a subject.

The appropriate amount of a composition to be applied can depend on many different factors and can be determined by one of ordinary skill in the art through routine experimentation. Several non-limiting factors that might be considered include biological activity and bioavailability of the agent, nature of the agent, mode of administration, half-life, and characteristics of the subject to be treated.

In some embodiments, the bacterial composition is not applied to subjects with sensitive skin. In some embodiments, when using a bacterial composition for the treatment or prevention of acne, the subject being treated avoids unnecessary sun exposure and uses a sunscreen. In some embodiments, if the treated skin is irritated, characterized by redness, swelling, burning, itching, or peeling, the product is used less frequently or in a lower concentration.

In some embodiments, a composition described herein is administered to the skin of a subject to maintain healthy skin. A composition can be administered once or multiple times. In some embodiments, a composition is administered at regular intervals while in other embodiments it is administered in irregular intervals. For example, a composition can be administered about every 15 minutes, 30 minutes, 1 hour, 2 hours, 3 hours, 4 hours, 5 hours, 6 hours, 7 hours, 8 hours, 9 hours, 10 hours. 11 hours, 12 hours, 24 hours, 48 hours, 3 days, 4 days, 5 days, 1 week, 2 weeks, 3 weeks, 4 weeks, 5 weeks, 6 weeks, 7 weeks, 8 weeks or more or less frequently including all values in between.

In some embodiments, a composition is administered to a subject who also receives or has previously received a standard acne treatment, such as a disinfectant or an antibiotic, as would be recognized by one of ordinary skill in the art. In some embodiments, the composition is administered in parallel with the standard acne treatment. In other embodiments, the composition is administered after the standard acne treatment. The composition can be administered either immediately after the previous treatment or there can be a delay between the previous treatment and administration of the composition. The composition can be administered once or multiple times after the previous treatment. In some embodiments, a composition is administered at regular intervals after the previous treatment while in other embodiments it is administered in irregular intervals after the previous treatment. For example, a composition can be administered about every 15 minutes, 30 minutes, 1 hour. 2 hours, 3 hours, 4 hours. 5 hours, 6 hours. 7 hours, 8 hours. 9 hours, 10 hours. 11 hours, 12 hours, 24 hours. 48 hours, 3 days, 4 days, 5 days. 1 week, 2 weeks, 3 weeks, 4 weeks, 5 weeks, 6 weeks, 7 weeks, 8 weeks or more or less frequently including all values in between after a previous treatment.

Aspects of the invention encompass mutating bacterial strains, such as in *S. epidermis* strains. Mutations can be made in some embodiments by selecting an amino acid substitution, or by random mutagenesis of a selected site in a nucleic acid or polypeptide. Variant polypeptides can be expressed and tested for one or more activities to determine whether a mutation provides a variant polypeptide with desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a gene or cDNA clone to enhance expression of the polypeptide. The activity of variant polypeptides can be tested by cloning the gene encoding the variant polypeptide into a bacterial or eukaryotic expression vector, introducing the vector into an appropriate host cell, expressing the variant polypeptide, and testing for a functional capability of the polypeptides as disclosed herein.

Bacterial cells according to the invention can be cultured in a variety of media, including rich or minimal media. As would be understood by one of ordinary skill in the art, routine optimization would allow for use of a variety of types of media. Media can be supplemented with various additional components, including sugar sources. Some non-limiting examples of supplemental components include glucose, amino acids, antibiotics and ATCC Trace Mineral Supplement. Similarly, other aspects of the medium, and growth conditions of the cells of the invention can be optimized through routine experimentation. For example, pH, temperature, and concentration of components within the compositions are non-limiting examples of factors which can be optimized.

Liquid and/or solid cultures used to grow cells associated with the invention can be housed in any of the culture vessels known and used in the art.

Kits

The present invention also provides any of the above-mentioned compositions in kits. In some embodiments, a kit comprises a container housing live bacteria or a container housing freeze-dried live bacteria. Kits can include a second container including media such as peptone. Kits can also include instructions for administering the composition. In certain embodiments, instructions are provided for mixing the bacterial strains with other components of the composition. In some embodiments, a kit further includes an applicator to apply the bacterial composition to a subject.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1: Compositions Comprising Live Bacteria for Topical Administration to the Skin A mixture of biologically active live bacteria for topical administration was prepared as follows. A sample of skin microbiome was taken from a donor. The sample was then cultured in the laboratory, and a formulation was prepared.

Methods for analysing the microbiome included DNA isolation, 16S amplification and large-scale amplicon sequencing, as well as bioinformatics for the taxonomic assignment and quantification of diversity in microbial communities. Steps included:
1. Isolation of bacterial strains from a donor. Bacteria were collected using swabs.
2. Growth in the laboratory. Bacteria were grown in reinforced *clostridium* agar in anaerobic conditions at 37° C.

3. Isolation and manipulation of the bacterial strains. The sample was enriched for *Propionibacterium* strains and analyzed for positive genotypes with SLST primers.
4. Formulation of a composition comprising one or more live bacterial strains. Bacteria were collected from an agar plate using a saline solution.
5. Application of the composition comprising one or more live bacterial strains to the recipient. The donor microbiome was applied using swabs.
6. Genotyping of the modified recipient microbiome, using an NGS-based genotyping approach discussed below.

An NGS-based genotyping approach was used for identifying different strains as follows:
1. The microbiome was collected using swabs
2. The sample was incubated at high temperature to isolate the DNA. The QuickExtract™ kit from Epicentre. Chicago, Ill, was used with some modifications. 80 microliters of 0.05M NaOH was added to the suspension solution. The incubation was conducted for 45 minutes at 60° C. followed by a 5 minute incubation at 95° C. After incubation, 9.2 microliters of 1 M Tris-HCl, pH 7.0 was added. 0.5 microliters of this mixture was used for PCR.
3. PCR was conducted on the sample using 16S primers, and SLST allele to characterize the population. DNA preparation was diluted 100× for PCR analysis. Samples were amplified using KAPA polymerase (5 min 95° C.; 35 cycles of (98° C. 20 s, 62° C. 25 s, 72° C. 30 s); 1 min 72° C.
4. Library preparation. The library was constructed using two rounds of PCR. The first round used 16S primers and SLST primers which included sequences compatible with Illumina sequencing. The second round was used to barcode the different samples for sequencing in a single Illumina flowcell.
5. Illumina MiSeq sequencing was conducted.
6. Samples were analyzed using an internally developed computational pipeline (S-genotyping). Quality filtering; samples were mapped into an internal database using bwa software. Data processing was conducted with R statistical language and results visualization.

Example 2: Storage of Compositions of *P. acnes* Strains

The *P. acnes* strain 6609 was grown in reinforced clostridial medium as liquid culture. After 2 days, the culture was spun down and washed with PBS and then with water as a final wash. Then the culture was resuspended in pure water and aliquoted into samples. A concentrated solution of the additives tested, e.g., peptone or 10×PBS was added to the bacterial suspension. Then the aliquots were stored either at room temperature or at 4° C. In both cases, they were protected from sunlight.

In regular intervals, about every 3-4 days, a dilution series of each sample was taken and the colony-forming unit (CFU) count was determined. The suspension was vortexed and a serial dilution was prepared. To determine the CFU count, aliquots of the dilution were added on an agar plate suitable for growth of *P. acnes*. 10 µl of an appropriate dilution was added on an agar plate of reinforced clostridial medium. The 10 µl was placed as a drop on top of the plate and run down. This method allows the placement of up to 4 drops on the plate. (e.g., according to http://www.science-projects.com/serdil.htm). Each sample was determined in 4 technical replicates. After 3-4 days of anaerobic incubation, the colony numbers were counted (manually or using the software OpenCFU) and both the average and the standard deviation were determined. Thereby a profile of the colony forming units was monitored over time.

Figure 6:
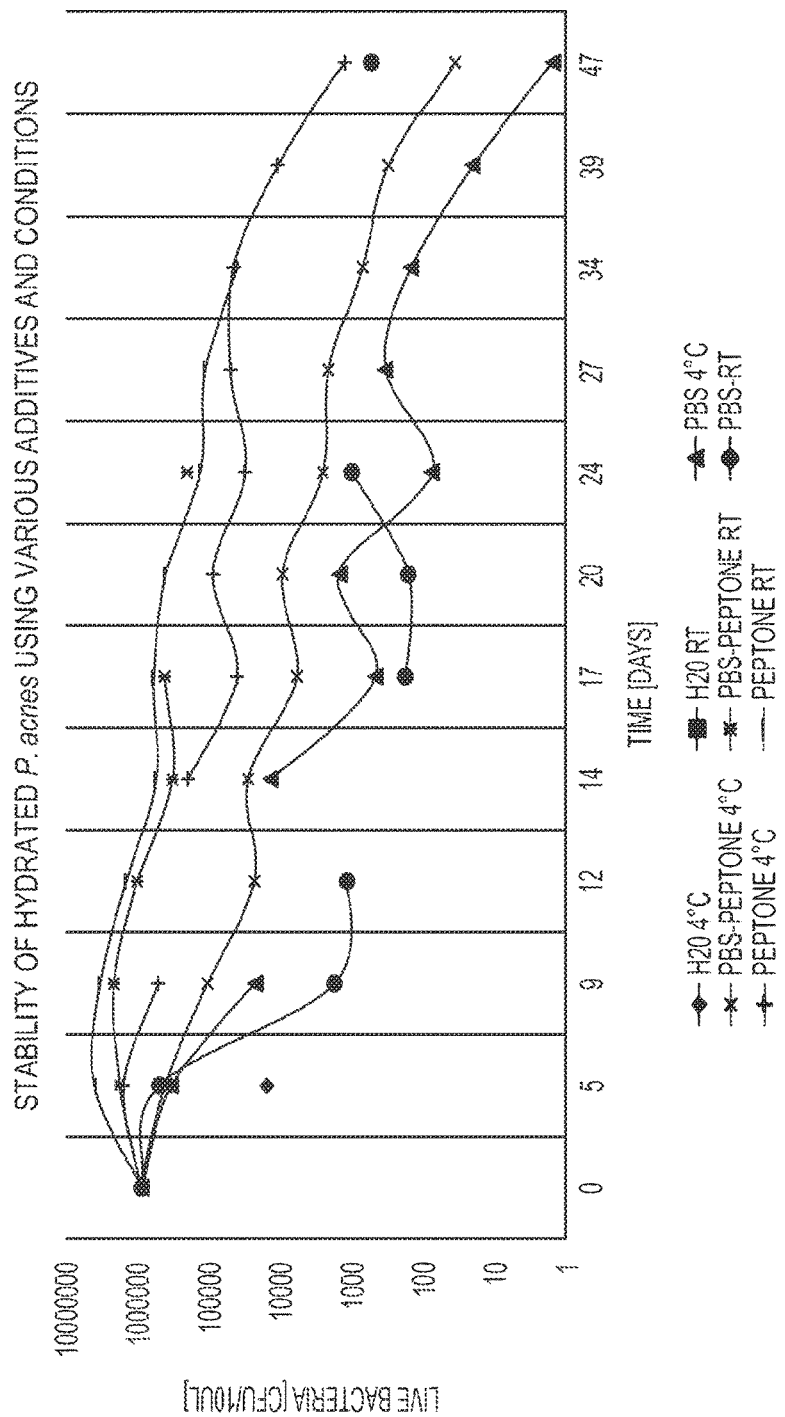
FIG. 6 depicts stability of hydrated *P. acnes* strain (H1) using various additives and conditions over 47 days. The most stable bacterial composition (stable counts of colony forming units (CFU)) include peptone and are stored at room temperature (RT). Other variations of bacterial compositions included water ($H_2O$) and PBS and were stored either at room temperature or at 4° C.
Figure 7:
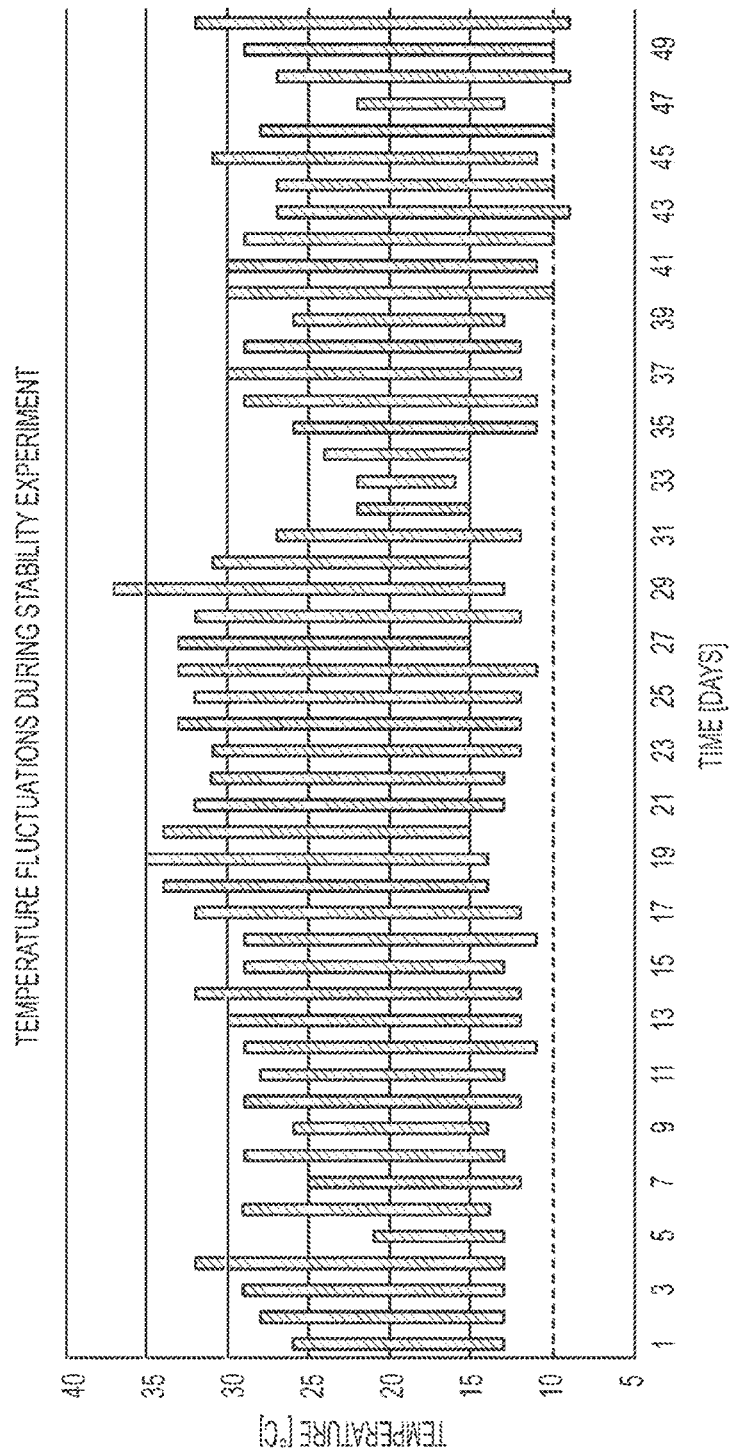
FIG. 7 depicts temperature fluctuations during the stability test. Samples marked as RT (room temperature) were stored in ambient temperature that varied during the test. Elevated temperatures are used in stability tests to predict long-term stability. If a product is stable at 45° C. for three months, then it is expected to be stable at room temperature for two years.

Additionally, bacteria of the skin microbiome were stabilized in a neutral liquid matrix for several weeks at ambient temperature varying between 15-35° C. (FIG. 7). It was demonstrated that *Propionibacteria* can survive months of storage, exposed to air, at temperatures between 15-35° C. when protected from light. Constant numbers of colony forming units (CFU) from a liquid matrix over months were also recovered (FIG. 6). To assess these numbers, methods that determine the CFU of liquids in a medium-throughput fashion were established as described below. It was shown that compositions were stable for at least 2.5 months.

Next, two vials with liquid bacterial suspension in 0.5% peptone were kept stored for over 6 months. One vial was clear and therefore the contained liquid was exposed to light. The second vial was protected from the light. Both vials were exposed to temperatures between −25° C. to 35° C. with the vast majority of the time being kept at room temperature. After 6 months, live bacteria were recovered from the vial protected from the light, while no live bacteria were recovered from the clear vial in which the bacteria were exposed to light. It is, accordingly, expected that bacterial compositions will be stable for at least three months when protected from light.

Example 3: Additional Components of Bacterial Compositions

Compatibility of compositions comprising one or more live bacterial strains with common cosmetic ingredients was also tested, e.g., Hyaluronic acid, inflammation inhibitors or moisturizers. If a tested common compound is beneficial for acne and is compatible with the compositions comprising one or more live bacterial strains, then it can in some embodiments, be added to the compositions comprising one or more live bacterial strains. However, the main active component within the compositions comprising one or more live bacterial strains is the live bacteria.

The formulations were optimized using in vitro assays. Cultures in plates containing disease microbiomes were treated with different formulations.

The Minimum Inhibitory Concentration Assay assessed the in vitro antimicrobial potency of the test compound. In this assay, the Minimum Inhibitory Concentration (MIC) was the lowest concentration of an agent that completely inhibited visible growth.

4 compounds were tested, which are commonly used in cosmetics or to treat acne for their effect on the growth of different *P. acnes* strains. The 4 tested compounds were glycolic acid, salicylic acid, lactic acid and hyaluronic acid. The first 3 are commonly used in products to treat acne, while the last one is a commonly used cosmetic compound. Any other compound can be tested the same way.

The test substance was dissolved in water or DMSO (for salicylic acid) and 4 µl of the test substance was added to 196 µl of growth medium resulting in the highest tested compound concentration. Then this concentration was diluted by 2-fold serial titrations, for a total of 11 concentrations and the final vehicle concentration was 2 percent. Following incubation, the test plate was visually examined and each well was scored for growth or complete inhibition of growth; then the MIC was recorded. Each test substance was evaluated in duplicate. Vehicle-control and an active reference agent (clindamycin) were used as blank and positive controls, respectively.

The following three strains were used to assess whether strain specific differences in the tolerance to these compounds could be observed:
Propionibacterium acnes (ATCC 11827)—A5
Propionibacterium acnes (ATCC 29399)
Propionibacterium acnes (ATCC 6919)—A1
The final concentrations for each tested compound were:
1. Salicylic acid: 0.3 M in DMSO (through 50× dilution by medium): 6000, 2000.600, 200, 60, 20, 6, 2, 0.6, 0.2 and 0.06 µM
2. Hyaluronic acid: 5 mg/ml 3 µM (through 50× dilution by medium): 60, 20, 6, 2, 0.6, 0.2, 0.06, 0.02, 0.006, 0.002 and 0.0006 nM
3. Lactic acid: 100% (13.4M): B, (through 50× dilution by medium): 2%, 0.6%, 0.2%, 0.06%, 0.02%, 0.006%, 0.002%, 0.0006%, 0.0002%, 0.00006% and 0.00002%
4. Glycolic acid: 9 M in water (through 50× dilution by medium): 180, 60, 18, 6, 1.8, 0.6, 0.18, 0.06, 0.018, 0.006 and 0.0018 mM For salicylic acid, the MIC was above the maximum water soluble concentrations (6 mM). For hyaluronic acid, the MIC was also above the highest tested concentration of 60 nM. A higher concentration of this compound could not be tested as the high viscosity of the stock solution becomes a limiting factor in the precise handling. These results were valid for all three strains. Therefore, these compounds could be added to a cosmetic formulation containing live bacteria.

For the compounds Glycolic acid and Lactic acid, inhibition of growth was observed at a concentration of 18 mM for the Strains ATCC 11827 and ATCC 6919 and 60 mM for the Strain ATCC 29399. The pattern for lactic acid was similar, with inhibition at 0.2% and 0.6% (FIG. 8). Accordingly, these compounds could be used as additives in lower concentrations. The results indicate strain-specific differences in susceptibility toward environmental changes. Other compounds that can enhance the compositions comprising one or more live bacterial strains, such as emollients, protein stabilizing agents, humectants, astringent agents, pigments, coloring agents, UV-A and UV-B radiation filters, surfactant of a solvent, preservatives, antiseptics, pigments or colorants, can be tested using the same methods.

Example 4: Compositions Comprising Staphylococcus epidermidis (S. epidermidis)

The skin bacteria S. epidermidis naturally produces a lantibiotic, epidermin. A lantibiotic refers to an antibiotic-like peptide that contains the non-protein amino acids lanthionin and 3-methyllanthionine (Schnell et al., 1988). This lantibiotic is highly active against P. acnes. Using random mutagenesis and a high-throughput selection assay, an S. epidermidis strain that has an increased production of epidermin or a production coupled to the presence of P. acnes is selected. The bacteria can mimic the effect of antibiotic therapy against acne as it actively produces antibiotic on the skin.

Additionally, evolutionary experiments are performed to select non-pathogenic P. acnes strains that are more resistant to epidermin. The modified S. epidermidis strain in conjunction with the resistant P. acnes strains are combined in some embodiments in a composition comprising one or more live bacterial strains. Such P. acnes strains have an evolutionary advantage over other P. acnes strains living on the skin because of their resistance towards epidermin, which is produced by the modified S. epidermidis strain. The modified P. acnes strains are likely to replace the other P. acnes strains already living on the skin.

Example 5: Demonstration of a Skin Microbiome Transplantation

Described herein is demonstration of a novel method that can be used to change the bacterial composition of the microbiome of the skin. The skin microbiome of a donor subject was sampled and cultured in the laboratory. Then, this mixture of natural skin bacteria was applied to the skin of a recipient subject. The skin of the recipient subject had previously had its own skin bacteria eradicated by using a standard acne treatment method (e.g., antibiotics or disinfectant).

This method allows the sampling of the skin microbiome of a donor subject to be cultured in the lab and separated into individuals strains. From the individuals strains, a healthy microbiome can be assembled by omitting, exchanging or adding certain strains. This new assembled microbiome can then be reapplied to the same subject or a different subject after the subject's own skin microbiome has been eradicated.

The skin microbiome of a donor subject was transplanted by using a commercial Copan Transystem® swab. Next, the donor subject's skin microbiome was cultured and expanded in the lab and then re-suspended in a neutral carrier liquid (saline solution). The donor subject's skin microbiome was applied to a previously disinfected area of skin on the recipient subject's skin. The skin had been disinfected with sterile gases and ethanol.

The complete microbiome of the recipient subject was sequenced at multiple time points before and after the transplantation using NGS Technologies (Illumina MiSeq). To avoid potential biases of the experiment, the skin area of the recipient subject was divided into four subareas. The first subarea was an untreated control region. The second was disinfected but not treated with bacteria. The third was disinfected and treated with the donor subject's skin microbiome. The fourth was disinfected and treated with a product from AOBiome as a control (AO+ Mist). The treatment was repeated three times and samples of the microbiome were taken in regular intervals, before each new application of bacterial mixture, to track the expected changes in the microbiome.

A 16S library was built to obtain a more generic view of the skin microbiome evolution, and also an SLST allele library to achieve detailed P. acnes strain monitoring. Specific alleles of each strain were amplified to monitor the presence and amount of each microorganism type.

A successful microbiome transplantation was measured from the donor subject to the recipient subject (FIG. 3). A generic 16S profiling transfer was seen from donor to recipient, and specific P. acnes strains were transferred from the donor subject to the recipient subject (FIGS. 3B, 3C). FIG. 3A shows a heatmap displaying the 16S repertoire after transplantation. After several days of application, the recipient subject's 16S profile became closer to the donor subject's 16S profile. FIG. 3B shows P. acnes strains transferred from the donor subject to the recipient subject. In the upper panel, the bar chart shows how some P. acnes strains populated the skin of the recipient. In the lower panel, a phylogenetic tree of the strains were analyzed (based on SLST alleles). FIG. 3C shows a detailed population of the different P. acnes strains in the donor subject, and in the recipient subject. FIG. 3D shows that the recipient subject's skin microbiome became more similar to the donor subject's skin microbiome after 3 days of application. Spearman correlation was used to measure the distance between different microbiomes.

Example 6: Clinical Study

A clinical study was conducted to validate dose response and stability for compositions comprising one or more live bacterial strains. The bacterial composition was tested on 18 healthy individuals over the time period of 11 weeks (which will be continued until a total of 16 weeks is reached). A dose response test to characterize the relationship between the amounts of bacteria applied to the skin and the colonization on the skin was conducted.

Study subjects were split into 3 arms, where each arm received bacterial mixtures consisting of 1 (H1). 2 (H1, A5) or 4 (H1. A5, D1, A1) live bacterial strains of *P. acnes*. Each mixture was applied in 3 dilutions (undiluted, concentrated 1:100, and 1:1000). Additionally, each subject was applied 3 dilutions of a donor microbiome cultured in the lab; CFU $10^4$/ml, CFU $10^6$/ml and CFU $10^8$/ml. In total, each subject was applied 6 different mixtures/dilutions and a blank formulation.

Bacterial mixtures were applied to the chest and back areas of each subject. These are areas that are rich in sebaceous glands, a natural habitat of *P. acnes*. Before application of bacterial mixtures, samples of the subject's microbiome were collected using swab and strip method. Application of bacterial mixtures was repeated 3 times, on day 1, day 2 and day 3. Measurement of microbiome samples was repeated on day 1, day 2, day 3 (before bacterial application), day 5, 8, 10, 12, 17, 24, 38, 52, and 66 (samples will also be collected at days 80 and 108). Applications/transplantation were conducted as described in Example 5.

Two different methods of sampling were used. The tested areas were sampled either using epicenter buccal swabs in combination with the extract N' amp kit from Sigma (Product no. XNAP2) following the procedure described by (Flores et al., 2012) which is herein incorporated by reference in its entirety. Alternatively, the 3 S Biokit (Skin surface Technology) was used, which allows sampling of both bacterial populations on the skin and also in the follicle sebaceous glands. The majority of the *P. acnes* population lives in the sebaceous glands and therefore such a sampling is superior to skin swabs while still being minimally invasive.

The swab samples were processed as described and stored at −20° C. until PCR amplification. After sampling, the strips were stored in 50 ml falcon tubes at −80° C. until further processing. On the day of processing, the samples were thawed in the morning. After reaching room temperature, a disk with 6 mm diameter was cut out of the strip using Harris Uni-Core Punch 6 mm, (WB100082). This disk was put in a 2 ml tube and 80 μl 0.05M NaoH+20 μl water were added. The sample was vortexed and then incubated for 45 min at 60° C., then vortexed again and spun down. After this, the samples were stored at −20° C. until further processing. Before the first amplification of the typing regions, the samples were purified using Serapure beads which were made as described by (Rohland and Reich, 2012). A 1:1 ratio of bead solution volume to the sample volume was used for the DNA purification step. The purified DNA was then used as template in the subsequent PCR.

For PCR amplification, either polymerase provided by Sigma extract N' amp kit or a Kappa HIFI ready mix (product no. 07-KK2601-02) were used. For the Kappa reaction, the maximum volume of purified DNA template was used (11.5 μl in a 25 μl reaction). The Sigma protocol was not changed.

The amplification protocols were as follows: SLST Kappa Cycling: 3 min @95° C., 35× cycles, 20 s @98° C., 15 s @ 62° C., 30 s @ 72° C., 1 min @72° C., 4° C. (hold). For the amplification of the 16S amplicon, the recommended protocol from Illumina was used.

After amplification, the samples were indexed using the suggested protocol by Illumina and pooled for sequencing on a MiSeq with v3 chemistry yielding 2*300 bp reads Additionally, skin irritation and sensitivity to bacterial compositions in healthy individuals were evaluated. No skin irritation or sensitivity linked to the application of compositions comprising one or more live bacterial strains was recorded.

Microbiome differences were computed by comparing the vectors that describe the microbiome. Each position of the vector contains a number indicating the number of times that a certain strain was detected. Correlation distance was used to measure differences between different microbiomes.

Figure 15:
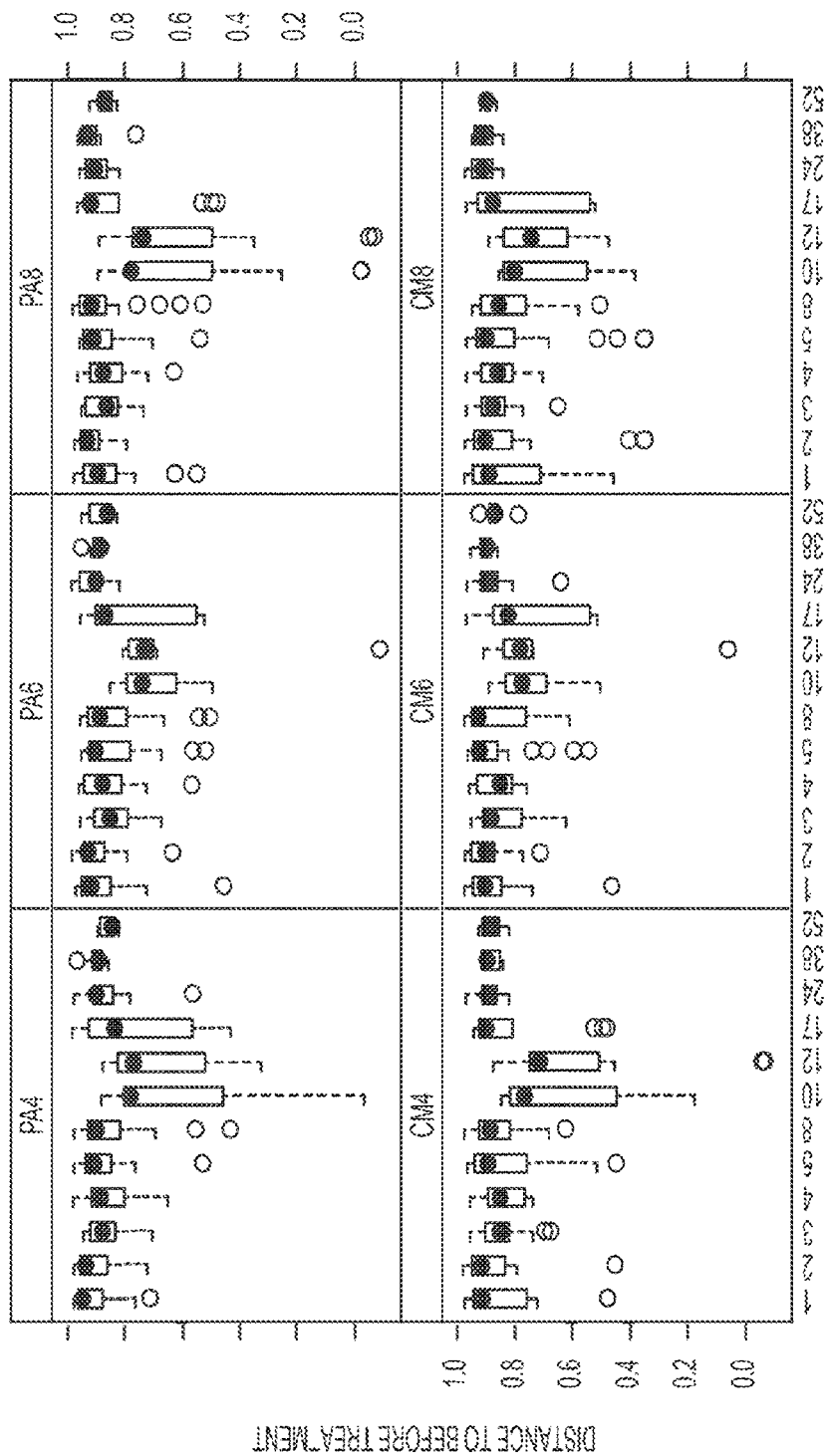
FIG. 15 depicts treatment durability effects of bacterial compositions. The six different formulations were tested for durability. *P. acnes* population in areas treated with the formulations and with an empty solution were compared at several days during and after treatment (18 patients). Comparison is carried out by measuring spearman correlation between *P. acnes* population in the treated area, and the untreated area. Treatment effects take a few days to alter microbiome composition and last for 2-3 weeks.

Results of durability of the microbiome and the dose response are shown in FIG. 15. A strong effect of the different treatments on the composition of the microbiome was observed, which was absent in the control areas treated with the vehicle only. The treatment effects took a few days to alter the microbiome composition. After this initial period, the changes lasted without additional application of bacteria for 2-3 weeks.

An effect of the CFU dose of bacteria applied to the patient was observed. This effect is mostly present in the first 5 days of the experiment and the observed differences disappear in the long term observation. This result proved that the composition of the microbiome can be changed even on the *P. acnes* strain level. It also showed that a moderate dose dependency exists between the outcome of the microbiome transplantation and the applied CFU. These data also indicated that the skin microbiome has a tendency to revert to its original state after such a transplantation. This was expected due to the fact that bacteria were only transplanted on small areas in this specific study, while these areas were still surrounded by a natural microbiome. It was a surprising outcome of this study that a distinct microbiome can be selectively established on a small part of the skin of a healthy person for 2-3 weeks until it is reverted to its original state by the surrounding microbiome.

Example 7: Administering Compositions Comprising One or More Live Bacterial Strains to a Subject A subject is identified as being in need of a composition comprising one or more live bacterial strains. In some instances, the composition comprising one or more live bacterial strains is used for the complementary treatment of acne in combination with, or without or following a prior standard of care acne treatment. A clinical study is conducted to evaluate the effect of administering a composition comprising one or more live bacterial strains to subjects with acne.

Initially, a pilot study was conducted. Compositions comprising 3 live bacterial strains (H1, K4 and K1) were tested on 10 subjects in the age range of 14-25 with facial acne vulgaris. The strains were isolated from healthy individuals and selected based on our meta-analysis of the literature. Study subjects were recruited and selected by a dermatologist. Visual evaluation by a dermatologist (lesion count) was done on day 1 to establish a baseline lesion count. Subjects were instructed to use a branded Benzoyl peroxide product for 7 days. At day 7, subjects were visually evaluated by a dermatologist and were instructed to use a composition comprising one or more live bacterial strains for the following 14 days. 2 times a day. At day 21, subjects were visually evaluated by the dermatologist.

According to dermatologist evaluation. 40% of subjects improved at evaluation week 1 (day 7)—at the end of the Benzoyl Peroxide application phase, 50% of subjects improved receiving a composition comprising one or more live bacterial strains at evaluation week 3 (day 21)—at the end of application of bacterial compositions, and 30% of subjects remained the same state (FIG. 9). Additionally, skin irritation was evaluated. 50% of subjects didn't experience any irritation. 30% showed slight irritation and 20% showed medium to high irritation.

Next, a clinical study is conducted in 50-100 subjects, ages 16-25 with mild to moderate acne vulgaris. Subjects are split into two arms where one arm follows the study design of the conducted pilot; e.g., an initial phase of Benzoyl peroxide application (7 days), then a phase of being administered a composition comprising one or more live bacterial strains twice daily (77 days) and then a follow-up phase (28 days) to evaluate relapse efficacy. Subjects in arm two, a control arm based on standard acne treatment or a vehicle, undergo a phase of Benzoyl peroxide treatment (7 days) and then either continue with Benzoyl peroxide or change to vehicle (77 days) with a follow-up phase (28 days).

Subjects are evaluated visually by a dermatologist (lesion count, irritation and sensitivity) and documented by imaging. Samples of microbiome are taken and self-perception evaluation is documented. Evaluations are conducted, e.g., on days 1, 28, 56, 84 and 112.

Example 8: Association of Trans-10, Cis-12 Linoleic Acid Produced by *P. acnes* with Increased Lipid Production in Sebaceous Glands Experiments were performed to show that trans-10, cis-12 linoleic acid triggers increased sebum production observed in acne. The model described by Iinuma et al., 2009b was used. Iinuma et al. showed that immortalized cell lines of sebocytes showed the same results as the isolated sebaceous glands (Iinuma et al., 2009b). Therefore, immortalized cell lines were used for the following experiment:
The sebocytes cell culture was stimulated with two samples:
  1. Linoleic acid,
  2. Trans-10, cis-12 linoleic acid,
Next, a sebocytes cell culture is stimulated with two more samples:
  3. Supernatant and fixed cells from a wild type *P. acnes* strain, and
  4. Supernatant and fixed cells from a mutant of the same strain as in #3 in which the isomerase gene is deleted by genetic modification.
The following parameters are measured at various time points after incubation of these cultures using commercially available kits which are publically available and known in the art:
  Total triglyceride content
  Reactive oxygen species
  Total protein content for normalization (commercial kit)
  Perform a final RNA-Seq experiment (outsourced to commercial provider)
Sebocytes Seb E6/E7 were cultured either in full media (Sebomed (Biochrome, product number F8205) supplemented with 10% FBS, Pen/strep and 5 ng/ml of EGF) or serum free media (500 ml of Sebomed media, Pen/strep, 5 ng/ml of EGF, 2.5 ml of Bovine Pituitary extract (Thermo Fischer order no 11568866) and 0.15 µM LA complexed in 1:1 molar ratio with BSA). Cells were detached using Accutase according to the manufacturer's instructions (Capricorn Scientific, product number ACC-1B). After detachment, cells were counted using Tali (Invitrogen) and a concentration of 40,000 cells were seeded per well. Cells were first seeded in full media. After 24 h, the full media was removed and the cells were exposed to different concentrations of cis-9, cis-12 linoleic acid and the trans-10, cis12 conjugated isomer. After 24 h of exposure, the serum free media was removed and full media containing the compounds in the same concentration was added to stimulate proliferation of the sebocytes. After 96 hours, the cell supernatants were analyzed for the presence of the enzyme lactate dehydrogenase (LDH), which indicates cell lysis, using a commercial assay according to the instructions of the manufacturer (Pierce, product number 88954). The cells which were still attached in the wells were assayed for metabolic activity using a commercial XTT assay (Thermo Fischer, product number X-6493).

Figure 10:
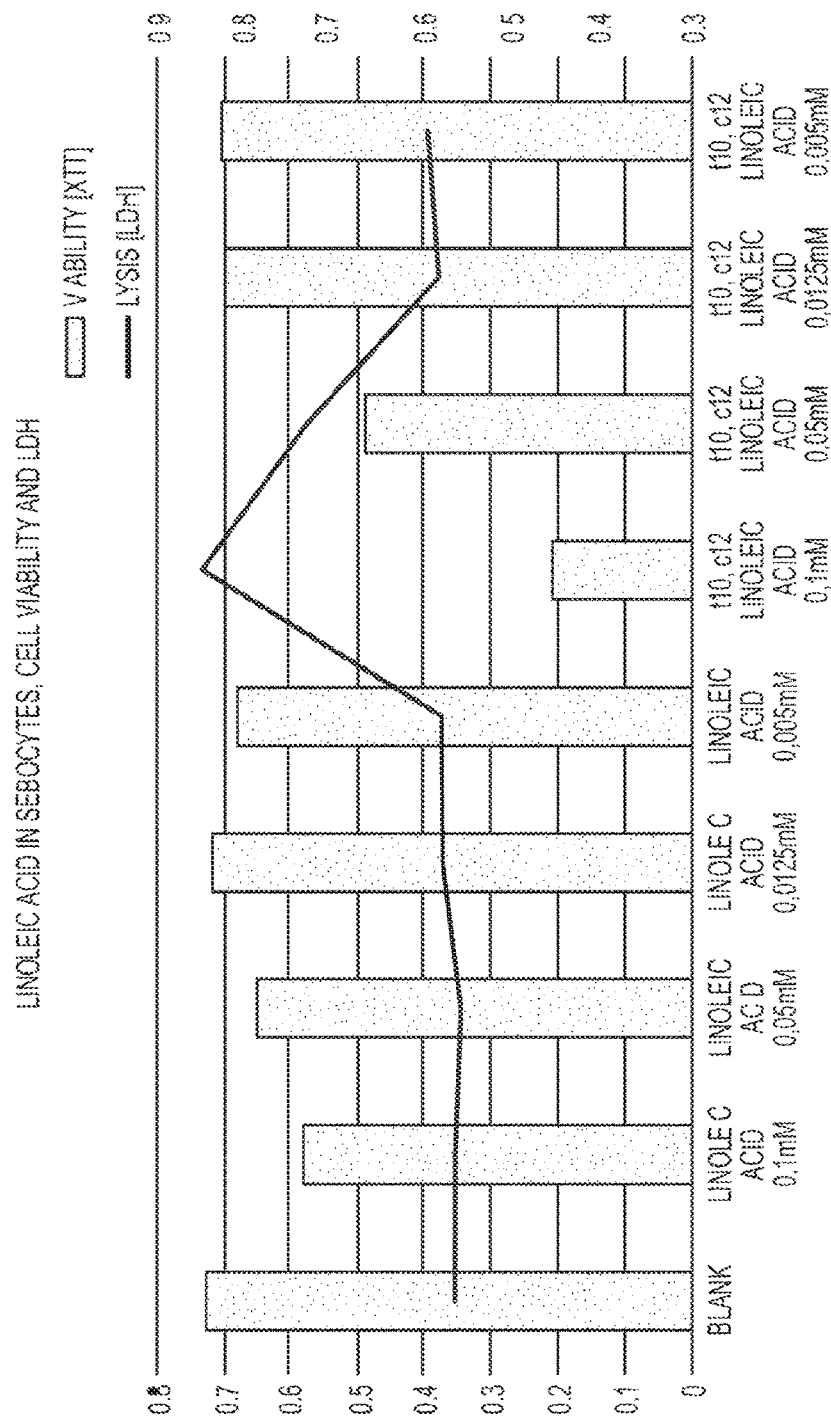
FIG. 10 depicts the viability and cell lysis of Seb E6/E7 sebocytes that was measured after 5 days of exposure to different concentrations of linoleic acid and its conjugated isomer t10, c12 linoleic acid. Commercial kits were used according to manufacturer instructions XTT assay (Thermo Fisher, product number X-6493) and LDH assays (Pierce, product number 88954).

A low metabolic activity in combination with a high LDH activity in the medium indicates a cytotoxic effect of the tested compound. The results are shown in FIG. 10. A clear dose-dependent cytotoxic effect of the conjugated isomer is visible, while no significant effect of the cis-9, cis 12 linoleic acid is present. All experiments were performed in triplicates.

Based on the known effect of trans-10, cis-12 linoleic acid on proliferating cells, it is reasonable to assume that the cytotoxic effect is caused by reactive oxygen species and ER-stress (Pierre et al., 2013). To test reactive oxygen species a molecular reactive oxygen marker is used such as Cell ROX from Thermo Fisher in combination with FACS analysis to quantify the extent of reactive oxygen species generation in sebocytes after stimulation with trans-10, cis 12 linoleic acid.

Figure 11:
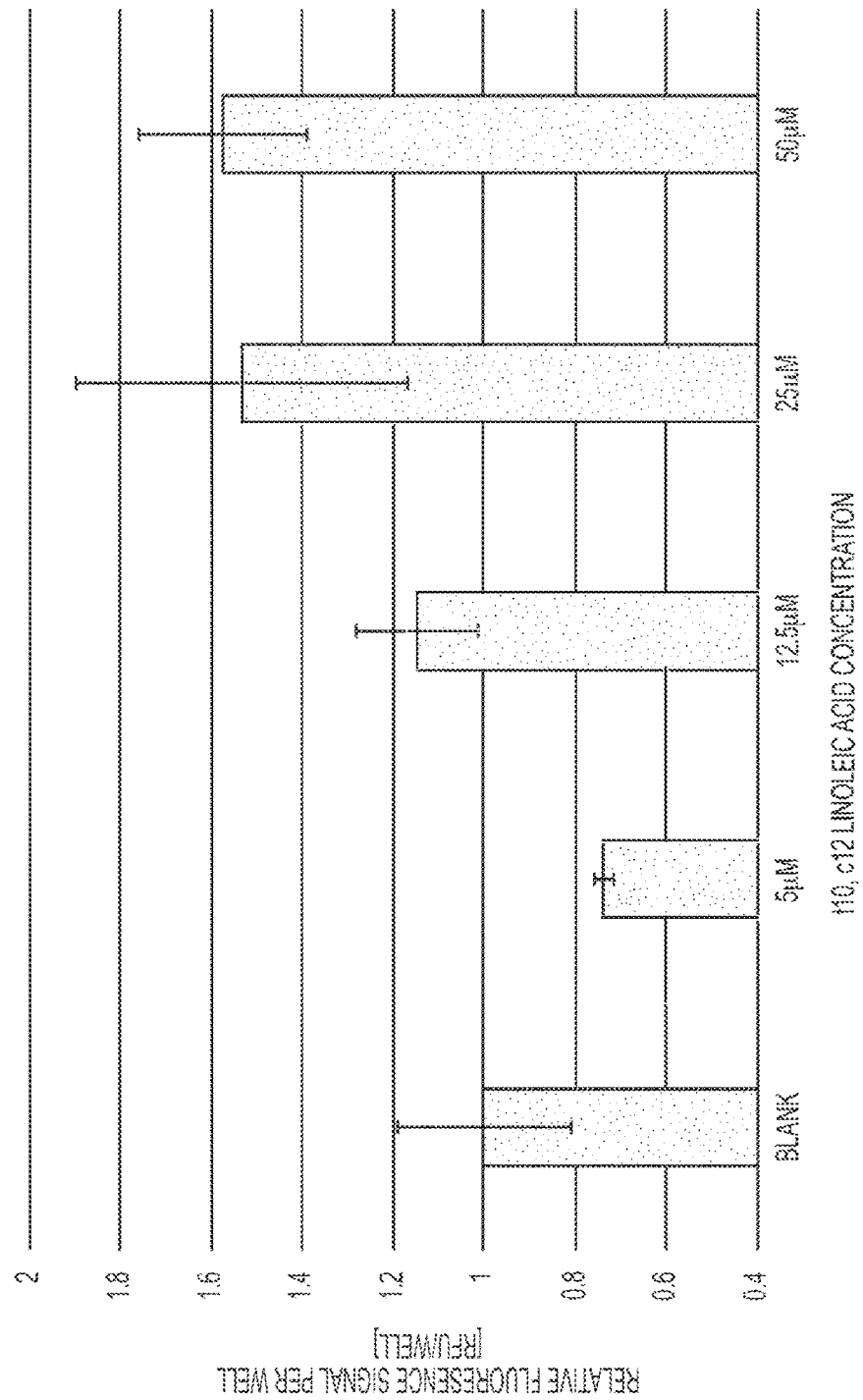
FIG. 11 shows the relative amount of neutral lipids stained with HCS LipidTOX reagent deep reed after a 72 h stimulation with varying concentrations of trans-10, cis 12 linoleic acid. An image at 5× magnification was taken from each well and then the relative fluorescence intensity quantified. Each condition was measured in triplicates. As a control, the cells were either unstimulated (blank) or stimulated with cis-9, cis-12 linoleic acid (not shown).

Seb E6/E7 cells, which were seeded in 96-well plates and stimulated as described above were then analyzed for the induction lipid production. After 72 h of stimulation, the cells were stained with HCS LipidTOX deep red neutral lipid stain from Thermo Fisher (product no. H34477) according to the manufacturer's instructions. A final dilution of 1:450 of HCS LipidTOX dye in PBS was used for the staining. The amount of fluorescence was then evaluated using an inverted fluorescence microscope. In one approach, a complete well was imaged at 5× magnification and the total fluorescence in the image was quantified. Each condition was analyzed in triplicates and the results are shown in FIG. 11. A clear dose-dependent induction of lipid production was seen. The magnitude was equal to that of cis-9, cis 12 linoleic acid, which is usually used as a control inducer for lipogenesis in sebocytes.

Figure 12:
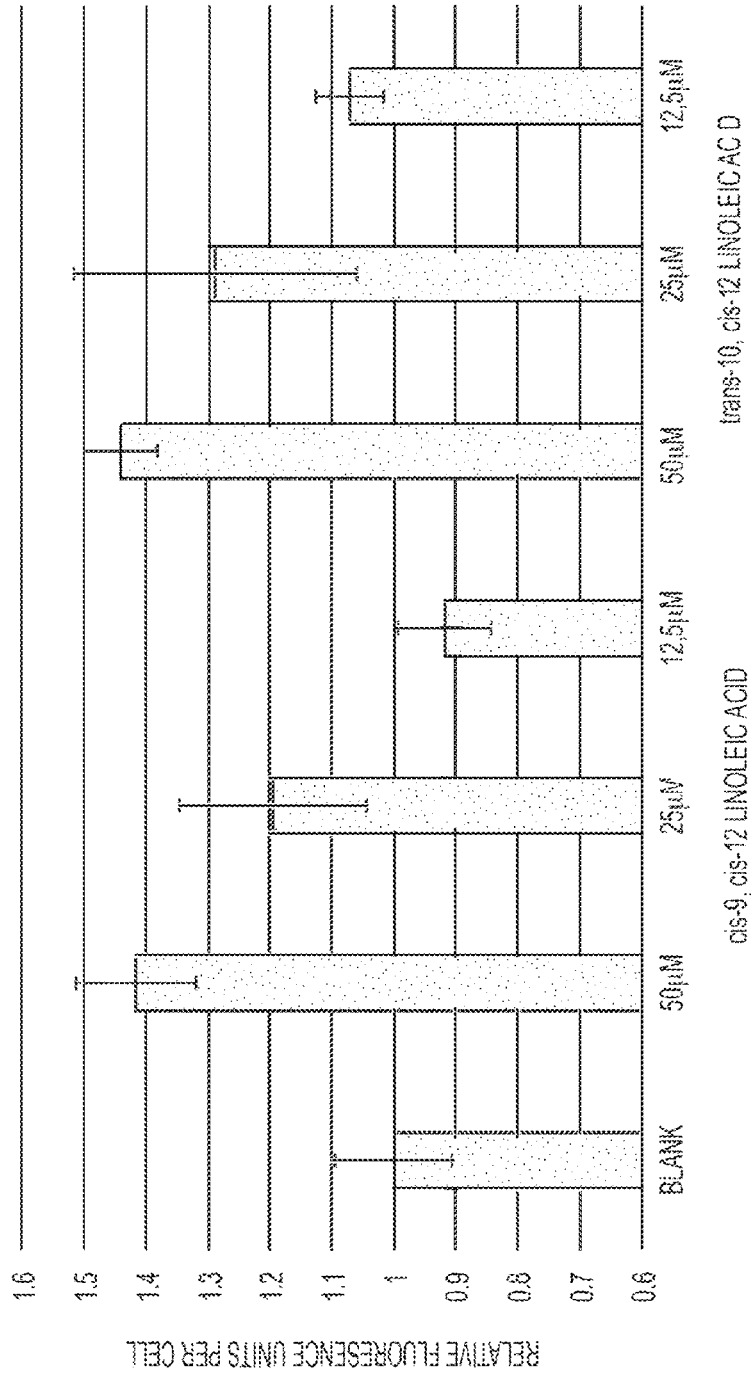
FIG. 12 shows the same experimental setup as in FIG. 11, except that for the evaluation, individual cells were randomly selected in the wells at a 20× magnification and then the relative fluorescence intensity was measured. As a negative control, a non-stimulated blank was used and as positive control, the cells were stimulated for lipogenesis with cis-9, cis-12 linoleic acid.

Alternatively, the fluorescent signal of individual cells, which were randomly selected from a higher magnification images, were quantified. 10 cells per image and 3 wells per condition were quantified. The average fluorescence intensity is shown in FIG. 12. With both analysis methods, a dose-dependent induction of lipogenesis through trans-10, cis 12 linoleic acid was observed. This result showed surprisingly that not only can cis-9, cis-12 linoleic acid induce lipogenesis in Sebocytes, but also the trans-10, cis-12 isomer. This was an unexpected finding as there is a pronounced different effect in the cytoxcity of the two molecules, indicating different target receptors. The fact that sebum production is regulated by holocrine secretion and the increased rate of cell lysis observed in the LDH assay, indicated surprisingly that trans-10, cis-12 linoleic acid is a regulator of sebum production in vivo.

Additionally, a knockout *P. acnes* strain is generated which lacks the linoleic acid isomerase gene. For this. *P. acnes* strain KPA171202 is used, which is the only strain for which a successful gene knockout has been described. A circular plasmid with 500 bp homology regions flanking an Erythromycin resistance gene is constructed as described in (Sörensen et al., 2010). As a homology region, the regions 500 bp upstream and downstream of linoleic acid isomerase gene KPA171202:PPA1039 are selected. This knockout will allow for the demonstration that the linoleic acid conversion of *P. acnes* is involved in the pathogenesis of acne vulgaris.

Example 9: Different *P. acnes* Strains have Different Levels of Linoleic Acid Isomerase Activity or Final Thresholds of Concentration of Trans-10, Cis-12 Linoleic Acid Experiments were performed to characterize the linoleic acid isomerase activity of different *P. acnes* strains. The *P. acnes* strains were grown in a growth medium lacking linoleic acid as described in the art (Rosson et al., 2004). Cis-9, cis-12 linoleic acid was added to the growth medium and then the amount of trans-10, cis-12 linoleic acid isomer formed was determined. To determine the amount of trans-10, cis-12 linoleic acid produced. FAME (Fatty acid methyl esters) and GC (Gas Chromatography) or HPLC (High Pressure Liquid Chromatography) were used. Established methods for distinguishing cis and trans isomers of unsaturated fatty acids are described in Kramer et al., 2004, which is herein incorporated by reference in its entirety.

*P. acnes* strains A1 and C3 were grown as starter cultures. The samples were spun down and the pellets were resuspended in PBS. The samples were normalized to an OD of 0.5 in PBS. 500 µl of this PBS suspension was used to start a culture in 15 ml RCM, which was supplemented with 1.7 mM cis-9, cis-12 linoleic acid and 0.17 mM oleic acid. The samples were left without shaking in the incubator at 37° C. and only vortexed before aliquots were taken. 2 ml aliquots were taken every ~24 h until $T_5$. All samples were stored at −80° C. until analysis.

Figure 13:
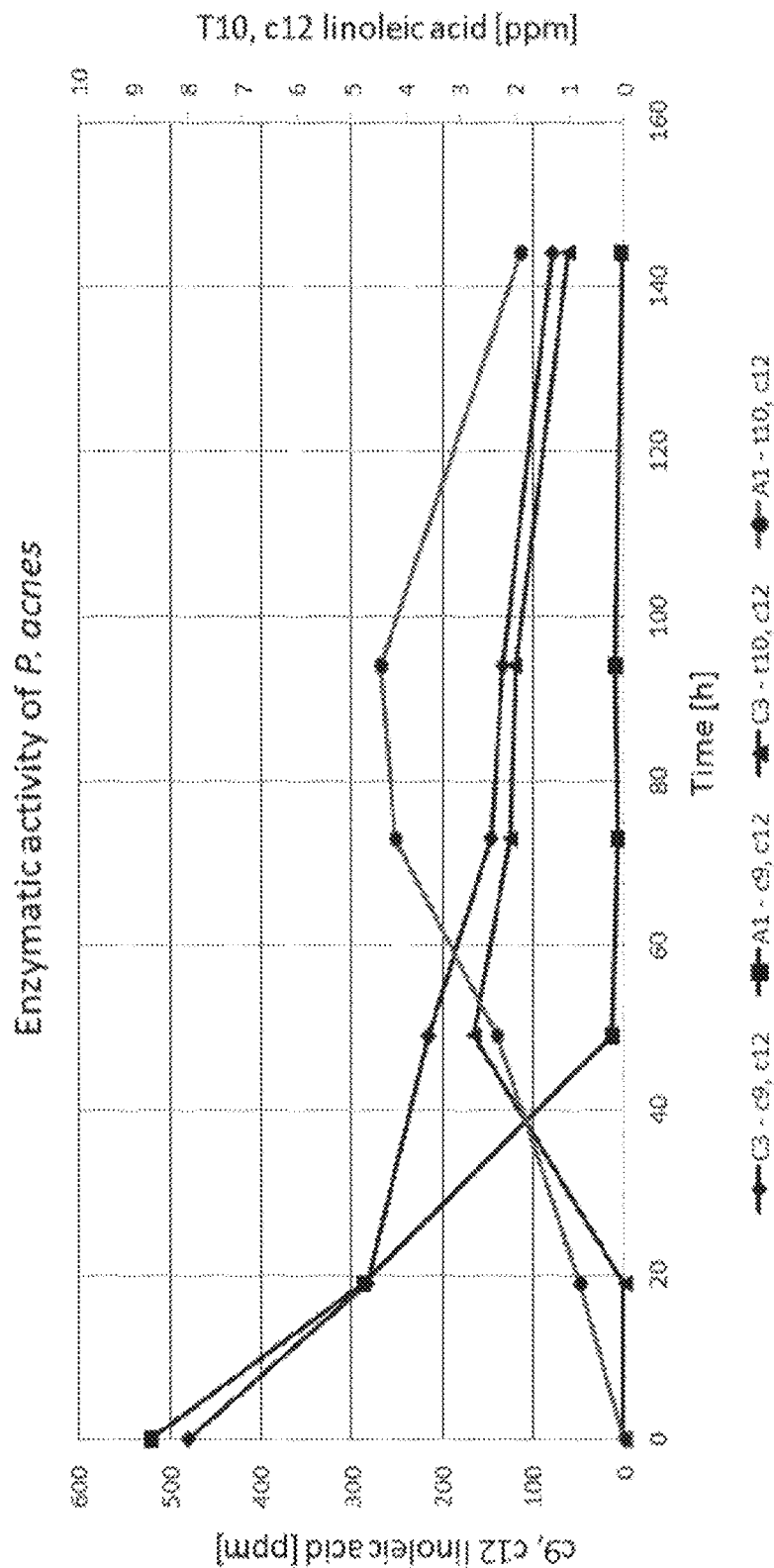
FIG. 13 shows the different conversion rates of cis-9, cis-12 linoleic acid towards trans-10, cis 12 linoleic acid for two *P. acnes* strains (C3, A1). Both strains rapidly degrade the linoleic acid at the beginning; however, while strain A1 completely depletes the cis-9, cis-12 isomer from the media in 48 h, strain C1 slows down the degradation after an initial plunge. This indicates different steady state levels tolerated in vivo by both strains.

Samples were extracted, converted to FAME and then analyzed by GC. The detailed results for the degradation of cis-9, cis-12 linoleic acid and the production of trans-10, cis-12 linoleic acid is shown in FIG. 13. A very rapid decrease of the 9, cis-12 linoleic acid was seen, with most of the degradation occurring in the first 48 h of the experiment. It was also observed that while strain A1 depletes the linoleic acid completely from the medium, the strain C3 surprisingly slows down in degradation of linoleic acid reaching an equilibrium concentration.

Figure 14:
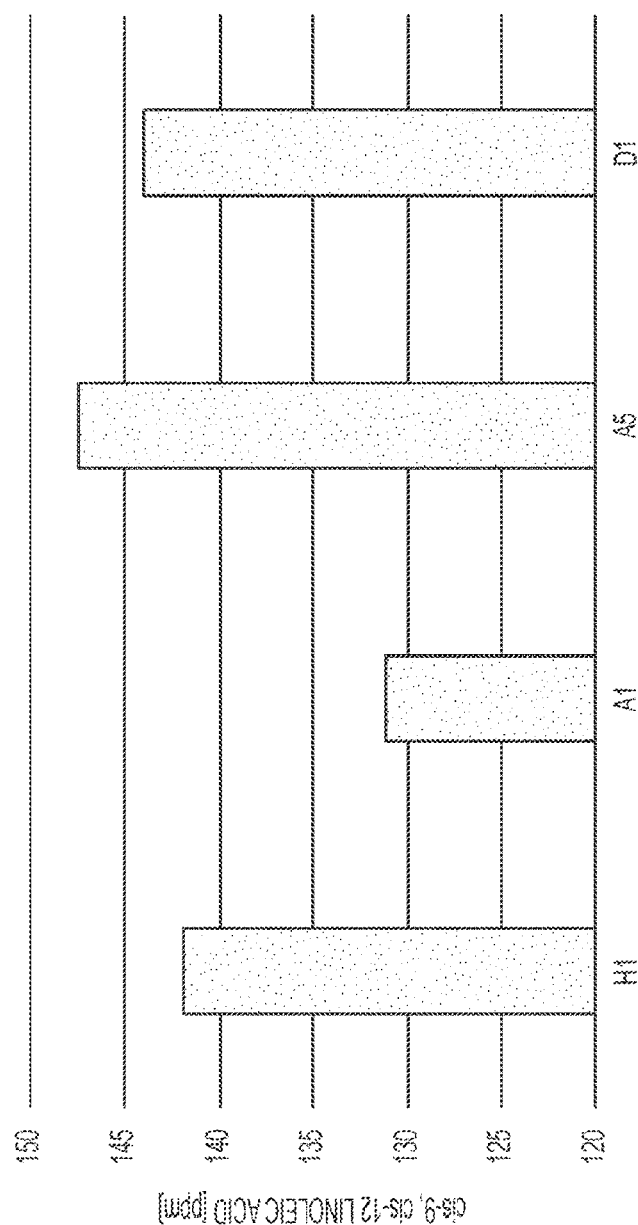
FIG. 14 depicts the degradation of cis-9, cis-12 linoleic acid by different *P. acnes* strains. For each strain, the remaining amount of cis-9, cis-12 linoleic acid after 15 h of shaking incubation is represented. All strains were normalized according to their OD before inoculation and the starting concentration of cis9, cis12 linoleic acid in the media was 500 ppm. The different strains show significant differences in their degradation rate, with A1 degrading linoleic acid the fastest.

Multiple strains were then compared for their ability to degrade 9, cis-12 linoleic acid. For this. 4 strains: A1, H1. D1 and A5 were grown on reinforced clostridial agar plates. The bacteria was then scraped with an inoculation loop and re-suspended in PBS before being normalized and inoculated in RCM with 1.7 mM 9, cis-12 linoleic acid. These samples were incubated at 37° C. with shaking at 200 rpm. The concentration of cis-9, cis-12 linoleic acid was measured 15 h post-inoculation and clear differences were observed between the strains (FIG. 14). This experiment can be repeated for many other strains and serves as an indication of the pathogenicity potential of an individual strain.

Based on information obtained from the above-described experiments, different strains of *P. acnes* are combined in a mixture, which exhibits a minimized linoleic acid isomerase activity or linoleic acid degradation. This mixture can be used to colonize the skin and alter the sebum production rate.

Example 10: Use of Random Mutagenesis to Generate Strains with One or Multiple Mutations in the Linoleic Acid Isomerase Gene A pool of *P. acnes* mutants is generated from a wild type strain by UV or chemical induced random mutagenesis. Individual strains are isolated that have lost their isomerase activity. To obtain these strains, each individual strain can be tested for their activity or multiple strains can be pooled and the isomerase gene can be amplified including upstream regions. Each pool can be sequenced and pools containing a mutant of the isomerase gene can be further split up until the inactive mutants can be efficiently isolated.

Example 11: Definition and Selection of Non-Pathogenic Strains

A meta-analysis of the publicly available data regarding *P. acnes* strains and their association with acne vulgaris was conducted. Based on the meta-analysis, a list of 13 strains which are nonpathogenic was compiled. The group of non-pathogenic strains are D1/A5/H1/H2/H3/F4/K4/K1/K6/K9/K8/K2/L1. However, because multiple strains populate one host, it is difficult to classify frequently occurring strains as non-pathogenic. This implies that rarely occurring strains are over-represented as non-pathogenic, while very frequently occurring strains might be wrongly classified as pathogenic.

It is reasonable to assume that frequently occurring strains have a fitness advantage over other strains. For a stable colonization of the skin it is desirable to use strains with a higher degree of fitness. The ability of any *P. acnes* strain to convert or degrade cis-9, cis-12 linoleic acid as described in Example 9 is therefore used as criteria herein. A slow conversion or degradation of cis-9, cis-12 linoleic acid indicates that a strain is non-pathogenic. A high steady state level of cis-9, cis-12 linoleic acid or a low steady state level of trans-10, cis-12 linoleic acid also indicates that a strain is non-pathogenic.

The SLST sequences used to type the *P. acnes* strains described herein are listed below in Table 1 and correspond to SEQ ID NOs. 1-76.

Primer sequences used to type the bacterial colonies are listed below in Table 2 and correspond to SEQ ID NOs. 77-80. Information on primer sequences is also available at http://medbac.dk/slst/pacnes/protocol.

To prepare a bacteria composition without pathogenic bacteria, complete microbiomes are grown on reinforced clostridial agar plates under anaerobic conditions. Furazolidone (2 µg/mL) is added to inhibit *S. epidermidis* growth. Then, the bacteria are streaked out by classical microbiology methods to obtain single colonies of *P. acnes* which are of clonal origin. These colonies are then typed by PCR amplifying and Sanger-sequencing the SLST region as described by (Scholz et al., 2014). Then, the bacteria are re-streaked for multiple passages to ensure that the colony is a pure clone. It is then stored as a clonal population in RCM medium with 30% glycerol at −80° C.

TABLE 1

Sequences used to identify P. acnes strains by SLST

| SEQ ID NO: | P. Acnes Strain | Sequence |
|---|---|---|
| 1 | A1 | GTTGCACACCAGGGGGTCAACTTGGCGTCCTCAGTTCAAAATTGATTCAAACTAACAGTTCCAT<br>GTCGGGAAACAGGACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 2 | A2 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATTCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 3 | A3 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATGGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAATAACTCGATCCACC<br>CCTGCCCATTACATGGGTAACATATCCATGGAGGTTCGATGTATACTGGAGGATACAGTCGTCC<br>ATCACC3CCCGCCTACATACCCATTACATCAGCATAG |
| 4 | A4 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATGGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 5 | A5 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCACGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCAGTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 6 | A6 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAT |
| 7 | A7 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGCCATCACGAAGGC<br>CACCACAATCTATCCCAGAACAGCCGGCACTTCACTCACGATGCCCCGATTCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 8 | A8 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 9 | A9 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA |

TABLE 1 -continued

Sequences used to identify P. acnes strains by SLST

| SEQ ID NO: | P. Acnes Strain | Sequence |
|---|---|---|
|  |  | TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATCTTCCACCCTGTCATCATGAAGGCC<br>ACCACAATCTATCCCAGAACAGCCGGCACTTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 10 | A10 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCTACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 11 | A11 | GTTGCACACCAGGGGGTCAACTTGGCGTCCTCAGTTCAAAATTGATTCAAACTAACAGTTCCAT<br>GCCGGGAAACAGCACCAGGAAGCCCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 12 | A12 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATATTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 13 | A13 | GTTGCACACCAGGGGGTCAACTTGGCGTCCTCAGTTCAAAATTGATTCAAACTAACAGTTCCAT<br>GTCGGGAAACAGCACCAGGAAGCTGGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 14 | A14 | GTTGCACACCAGGGGGTCAACTTGGCGTTTTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 15 | A15 | GTTGCACACGAGGGGGTCAACTTGGCGTCCTCAGTTCAAAATTGATTCAAACTAACAGTTCCAT<br>GCCGGGAAACAGTACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 16 | A16 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATCCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 17 | A17 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC |

TABLE 1 -continued

Sequences used to identify P. acnes strains by SLST

| SEQ ID NO: | P. Acnes Strain | Sequence |
|---|---|---|
| | | CACCACAATCTATCCCAGAACAGCCGGCACTTCAC1CACGATGCCCCGATGCTGGATTCCTATT<br>GTCGCCCTTATTAGGGCAAGCGGTGCCGGTAGCAGAATATGTCACCTCAACAACTCGATCCACC<br>CCTGCCCATTACATGGGTAACATATCCATGGAGGTTCGATGTATACFCGAGGATACAGTCGTCC<br>ATCACGCCCGCCTACATACCCATTACATCAGCATAG |
| 18 | A18 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGCCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 19 | A19 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCGACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 20 | A20 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>TTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 21 | A21 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACAATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 22 | A22 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTGGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 23 | A23 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGCAATGCCGCGATATATGTTCCACCCTGTCATCACGAAGGC<br>CACCACAATCTATCCCAGAACAGCCGGCACTTCACTCACGATGCCCCGATTCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 24 | B1 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAGCAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 25 | C1 | GTTGCACACCAGGGGGTCAACTTGGCGTCCTCAGTTCAAAATTGATTCAAACTAACAGTTCCAT<br>GTCCGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC |

TABLE 1 -continued

Sequences used to identify P. acnes strains by SLST

| SEQ ID NO: | P. Acnes Strain | Sequence |
|---|---|---|
|  |  | CCTGCCCATTACATGGGTAACATATCCATGGAGGTTCGATGTATACTCGAGGATACAGTCGTCC ATCACGCCCGCCTACATACCCATTACATCAGCATAG |
| 26 | C2 | GTTGCACACCAGGGGGTCAACTTGGCGTCCTCAGTTCAAAATTGATTCAAACTAACAGTTCCAT GTCGGGAAACAGCACCAGGAAGCTCGTGACATATCGTCTTTCATTGCGAGAAACATCTTACTTA TGTACATTTCTAAGCTATAGCGTCTACCCTTGTCAGACCCATGACGATGGGTGTCACATCCCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCAGCATAG |
| 27 | C3 | GTTGCACACCAGGGGGTCAACTTGGCGTCCTTAGTTCAAAATTGATTCAAACTAACAGTTCCAT GTCGGGAAACAGCACCAGGAAGCTCGTGACATATCGTCTTTCATTGCGAGAAACATCTTACTTA TGTACATTTCTAAGCTATAGCGTCTACCCTTGTCAGACCCATGACGATGGGTGTCACATCCCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCAGCCATAG |
| 28 | C4 | GTTGCACACCAGGGGGTCAACTTGGCGTCCTCAGTTCAAAATTGATTCAAACTAACAGTTCCAT GTCGGGAAACAGCACCAGGAAGCTCGTGACATATCGTCTTTCATTGCGAGAAACATCTTACTTA TGTACATTTCTAAGCTATAGCGTCTACCCTTGTCAGACCCAGGACGATGGGTGTCACATCCCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCTGCATAG |
| 29 | D1 | GTTGCACACCAGGGGGTCAACTTGGCGTCCTCAGTTCAAAATTGATTCAAACTAACAGTTCCAT GTCGGGAAACAGCACCAGGAAACTCGTGACATATCGTCTTTCATTGCGAGAAACATCTTACTTA TGTACATTTCTAAGCTATAGCGTCTACCCTTGTCAGACCCAGGACGATGGGTGTCACATCCCCTT TCTAGTCAACCTAAGAGAGGAGGAAATGCCGCGATATATGTTCCGCCCTGTCATCACGAAGAC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTTGAGGATACAGTCGTCC ATCACGCCCACCTACATACCCATTACATCAGCATAG |
| 30 | D2 | GTTGCACACCAGGGGGTCAACTTGGCGTCCTCAGTTCAAAATTGATTCAAACTAACAGTTCCAT GTCGGGAAACAGCACCAGGAAACTCGTCACATATCGTCTTTCATTGCGAGAAACATCTTACTTA TGTACATTTCTAAGCTATAGCGTCTACCCTTGTCAGACCCAGGACGATGGGTGTCACATCCCCTT TCTAGTCAACCTAAGAGAGGAGGAAACGCCGCGATATATGTTCCGCCCTGTCATCACGAAGAC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTTGAGGATACAGTCGTCC ATCACGCCCACCTACATACCCATTACATCAGCATAG |
| 31 | D3 | GTTGCACACCAGGGGGTCAACTTGGCGTCCTCAGTTCAAAATTGATTCAAACTAACAGTTCCAT GTCGGGAAACAGCACCAGGAAACTCGTGACATATCGTCTTTCATTGCGAGAAACATCTTACTTA TGTACATTTCTAAGCTATAGCGTCTACCTTTGTCAGACCCAGGACGATGGGTGTCACATCCCCTT TCTAGTCAACCTAAGAGAGGAGGAAATGCCGCGATATATGTTCCGCCCTGTCATCACGAAGAC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTTGAGGATACAGTCGTCC ATCACGCCCACCTACATACCCATTACATCAGCATAG |
| 32 | E1 | GTTGCACACCAGGGGGTCAACTTGGCGTCCTCAGTTCAAAATTGATTTAAACTAACAGTTCCAT GTCGGGAAACAGCACCAGGAAGCTCGTGACATATCGTCTTTCATTGCGAGAAACATCTTACTTA TGTACATTTCTAAGCTATAGCGTCTACCCTTGTCAGACCCAGGACGATGGATGTCACATCCCCTT TCTAGTCAACCTAAGAGAGGAAATGCCGCGATATATGTTCCACCCTGTCATCACGAAGGC CACCACAATCTATCCCAGAACAGCCGGCACCTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATATTCGAGAATACAGTCGTCC ATCACGCCCGCCTACATACCCATTACATCAGCATAG |
| 33 | E2 | GTTGCACACCAGGGGGTCAACTTGGCGTCCTCAGTTCAAAATTGATTTAAACTAACAGTTCCAT GTCGGGAAACAGCACCAGAAAGCTCGTGACATATCGTCTTTCATTGCGAGAAACATCTTACTTA TGTACATTTCTAAGCTATAGCGTCTACCCTTGTCAGACCCAGGACGGATGTCACATCCCCTT TCTAGTCAACCTAAGAGAGGAGGAAATGCCGCGATATATGTTCCACCCTGTCATCACGAAGGC CACCACAATCTATCCCAGAACAGCCGGCACCTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATATTCGAGGATACAGTCGTCC ATCACGCCCGCCTACATACCCATTACATCAGCATAG |

TABLE 1 -continued

Sequences used to identify P. acnes strains by SLST

| SEQ ID NO: | P. Acnes Strain | Sequence |
|---|---|---|
| 34 | E3 | GTTGCACACCAGGGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 35 | E4 | GTTGCACACCAGGGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGAAGGTTCGATGTATATTCGAGGATACAGTCGTCC<br>ATCACGCCCGCCTACATACCCATTACATCAGCATAG |
| 36 | E5 | GTTGCACACCAGGGGGTCAACTTGGCGTCCTCAGTTCAAAATTGATTTAAACTAACAGTTTCAT<br>GTCGGGAAACAGCACCAGGAAGCTCGTGACATATCGTCTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAC3TAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 37 | E6 | GTTGCACACCAGGGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATTCCGCGATATATGTTCCACCCTGTCATCACGAAGGCC<br>ACCACAATCTATCCCAGAACAGCCGGCACCTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATATTCGAGGATACAGTCGTCCA<br>TCACGCCCGCCTACATACCCATTACATCAGCATAG |
| 38 | E7 | GTTGCACACCAGAGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCCTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 39 | E8 | GTTGCACACCAGGGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACGCTGTCATCACGAAGGC<br>CACCACAATCTATCCCAGAACAGCCGGCGCCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 40 | E9 | GTTGCACACCAGGGGGTCAACTTGGCGTCCTCAGTTCAAAATAGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 41 | F1 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTATATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATTCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |

TABLE 1 -continued

Sequences used to identify *P. acnes* strains by SLST

| SEQ ID NO: | P. Acnes Strain | Sequence |
|---|---|---|
| 42 | F2 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTATATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATTCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATCGGAGGTTCGATGTATACTCGAGGATACAGTCGTCCA<br>TCACGCCCGCCTACATACCCATTACACCAGCATAG |
| 43 | F3 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTATATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATTCTGGATTCCTATTG<br>TCGCCCTTATTAGGGCAAGCGGTGCCAGTAGCAGAATATGTCACCTAAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 44 | F4 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCGCCGATGCTGGATTCCTATTG<br>TCGCCCTTATTAGGGCAAGCGGTGCCAGTAGCAGAATATCTCACCTCAACAACTCGATCCACCC<br>CTGCCCCATTACATGGGTAACATATCCATGGAGGTTCGATGTATACTCGAGGATACAGTCGTCCA<br>TCACGCCCGCCTACATACCCATTACATCAGCATAG |
| 45 | F5 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATGCTAGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 46 | F6 | GTTACACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGAFACACTCGTCCA<br>TCACGCCCGCCTACATACCCATTACATCAGCATAG |
| 47 | F7 | GTTGCACACCAGGGGGTCAACTTGGCGTCCTCAGTTCAAAATTGATTCAAACTAACAGTTCCAT<br>GTCGGGAAACAGCACCAGGAAGCrCGTGACATATCGTCTTTCATrGCGAGAAACATCTTACTTA<br>TGTATATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATTCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCAAGCCCGCCTACATACCCATTACATCAGCATAG |
| 48 | F8 | GTTGCACACCAGGGGGTCAACTTGGCGTCCTCAGTTCAAAATTGATTCAAACTAACAGTTCCAT<br>GTCGGAAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 49 | F9 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATGCTGGATTCCTATTG<br>TCGCCCTTATTAGGGCAAGCGATGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |

TABLE 1 -continued

Sequences used to identify P. acnes strains by SLST

| SEQ ID NO: | P. Acnes Strain | Sequence |
|---|---|---|
| 50 | F10 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACACCCCCT<br>TTCTAGTCAACCTAAGAGAGGAGGAAATGCCGCGATATATGTTCCACCCTGTCATCACGAACGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 51 | G1 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGCCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCGATCCCAGAACAGCCGGCACTTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 52 | H1 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATATCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 53 | H2 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATATCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTCATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 54 | H3 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATATCGTCTCACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 55 | H4 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATATCGTCTACCCTTGTCAGACCCGGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 56 | H5 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCCATATCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 57 | K1 | GTTGCACACCAGGGGGTCAACTTGGTGTCCTCAGTTCAAAATTGATTCAAACTAACGGTTCCGT<br>GTCGGGAAACAGCACCAGAAACTCGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTCTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |

TABLE 1 -continued

Sequences used to identify P. acnes strains by SLST

| SEQ ID NO: | P. Acnes Strain | Sequence |
|---|---|---|
| 58 | K2 | GTTGCACACCAGGGGGTCAACTTGGTGTCCTCAGTTCAAAATTGGTTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 59 | K3 | GTTGCACACCAGGGGGTCAACTTGGTGTCCTCAGTTCAAAATTGATTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATATGTCTACCCCTGTCAGACCCAGGACGATGGGTGTCATATCCCCTTT<br>CCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 60 | K4 | GTTGCACACCAGGGGGTCAACTTGGTGTCCTCAGTTCAAAATTGATTCAAACTAACGGTTCCGT<br>GTCGGGAAACAGCACCAGAAAACTCGTAACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 61 | K5 | GTTGCACACCAGGGGGTCAACTTGGTGTCCTCAGTTCAAAATTGATTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 62 | K6 | GTTGCACACCAGGGGGTCAACTTGGTGTCCTCAGTTCAAAATTGATTCAAACTAACGGTTCCGT<br>GTCGGGAAACAGCACCAGAAAACTCGTGACATATCGTCTTTCATTGCGAGAAACATCTTATTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCGCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 63 | K7 | GTTGCACACCAGGGGGTCAACTTGGTGTCCTCAGTTCAAAATTGATTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGAAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGTTAACATATCCATGGAGGTACGATGTATGCATCGAGGATGCAGTCGTCTA<br>CTATGCCCGCCTACATACCCATTCCATCAGCATAG |
| 64 | K8 | ATTGCACACCAGGGGGTCAACTTGGTGTCCTCAGTTCAAAATTGGTTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 65 | K9 | GTTGCACACCAGGGGGTCAACTTGGTGTCCTCAGTTCAAAATTGGTTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATGGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |

TABLE 1 -continued

Sequences used to identify P. acnes strains by SLST

| SEQ ID NO: | P. Acnes Strain | Sequence |
|---|---|---|
| 66 | K10 | GTTGCACACCAGGGGGTCAACTTGGTGTCCTCAGTTCAAAATTGATTCAAACTAACGGTTCCGT<br>GTCGGGAAACAGCACCAGAAAACTCGTGACATATCATCTTTCATTGCGAGAAACATCTTACTTA<br>TACACATTTCTAAGCTATATGTCTACCCCTGTCAGACCCAGGACGATGGGTGTCATATCCCCTTT<br>CCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 67 | K11 | GTTGCACACCAGGGGGTCAACTTGGTGTCCTCAGTTCAAAATTGGTTCAAACTAACGGTTCCGT<br>GTCGGGAAACAGCACCAGAAAACTCGTGACATGTCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 68 | K12 | GTTGCACACCAGGGGGTCAACTTGGTGTCCTCAGTTCAAAATTGGTTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATACTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 69 | K33 | GTTGCACACCAGGGGGTCAACTTGGTGTCCTCAGTTCAAAATTGGTTCAAACTAACGGTTCCGT<br>GTCGGGAAACAGCACCAGAAAACTTGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 70 | K14 | GTTGCACACCAGGGGGTCAACTTGGTGTCCTCAGTTCAAAATTGGTTCAAACTAACGGTTCCGT<br>GTCCCGAAACAGCACCAGAAAACTCATGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACGCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 71 | L1 | GTTGCACACCAGGGGGTCAACTTGGTGTCCTCAGTTCAAAATTGATTCAAACTAACGGTTCCGT<br>ATCGGGAAACAGCACCAGAAAACTCGGGACATATCGTCTTTCATTGCGAGAAAAATCTTACTTA<br>TGCGCATTTCTAAGCTATAGCGTCTACCCTTGTCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCTGCCCATTACATGGGTAACATATCCATGGAGGTTCGATGTATACTCGAGGATACAGTCGCC<br>CATCACGCCAGCCTACATACCCATTACATCAGCATAG |
| 72 | L2 | GTTGCACACCAGGGGGTCAACTTGGTGTCCTCAGTTCAAAATTGATTCAAACTAACGGTTCCGT<br>ATCGGGAAACAGCACCAGAAAACTCGGGACATATCGTCTTTCATTGCGAGAAAAATCTTACTTA<br>TGCGCATTTCTAAGCTATAGCGTCTACCCTTGCCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCTGCCCATTACATGGGTAACATATCCATGGAGGTTCGATGTATACTCGAGGATACAGTCGCC<br>CATCACGCCAGCCTACATACCCATTACATCAGCATAG |
| 73 | L3 | GTTGCACAGCAGGGGGTCAACTTGGTGTCCTCAGTTCAAAATTGATTCAAACTAACGGTTCCGT<br>ATCGGGAAACAGCACCAGAAAACTCGGGAGATATCGTCTTTCATTGCGAGAAAAATCTTACTTA<br>TGCGCATTTCTAAGCTATATCGTCTACCCTTGCCAGACCCAGGACGATGAGTGTCACATCCCCTT<br>TCCAGTCAACCTAAGAGAGGAGGAAATGCCGCGATATATGCTCCGCCCTGTCATCACGAAAGC<br>CACCACAATCTATCCCAGAACAGCCGGCACTTCACTCACGATGCCCCGATGCTGGATTCCTATT<br>GTCGCCCATTAGGGCAAGCGGTGCCAGTAGCAGAATATGTCACCTCAGCAACTCGATCCGCC<br>CCTGCCCATTACATGGGTAACATATCCATGGAGGTTGGATGTATACTCGAGGATACAGTCGCCC<br>ATCACGCCAGCCTACATACCCATTACATCAGCATAG |

TABLE 1 -continued

Sequences used to identify P. acnes strains by SLST

| SEQ ID NO: | P. Acnes Strain | Sequence |
|---|---|---|
| 74 | L4 | GTTGCACACCAGGGGGTCAACTTGGTGTCCTCAGTTCAAAATTGATTCAAACTAACGGTTCCGT<br>GTCGGGAAACAGCACCAGAAAACTCGGGACATATCGTCTTTCATTGCGAGAAAAATCTTACTTA<br>TGCGCATTTCTAAGCTATAGCGTCTACCCTTGTCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCTGCCCATTACATGGTTAACATATCCATGGAGGTTCGATGTATACTCGAGGATACAGTCGCC<br>CATCACGCCAGCCTACATACCCATTACATCAGCATAG |
| 75 | L5 | GTTGCACACCAGGGGGTCAACTTGGTGTCCTCAGTTCAAAATTGATTCAAACTAACGGTTCCGT<br>GTCGGGAAACAGCACCAGAAAACTCGGGACATATCGTCTTTCATTGCGAGAAAAATCTTACTTA<br>TGCGCATTTCTAAGCTATAGCGTCTACCCTTGTCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCTGCCCATTACATGGGTAACATATCCATGGAGGTTCGATGTATACTCGAGGATACAGTCGCC<br>CATCACGCCAGCCTACATACCCATTACATCAGCATAG |
| 76 | L6 | GTTGCACACCAGGGGGTCAACTTGGTGTCCTCAGTTCAAAATTGATTCAAACTAACGGTTCCGT<br>ATCGGGAAACAGCACCAGAAAACTCGGGACATATCGTCTTTCATTGCGAGAAAAATCTTACTTA<br>TGCGCATTTCTAAGCTATAGCGTCTACCCTTGTCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCCGCCCATTACATGGGTAACATATCCATGGAGGTTCGATGTATACTCGAGGATACAGTCGCC<br>CATCACGCCAGCCTACATACCCATTACATCAGCATAG |

TABLE 2

Primer sequences used to type bacterial colonies

| SEQ ID NO: | Description | Sequence |
|---|---|---|
| 77 | Forward primer | CAGCGGCGCTGCTAAGAACTT |
| 78 | Reverse primer | CCGGCTGGCAAATGAGGCAT |
| 79 | SLST Adapter FW | TCGTCGGCAGCGTCAGATGTGTATAAG<br>AGACAGCAGCGGCGCTGCTAAGAACTT |
| 80 | SLST Adapter RV | GTCTCGTGGGCTCGGAGATGTGTATAA<br>GAGACAGCCGGCTGGCAAATGAGGCAT |

Example 12: Composition of a Cosmetic or Pharmaceutical Product

The compositions comprising one or more live bacterial strains is used as a cosmetic or a pharmaceutical product. Such a product includes one or more live P. acnes strains as described above in addition to peptone or another liquid carrying media in which the bacterial composition stays stable. In some embodiments, the composition is a gel including a gelling compound like hydroxyethyl cellulose or similar.

Compositions described herein can modulate features of the skin such as moisture and pH, resulting in enhancing the beauty and appearance of the skin. Some bacterial compositions described herein can modulate the sebum production and lipid content on the skin, which is particularly beneficial in acne-prone skin and elderly skin.

Compositions described herein can increase or decrease the equilibrium concentration of cis-9, cis-12 linoleic acid or its isomers trans-10, cis-12 linoleic acid in the sebum from its naturally occurring concentration on the skin to a higher or lower concentration. Thereby, the product indirectly delivers the respective compound to the cells of the sebaceous glands and follicles.

Compositions described herein can change the degradation rate of cis-9, cis-12 linoleic acid and thereby indirectly deliver cis-9, cis-12 linoleic acid to the cells in the sebaceous glands.

Additionally, compositions described herein may include compounds such as hyaluronic acid or lactic acid or other compounds to enhance the features of the bacterial composition.

A product comprising a composition described herein is delivered in a packaging protected from light and is stored at room temperature. In some forms, the product can be packaged as a two-component composition, wherein the bacterial composition is freeze-dried and is mixed into the carrying media, such as peptone, before use.

REFERENCES

Allgaier, H., Jung, G., Werner, R. G., Schneider, U., and Zähner, H. (1986). Epidermin: sequencing of a heterodetic tetracyclic 21-peptide amide antibiotic. Eur. J. Biochem. FEBS 160, 9-22.

Azoulay, L., Oraichi, D., and Bérard, A. (2007). Isotretinoin therapy and the incidence of acne relapse: a nested case-control study. Br. J. Dermatol. 157, 1240-1248.

Bek-Thomsen, M., Lomholt. H. B., and Kilian, M. (2008). Acne is not associated with yet-uncultured bacteria. J. Clin. Microbiol. 46, 3355-3360.

Belkaid, Y., and Segre, J. A. (2014). Dialogue between skin microbiota and immunity. Science 346, 954-959.

Berson, D. S., Chalker, D. K., Harper, J. C., Leyden, J. J., Shalita. A. R., and Webster, G. F. (2003). Current concepts in the treatment of acne: report from a clinical roundtable. Cutis 72, 5-13.

Brüggemann, H., Lomholt, H. B., Tettelin, H., and Kilian, M. (2012). CRISPR/cas loci of type II *Propionibacterium acnes* confer immunity against acquisition of mobile elements present in type I *P. acnes*. PloS One 7, e34171.

Churruca, I., Fernández-Quintela, A., and Portillo, M. P. (2009). Conjugated linoleic acid isomers: differences in metabolism and biological effects. BioFactors Oxf. Engl. 35, 105-111.

Consortium, T. H. M. P. (2012). Structure, function and diversity of the healthy human microbiome. Nature 486, 207-214.

Doré, J., and Blottière, H. (2015). The influence of diet on the gut microbiota and its consequences for health. Curr. Opin. Biotechnol. 32C. 195-199.

Downing, D. T., Stewart. M. E., Wertz, P. W., and Strauss, J. S. (1986). Essential fatty acids and acne. J. Am. Acad. Dermatol. 14, 221-225.

Draelos, Z. D. (2009). Cosmeceuticals: undefined, unclassified, and unregulated. Clin. Dermatol. 27, 431-434.

Fitz-Gibbon. S., Tomida. S., Chiu. B.-H., Nguyen, L., Du, C., Liu. M., Elashoff, D., Erfe, M. C., Loncaric, A., Kim, J., et a. (2013). *Propionibacterium acnes* strain populations in the human skin microbiome associated with acne. J. Invest. Dermatol. 133, 2152-2160.

Flores, G. E., Henley, J. B., and Fierer, N. (2012). A Direct PCR Approach to Accelerate Analyses of Human-Associated Microbial Communities. PLoS ONE 7.

Götz, F., Perconti, S., Popella, P., Werner. R., and Schlag. M. (2014). Epidermin and gallidermin: Staphylococcal lantibiotics. Int. J. Med. Microbiol. UMM 304, 63-71.

Grice, E. A., and Segre. J. A. (2011). The skin microbiome. Nat. Rev. Microbiol. 9.244-253.

Holmes. A. D. (2013). Potential role of microorganisms in the pathogenesis of rosacea. J. Am. Acad. Dermatol. 69, 1025-1032.

Hong Lioe Ko. S., Heczko, P. B., and Pulverer, G. (1978). Differential Susceptibility of *Propionibacterium acnes, P. granulosum* and *P. avidum* to Free Fatty Acids. J. Invest. Dermatol. 71, 363-365.

Hunyadkirti. J., Feltóti, Z., Horváth, B., Nagymihály, M., Vörös, A., McDowell, A., Patrick, S., Urbán, E., and Nagy, I. (2011). Complete Genome Sequence of *Propionibacterium* acnes Type IB Strain 6609. J. Bacteriol. 193, 4561-4562.

Iinuma, K., Sato, T., Akimoto, N., Noguchi. N., Sasatsu, M., Nishijima, S., Kurokawa, I., and Ito, A. (2009). Involvement of *Propionibacterium acnes* in the Augmentation of Lipogenesis in Hamster Sebaceous Glands In Vivo and In Vitro. J. Invest. Dermatol. 129, 2113-2119.

Kasimatis, G., Fitz-Gibbon, S., Tomida, S., Wong, M., and Li, H. (2013). Analysis of complete genomes of *Propionibacterium acnes* reveals a novel plasmid and increased pseudogenes in an acne associated strain. BioMed Res. Int. 2013, 918320.

Kearney. J. N., Ingham, E., Cunliffe. W. J., and Holland, K. T. (1984). Correlations between human skin bacteria and skin lipids. Br. J. Dermatol. 110, 593-599.

King. K., Jones, D. H., Daltrey, D. C., and Cunliffe, W. J. (1982). A double-blind study of the effects of 13-cis-retinoic acid on acne, sebum excretion rate and microbial population. Br. J. Dermatol. 107, 583-590.

Kong, H. H., Oh, J., Deming, C., Conlan, S., Grice, E. A., Beatson, M. A., Nomicos, E., Polley, E. C., Komarow, H. D., Murray. P. R., et al. (2012). Temporal shifts in the skin microbiome associated with disease flares and treatment in children with atopic dermatitis. Genome Res. 22, 850-859.

Letawe, C., Boone, M., and Piérard, G. E. (1998). Digital image analysis of the effect of topically applied linoleic acid on acne microcomedones. Clin. Exp. Dermatol. 23.56-58.

Leyden, J. (2001). Current issues in antimicrobial therapy for the treatment of acne. J. Eur. Acad. Dermatol. Venereol. 15, 51-55.

Lomholt, H. B., and Kilian, M. (2010). Population Genetic Analysis of *Propionibacterium acnes* Identifies a Subpopulation and Epidemic Clones Associated with Acne. PLoS ONE 5.

Madli Puhvel, S., and Reisner, R. M. (1970). Effect of Fatty Acids on the Growth of *Corynebacterium Acnes* in Vitro. J. Invest. Dermatol. 54, 48-52.

Makrantonaki, E., Ganceviciene. R., and Zouboulis, C. (2011). An update on the role of the sebaceous gland in the pathogenesis of acne. Dermatoendocrinol. 3, 41-49.

McDowell, A., Barnard, E., Nagy, I., Gao, A., Tomida, S., Li, H., Eady, A., Cove, J., Nord, C. E., and Patrick, S. (2012). An Expanded Multilocus Sequence Typing Scheme for *Propionibacterium acnes*: Investigation of "Pathogenic". "Commensal" and Antibiotic Resistant Strains. PLoS ONE 7, e41480.

McLane, J. (2001). Analysis of common side effects of isotretinoin. J. Am. Acad. Dermatol. 45, S188-194.

Mourelatos, K., Eady, E. a., Cunliffe, W. j., Clark, S. m., and Cove, J. h. (2007). Temporal changes in sebum excretion and propionibacterial colonization in preadolescent children with and without acne. Br. J. Dermatol. 156, 22-31.

Moya-Camarena, S. Y., Heuvel, J. P. V., Blanchard, S. G., Leesnitzer, L. A., and Belury. M. A. (1999). Conjugated linoleic acid is a potent naturally occurring ligand and activator of PPARα. J. Lipid Res. 40.1426-1433.

NIH HMP Working Group. Peterson. J., Garges, S., Giovanni. M., McInnes. P., Wang. L., Schloss, J. A., Bonazzi, V., McEwen, J. E., Wetterstrand, K. A., et al. (2009). The NIH Human Microbiome Project. Genome Res. 19.2317-2323.

van Nood, E., Vrieze, A., Nieuwdorp, M., Fuentes, S., Zoetendal, E. G., de Vos, W. M., Visser, C. E., Kuijper. E. J., Bartelsman, J. F. W. M., Tijssen, J. G. P., et al. (2013). Duodenal Infusion of Donor Feces for Recurrent *Clostridium difficile*. N. Engl. J. Med. 368, 407-415.

Oh. J., Byrd. A. L., Deming. C., Conlan, S., NISC Comparative Sequencing Program. Kong, H. H., and Segre, J. A. (2014). Biogeography and individuality shape function in the human skin metagenome. Nature 514, 59-64.

Olle, B. (2013). Medicines from microbiota. Nat. Biotechnol. 31.309-315.

Pappas. A., Johnsen, S., Liu, J.-C., and Eisinger, M. (2009). Sebum analysis of individuals with and without acne. Dermatoendocrinol. 1, 157-161.

Pierre, A.-S., Minville-Walz, M., Fevre, C., Hichami, A., Gresti, J., Pichon, L., Bellenger, S., Bellenger, J., Ghiringhelli, F., Narce, M., et al. (2013). Trans-10, cis-12 conjugated linoleic acid induced cell death in human colon cancer cells through reactive oxygen species-mediated ER stress. Biochim. Biophys. Acta BBA—Mol. Cell Biol. Lipids 1831, 759-768.

Rivier, M., Castiel, I., Safonova, I., Ailhaud. G., and Michel, S. (2000). Peroxisome proliferator-activated receptor-alpha enhances lipid metabolism in a skin equivalent model. J. Invest. Dermatol. 114, 681-687.

Rohland, N., and Reich, D. (2012). Cost-effective, high-throughput DNA sequencing libraries for multiplexed target capture. Genome Res. 22, 939-946.

Ross, J. I., Snelling, A. M., Eady, E. A., Cove, J. H., Cunliffe, W. J., Leyden. J. J., Collignon. P., Dréno. B., Reynaud, A., Fluhr, J., et al. (2001). Phenotypic and genotypic characterization of antibiotic-resistant *Propionibacterium acnes* isolated from acne patients attending dermatology clinics in Europe, the U.S.A., Japan and Australia. Br. J. Dermatol. 144.339-346.

Rosson, R. A., Grund, A. D., Deng, M.-D., and Sanchez-Riera, F. (2004). Linoleate isomerase. Schnell. N., Entian. K. D., Schneider, U., Götz, F., Zähner. H., Kellner, R., and Jung, G. (1988). Prepeptide sequence of epidermin, a ribosomally synthesized antibiotic with four sulphide-rings. Nature 333, 276-278.

Scholz, C. F. P., Jensen, A., Lomholt, H. B., Brüggemann, H., and Kilian, M. (2014). A Novel High-Resolution Single Locus Sequence Typing Scheme for Mixed Populations of *Propionibacterium acnes* In Vivo. PLoS ONE 9, e104199.

Sörensen, M., Mak, T. N., Hurwitz, R., Ogilvie, L. A., Mollenkopf. H. J., Meyer, T. F., and Brüggemann, H. (2010). Mutagenesis of *Propionibacterium acnes* and analysis of two CAMP factor knock-out mutants. J. Microbiol. Methods 83.211-216.

Tripathi, S. V., Gustafson, C. J., Huang, K. E., and Feldman, S. R. (2013). Side effects of common acne treatments. Expert Opin. Drug Saf. 12, 39-51.

Wang, Y., Kuo. S., Shu. M., Yu, J., Huang. S., Dai, A., Two, A., Gallo, R. L., and Huang, C.-M. (2014). *Staphylococcus epidermidis* in the human skin microbiome mediates fermentation to inhibit the growth of *Propionibacterium acnes*: implications of probiotics in acne vulgaris. Appl. Microbiol. Biotechnol. 98, 411-424.

Zhao, L. (2010). Genomics: The tale of our other genome. Nature 465, 879-880.

Zouboulis, C. C. (2004). Acne and sebaceous gland function. Clin. Dermatol. 22.360-366. (2012). Special human Micmbiota issue. Nature 486.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A method for treating acne, comprising:
topically administering a disinfectant or antibiotic to skin of a subject with acne; and
topically administering a composition comprising one or more live bacterial strains to the skin of the subject following administration of the disinfectant or antibiotic, wherein the one or more live bacterial strains are *Propionibacterium acnes* (*P. acnes*) bacterial strains that comprise a sequence selected from any one of SEQ ID NOs: 5, 25, 44 and 58.

2. The method according to claim 1, wherein the one or more *P. acnes* bacterial strains express no linoleic acid isomerase.

3. The method according to claim 1, wherein the one or more *P. acnes* bacterial strains have no linoleic acid isomerase activity.

4. The method according to claim 1, wherein the one or more *P. acnes* bacterial strains comprise a loss-of-function mutation in a linoleic acid isomerase gene.

5. The method according to claim 1, wherein the composition is a gel, cream, ointment, lotion, serum, powder, aerosol spray or two-component dispensing system.

6. The method according to claim 1, wherein the composition further comprises one or more of a buffer, thickener or carrier.

7. The method according to claim 1, wherein the composition is stable at room temperature for at least three months.

8. The method according to claim 1, wherein the composition is not naturally occurring.

9. The method according to claim 1, wherein the composition further comprises peptone.

10. The method according to claim 1, wherein the subject is a human.

11. The method according to claim 1, wherein one or more of the live bacterial strains is a component of a skin microbiome.

12. The method according to claim 1, wherein at least one of the live bacterial strains is resistant to the antibiotic or disinfectant.

* * * * *